(12) United States Patent
Kimura et al.

(10) Patent No.: US 7,727,247 B2
(45) Date of Patent: Jun. 1, 2010

(54) LIVING TISSUE LIGATION DEVICE

(75) Inventors: Ko Kimura, Hachioji (JP); Kiyotaka Matsuno, Sagamihara (JP); Takayuki Suzuki, Yokohama (JP); Junichi Muramatsu, Akiruno (JP); Tsukasa Kobayashi, Hachioji (JP); Hideki Shimonaka, Hachioji (JP)

(73) Assignee: Olympus Corporation, Tokyo (JP)

( * ) Notice: Subject to any disclaimer, the term of this patent is extended or adjusted under 35 U.S.C. 154(b) by 116 days.

(21) Appl. No.: 11/062,210

(22) Filed: Feb. 18, 2005

(65) Prior Publication Data

US 2005/0143767 A1 Jun. 30, 2005

Related U.S. Application Data

(63) Continuation of application No. PCT/JP03/10598, filed on Aug. 21, 2003.

(30) Foreign Application Priority Data

| Aug. 21, 2002 | (JP) | ............................. 2002-240673 |
| Oct. 1, 2002 | (JP) | ............................. 2002-288934 |
| Oct. 1, 2002 | (JP) | ............................. 2002-288935 |

(51) Int. Cl.
*A61B 17/12* (2006.01)

(52) U.S. Cl. ...................................... 606/157; 606/142

(58) Field of Classification Search ................. 606/142, 606/157, 158

See application file for complete search history.

(56) References Cited

U.S. PATENT DOCUMENTS

| 3,958,576 | A | * | 5/1976 | Komiya | ........................ 606/142 |
| 4,177,813 | A | * | 12/1979 | Miller et al. | ................. 606/139 |
| 4,458,682 | A | * | 7/1984 | Cerwin | ......................... 606/158 |
| 5,171,252 | A | * | 12/1992 | Friedland | ..................... 606/151 |
| 5,464,416 | A | * | 11/1995 | Steckel | ......................... 606/158 |
| 5,520,701 | A | * | 5/1996 | Lerch | .......................... 606/142 |
| 5,569,274 | A | * | 10/1996 | Rapacki et al. | .............. 606/158 |
| 2002/0045909 | A1 | * | 4/2002 | Kimura et al. | .............. 606/151 |

FOREIGN PATENT DOCUMENTS

| JP | 4-26091 | 6/1992 |
| JP | 8-280701 | 10/1996 |
| JP | 2001-520069 | 10/2001 |
| JP | 2002-65598 | 3/2002 |
| JP | 2002-191609 | 7/2002 |
| JP | 2002-360585 | 12/2002 |
| WO | WO 91/08708 | 6/1991 |
| WO | WO 99/20183 | 4/1999 |
| WO | WO 01/10321 A1 | 2/2001 |

* cited by examiner

*Primary Examiner*—Anhtuan T Nguyen
*Assistant Examiner*—Ryan J Severson
(74) *Attorney, Agent, or Firm*—Scully, Scott, Murphy & Presser, P.C.

(57) ABSTRACT

This invention includes a clip having arms which grip living tissue, a press tube serving as a clamping member which is fitted and mounted on the clip to close the arms of the clip, a coupling member which can be inserted into the press tube and engages with the clip, and projections serving as lock portions which hold the arms of the clip in a closed state when the clip engages with the press tube.

21 Claims, 60 Drawing Sheets

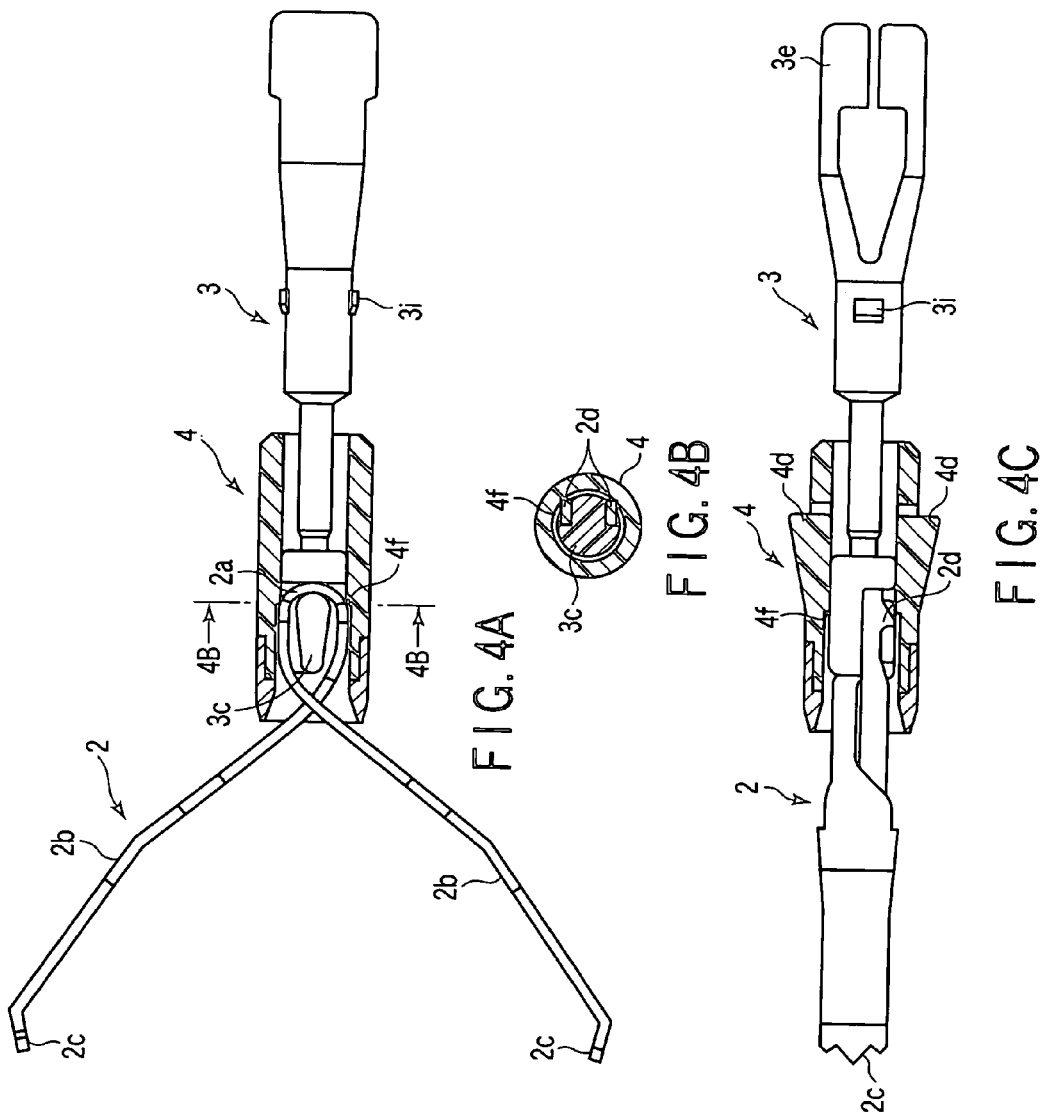

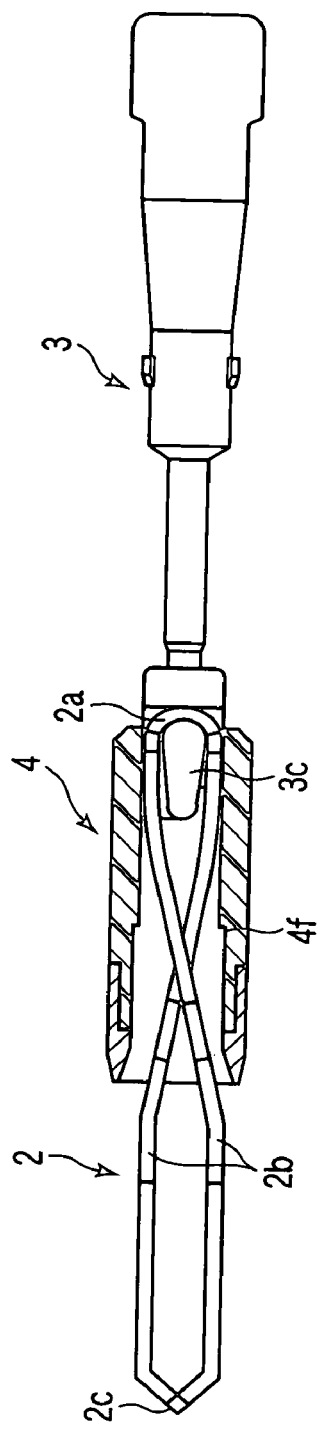
F I G. 5A
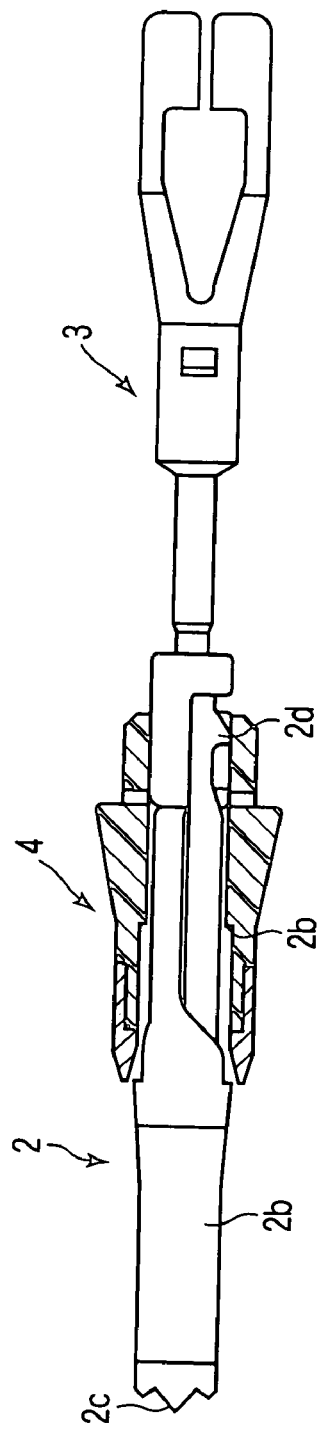
F I G. 5B

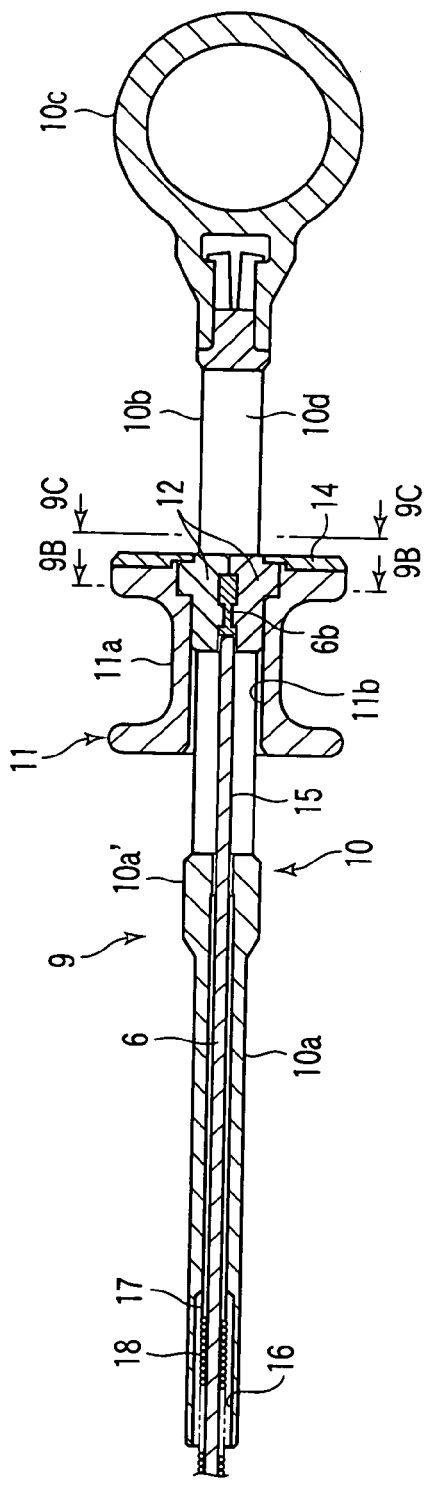
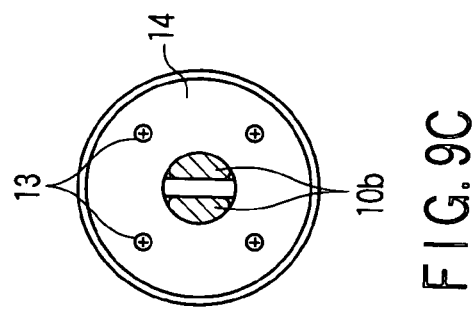
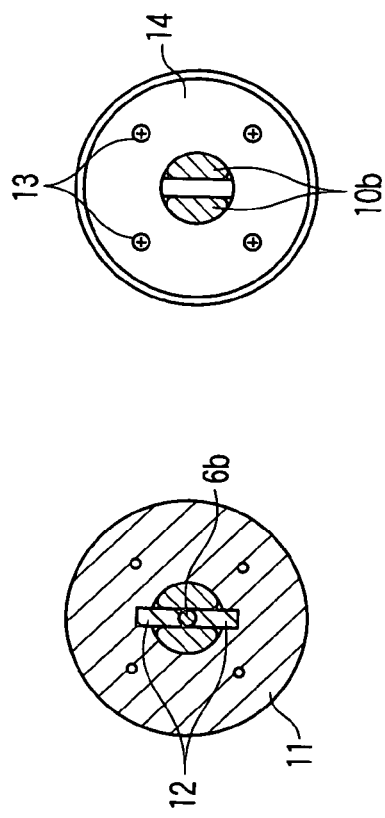

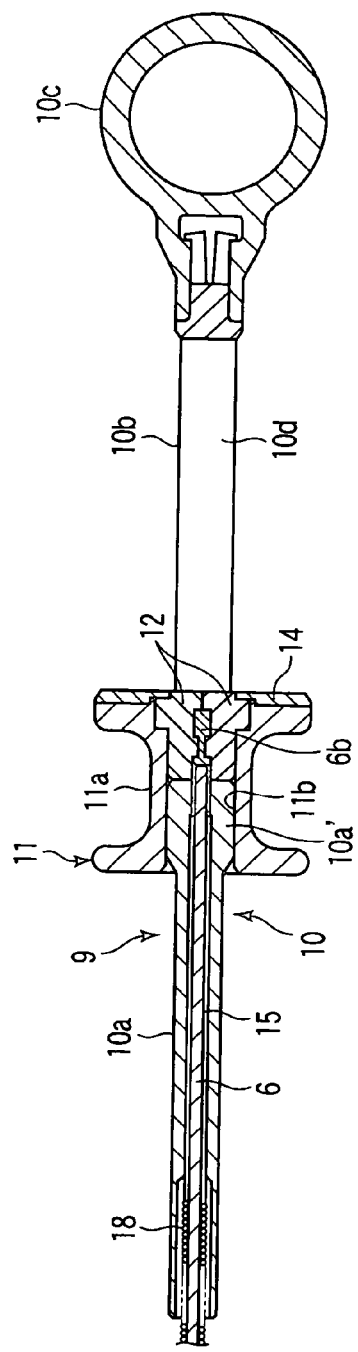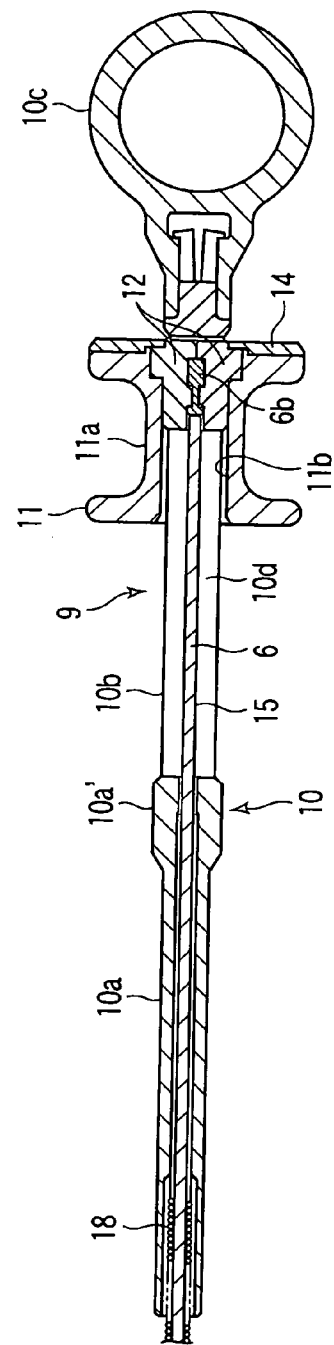
F I G. 10A
F I G. 10B

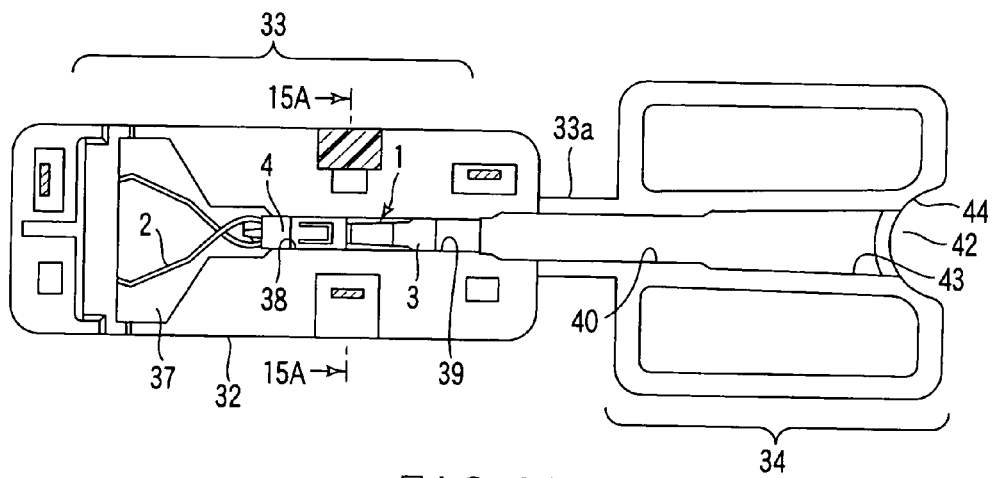
FIG. 14A
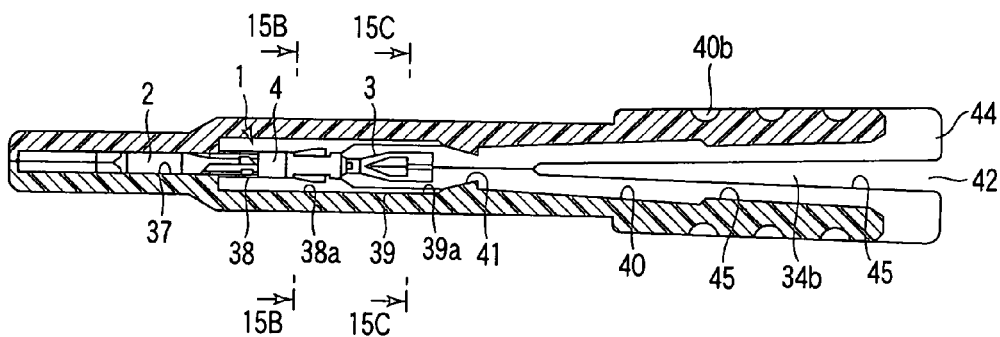
FIG. 14B
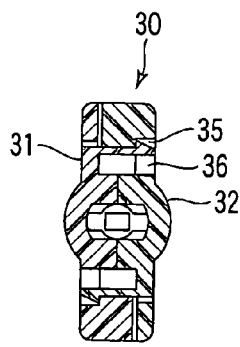 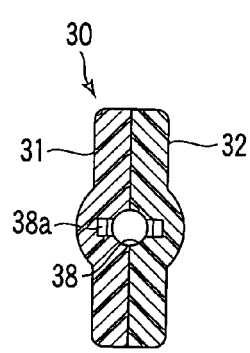 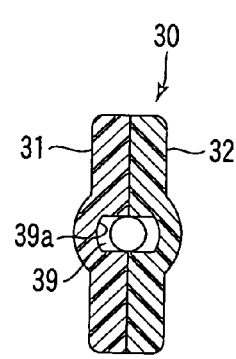
FIG. 15A  FIG. 15B  FIG. 15C

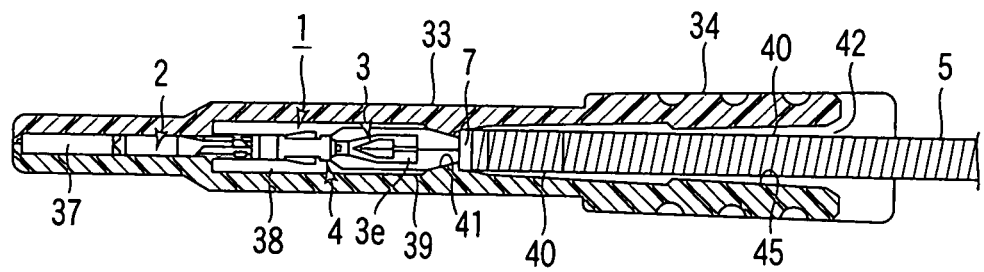
F I G. 18A
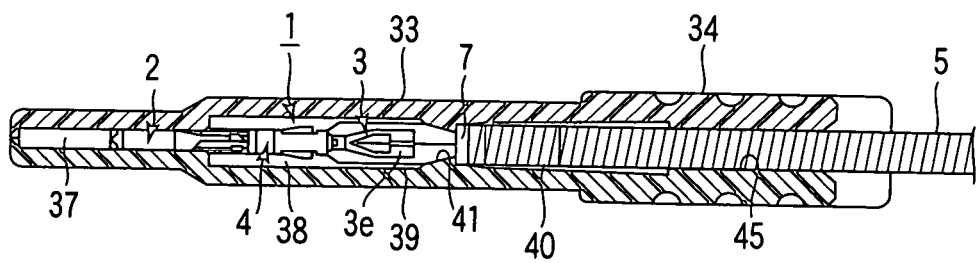
F I G. 18B
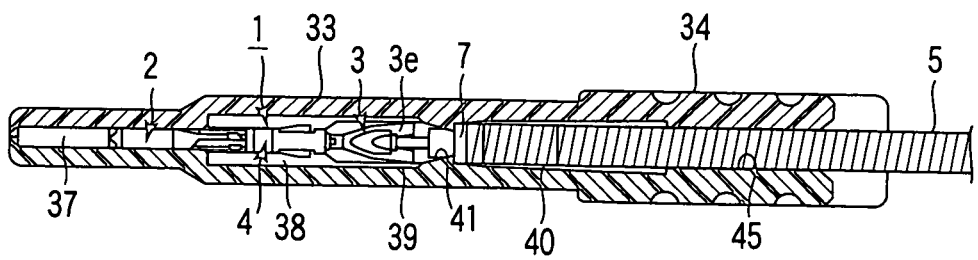
F I G. 18C

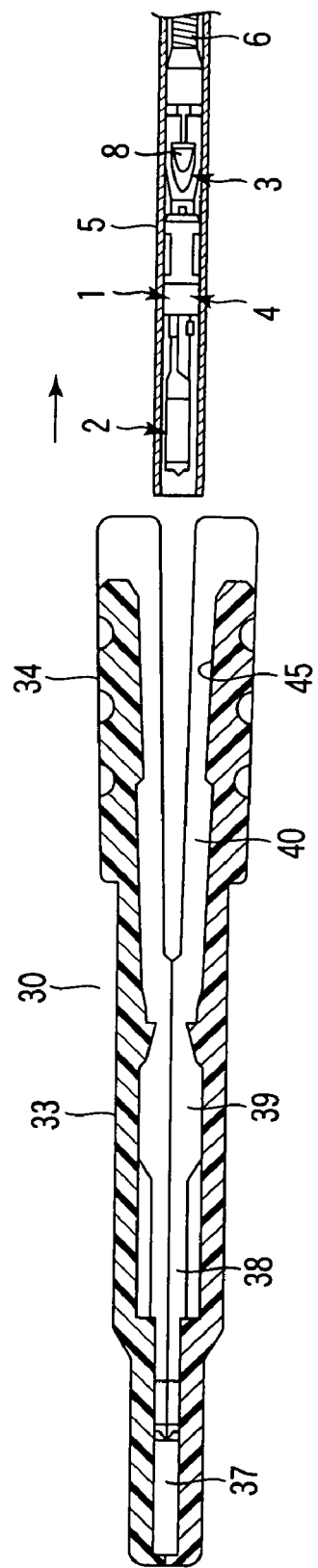
F I G. 20

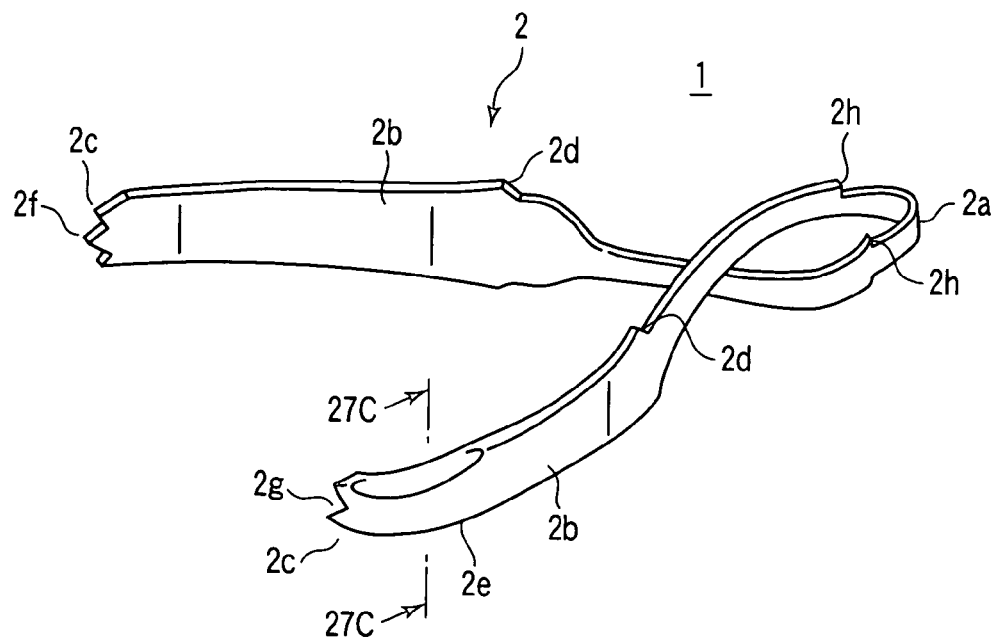
FIG. 27A
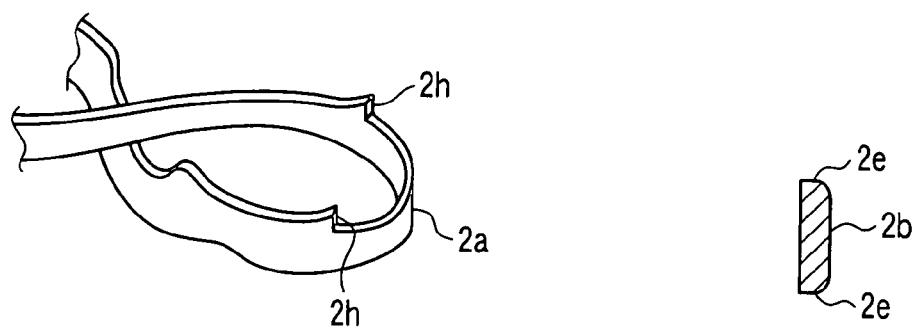
FIG. 27B
FIG. 27C

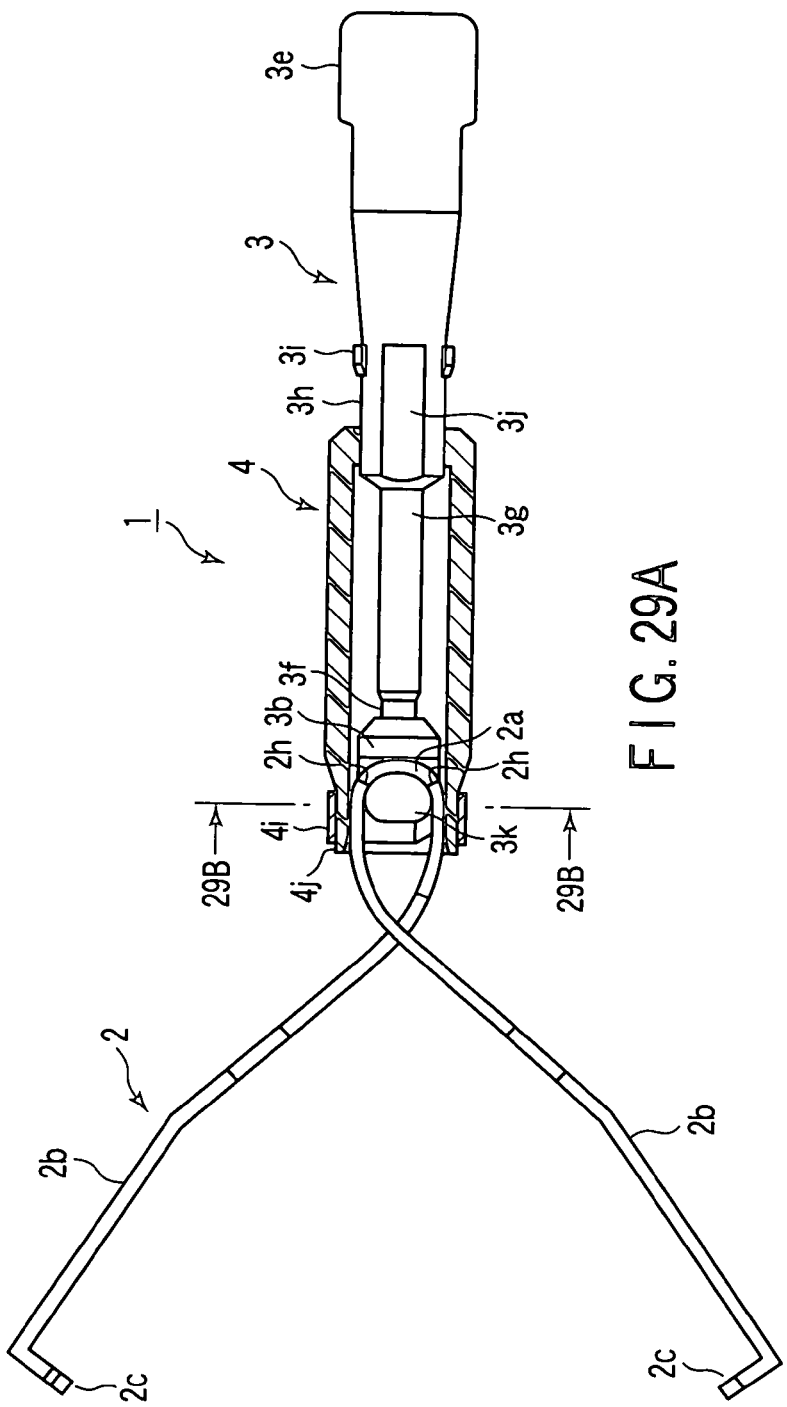
F I G. 29A
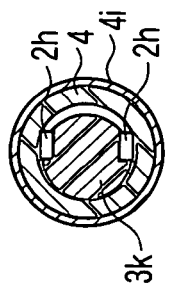
F I G. 29B

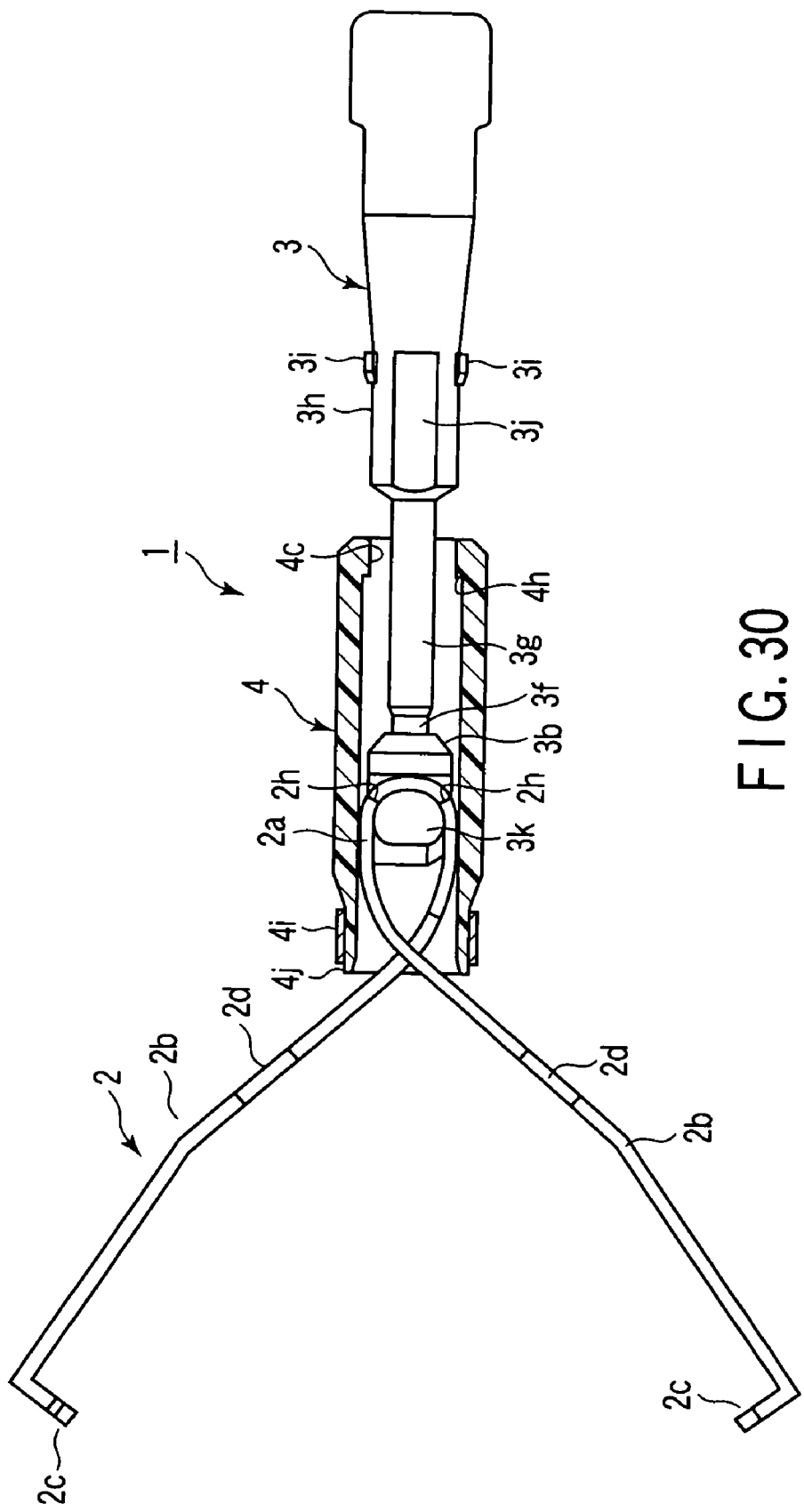
F I G. 30

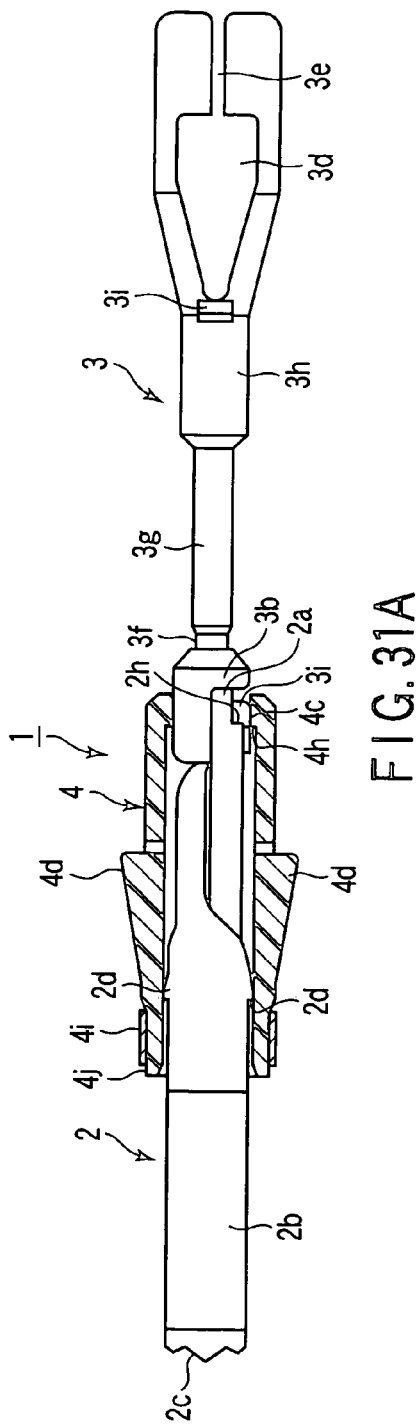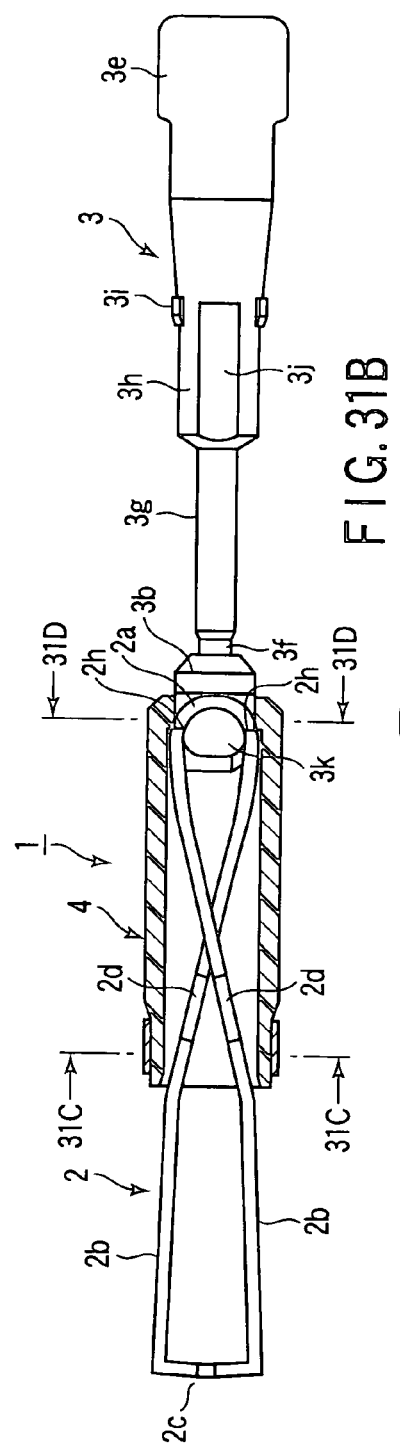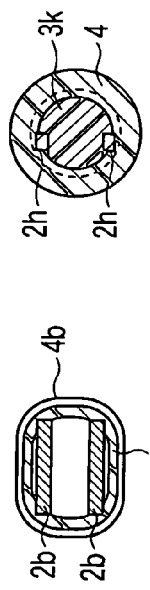
FIG. 31A
FIG. 31B
FIG. 31C
FIG. 31D

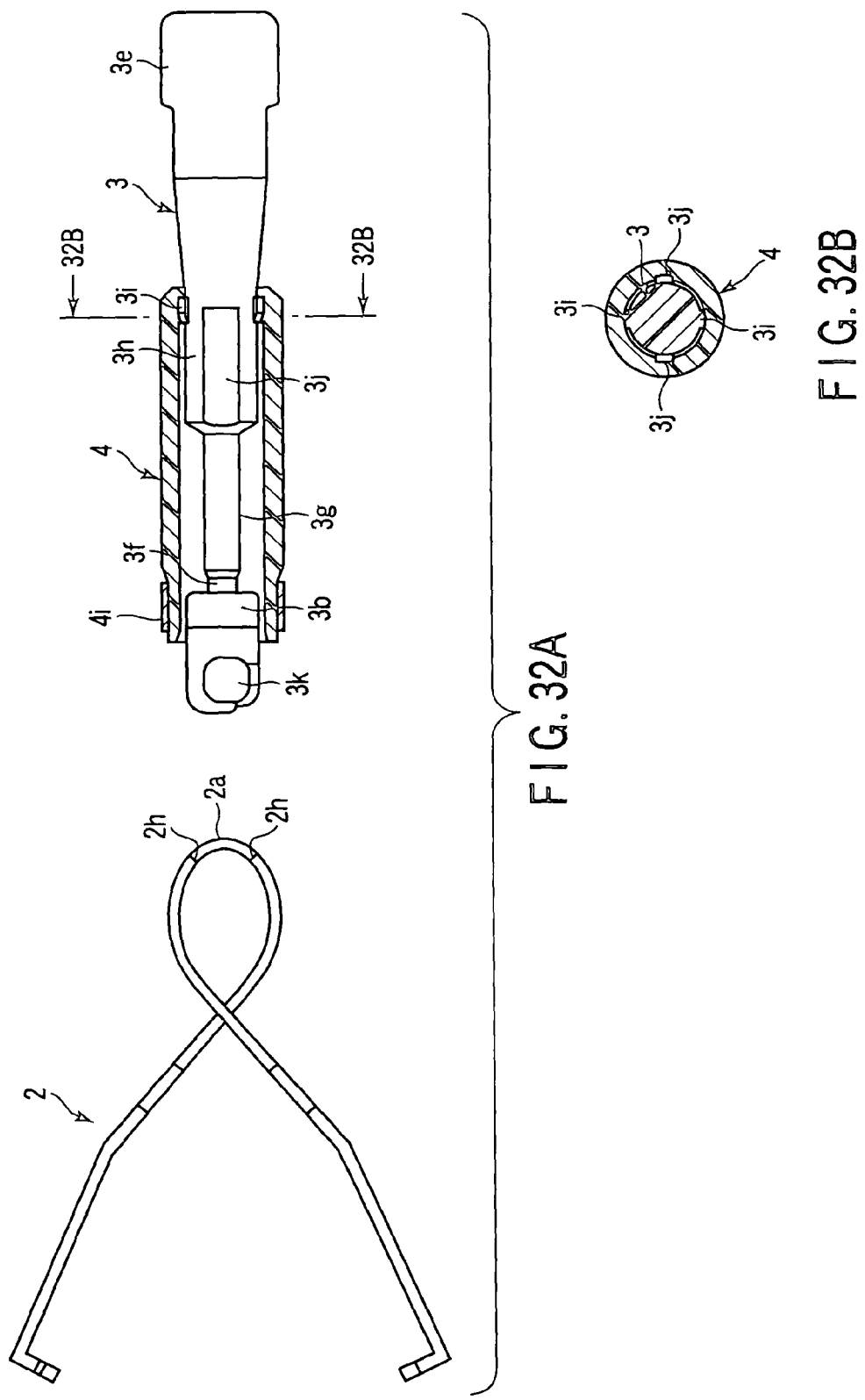

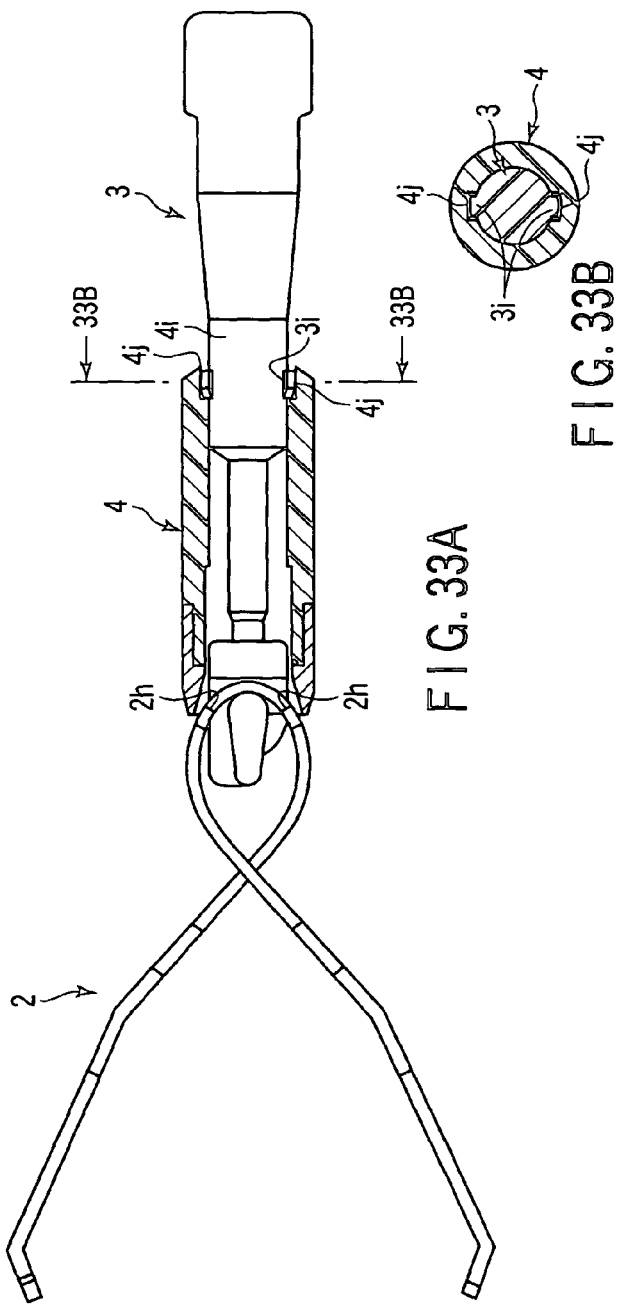
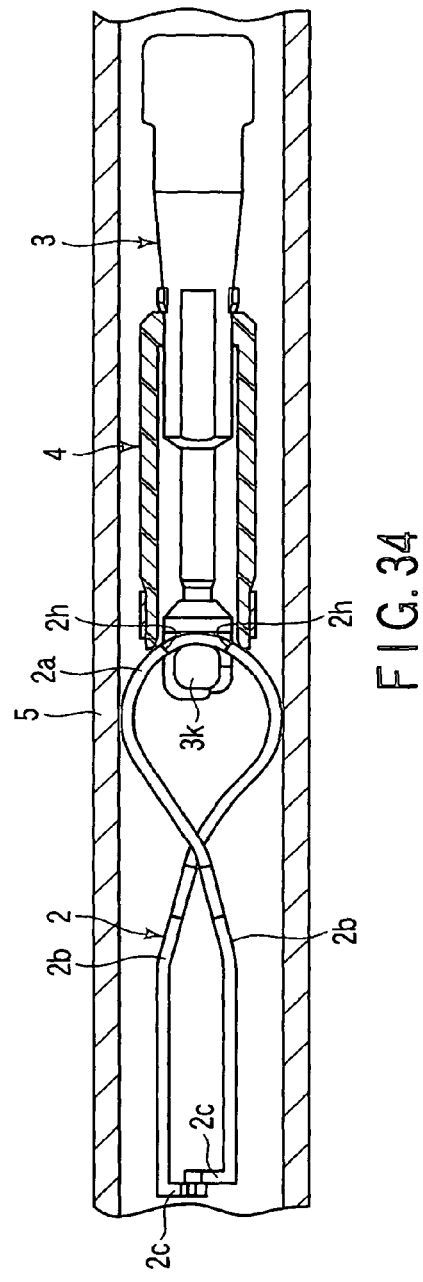
FIG. 33A
FIG. 33B
FIG. 34

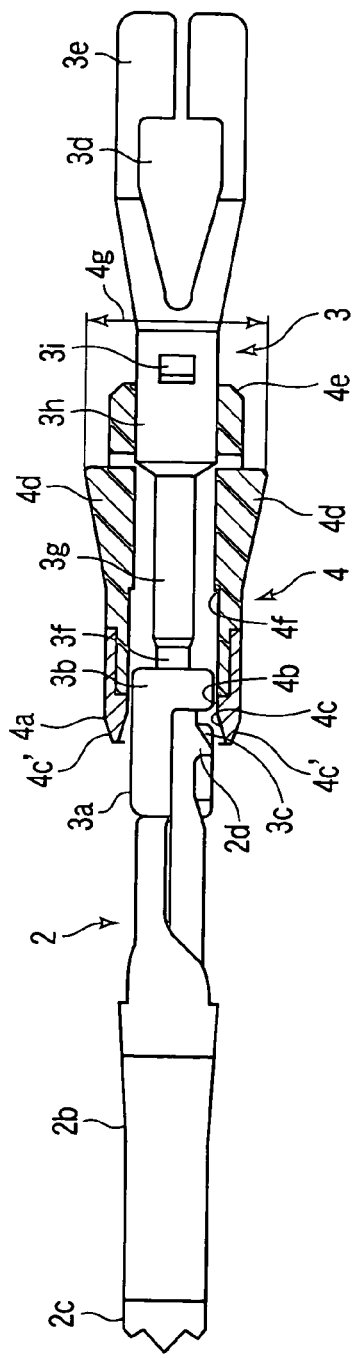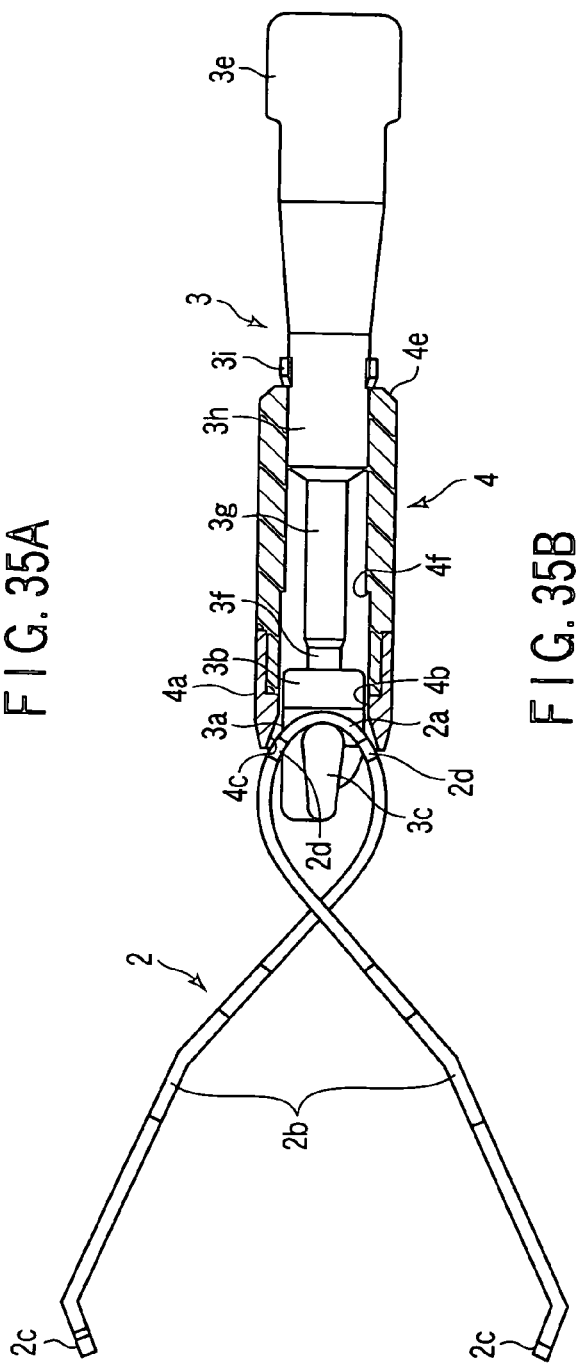
FIG. 35A
FIG. 35B

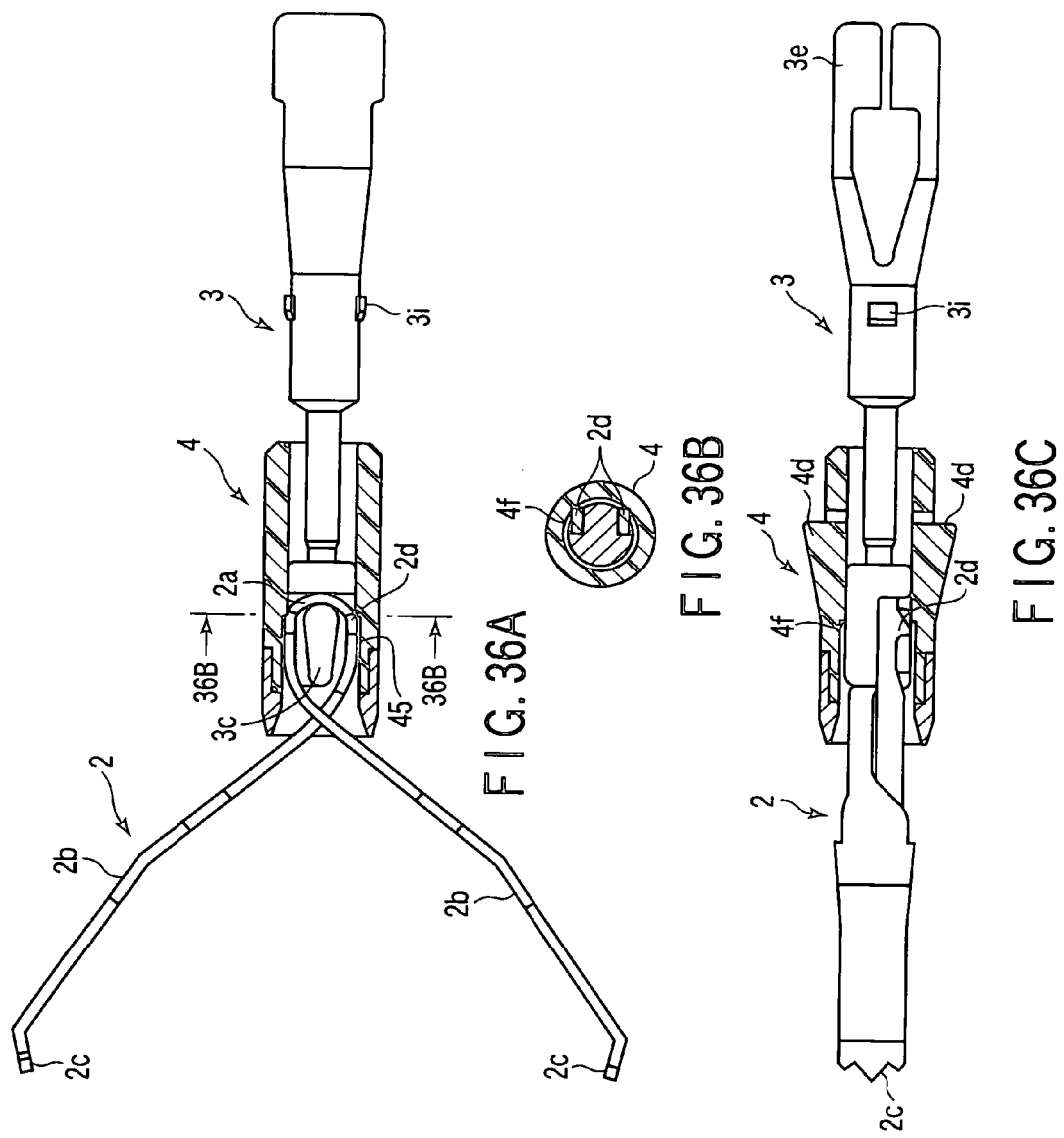

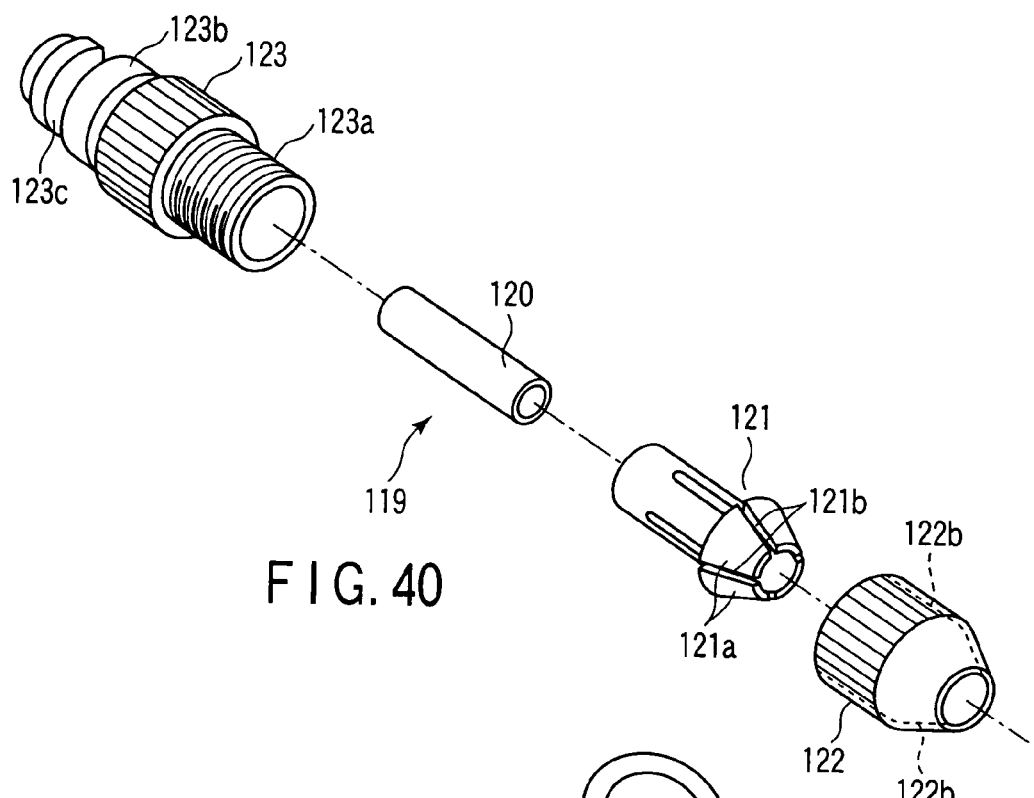
F I G. 40
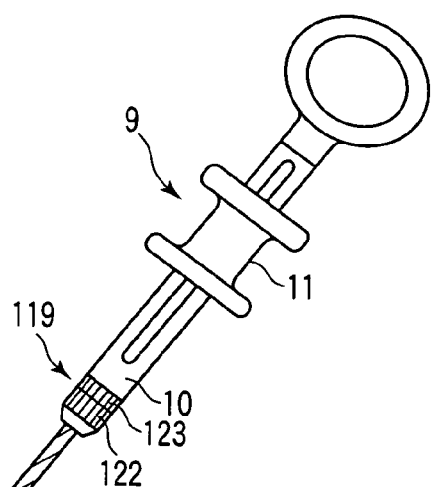
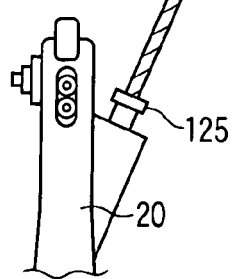
F I G. 41

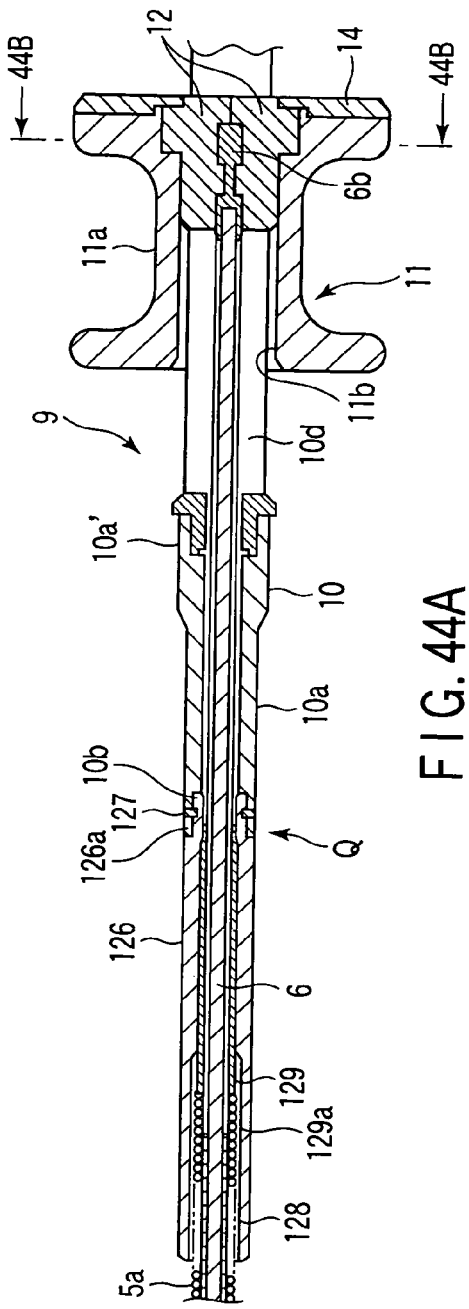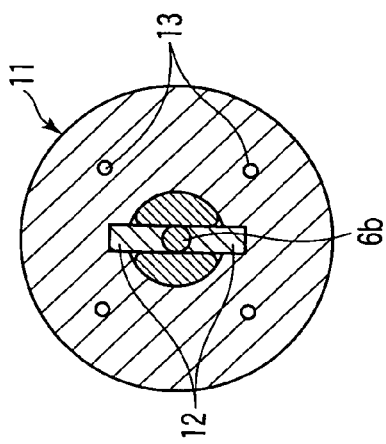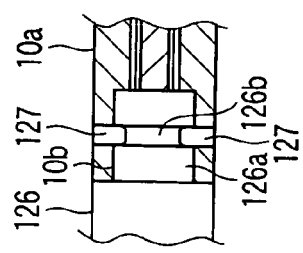
FIG. 44A
FIG. 44B
FIG. 44C

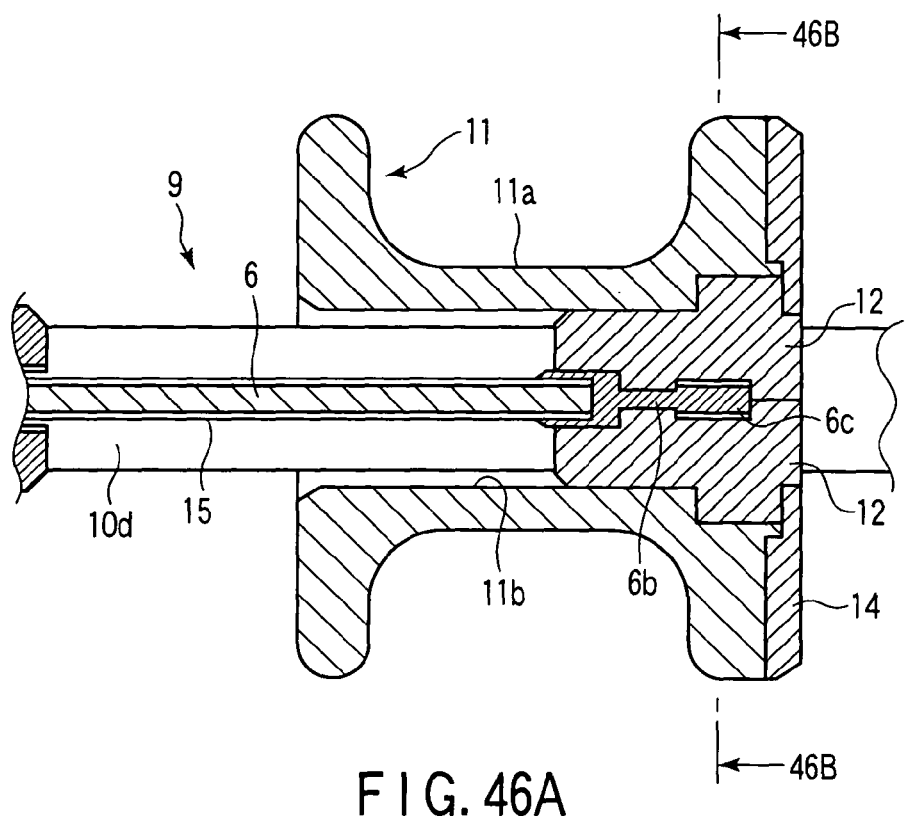
F I G. 46A
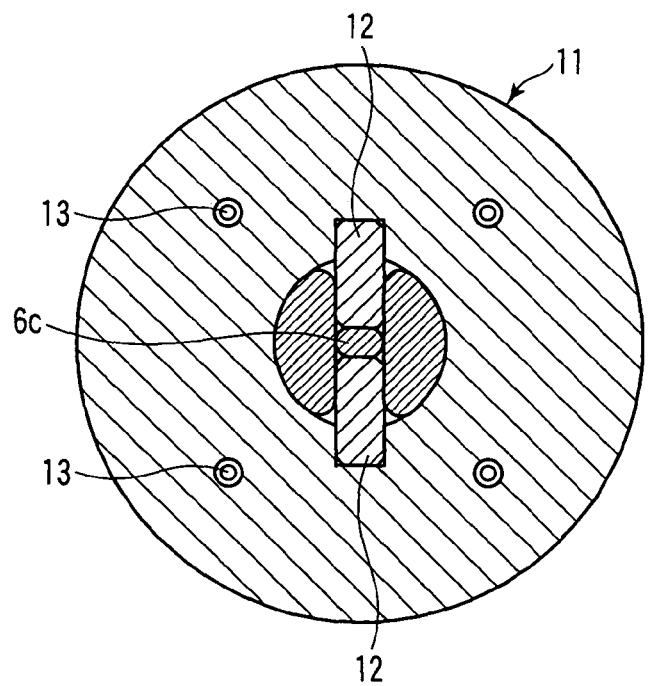
F I G. 46B

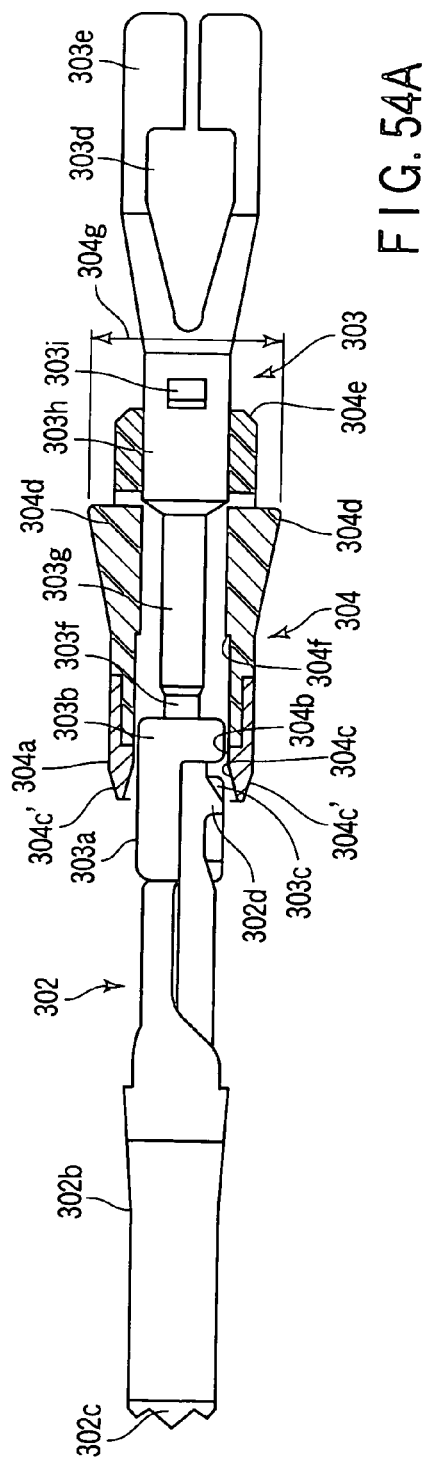
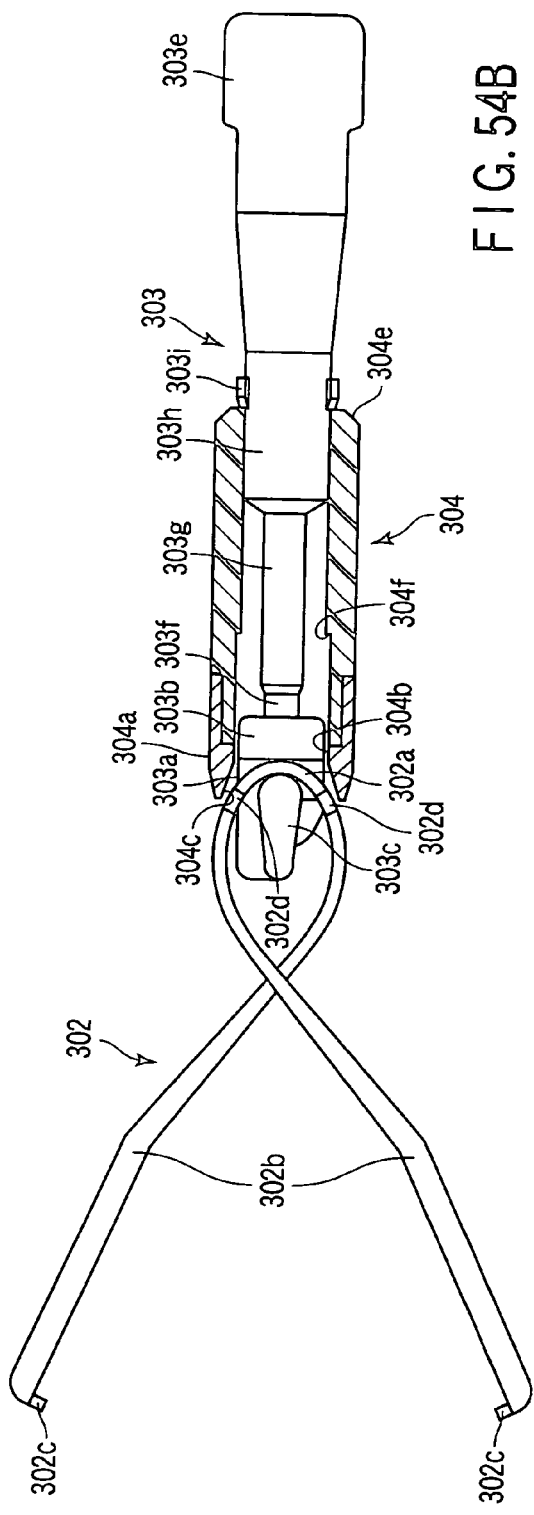
F I G. 54A
F I G. 54B

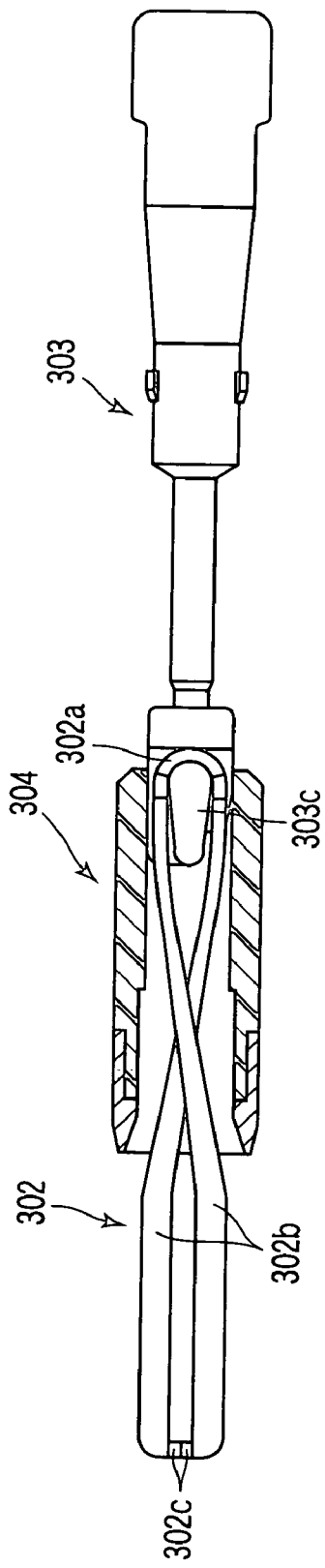
F I G. 56A
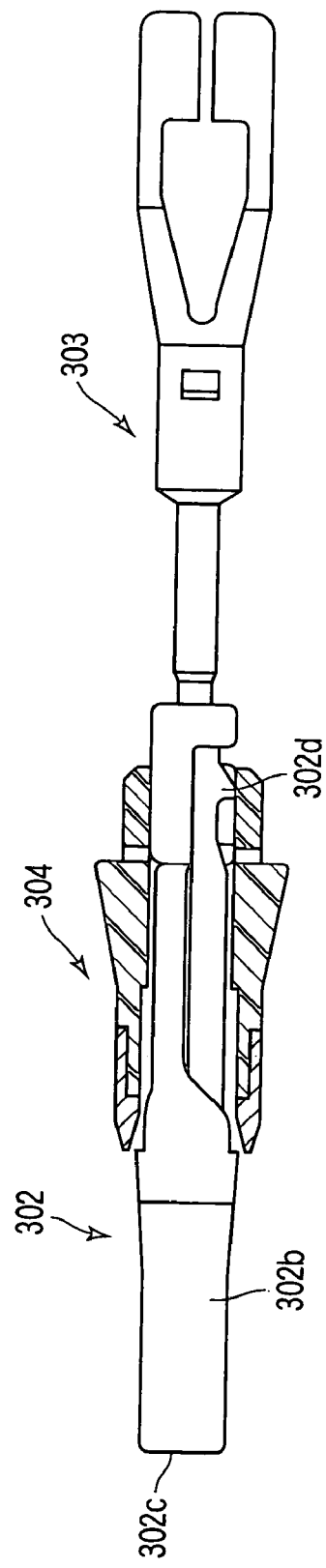
F I G. 56B

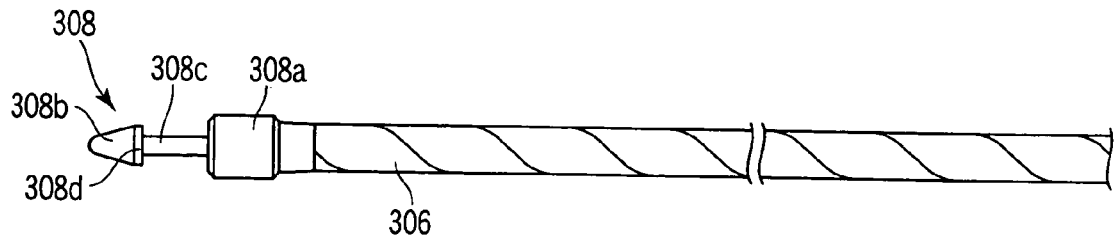
F I G. 57A
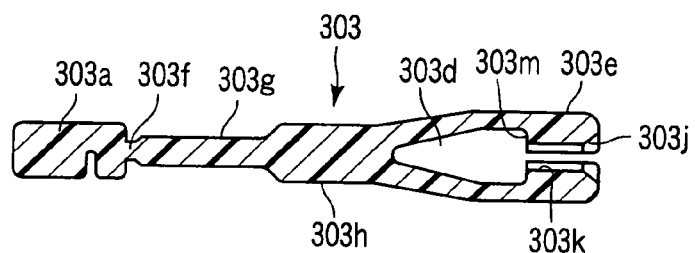
F I G. 57B
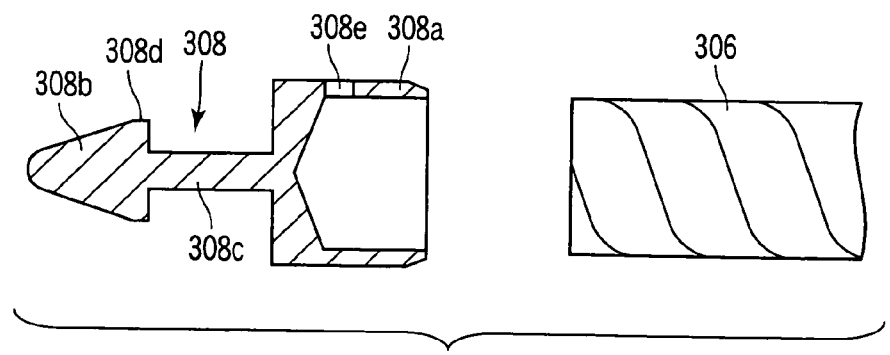
F I G. 57C

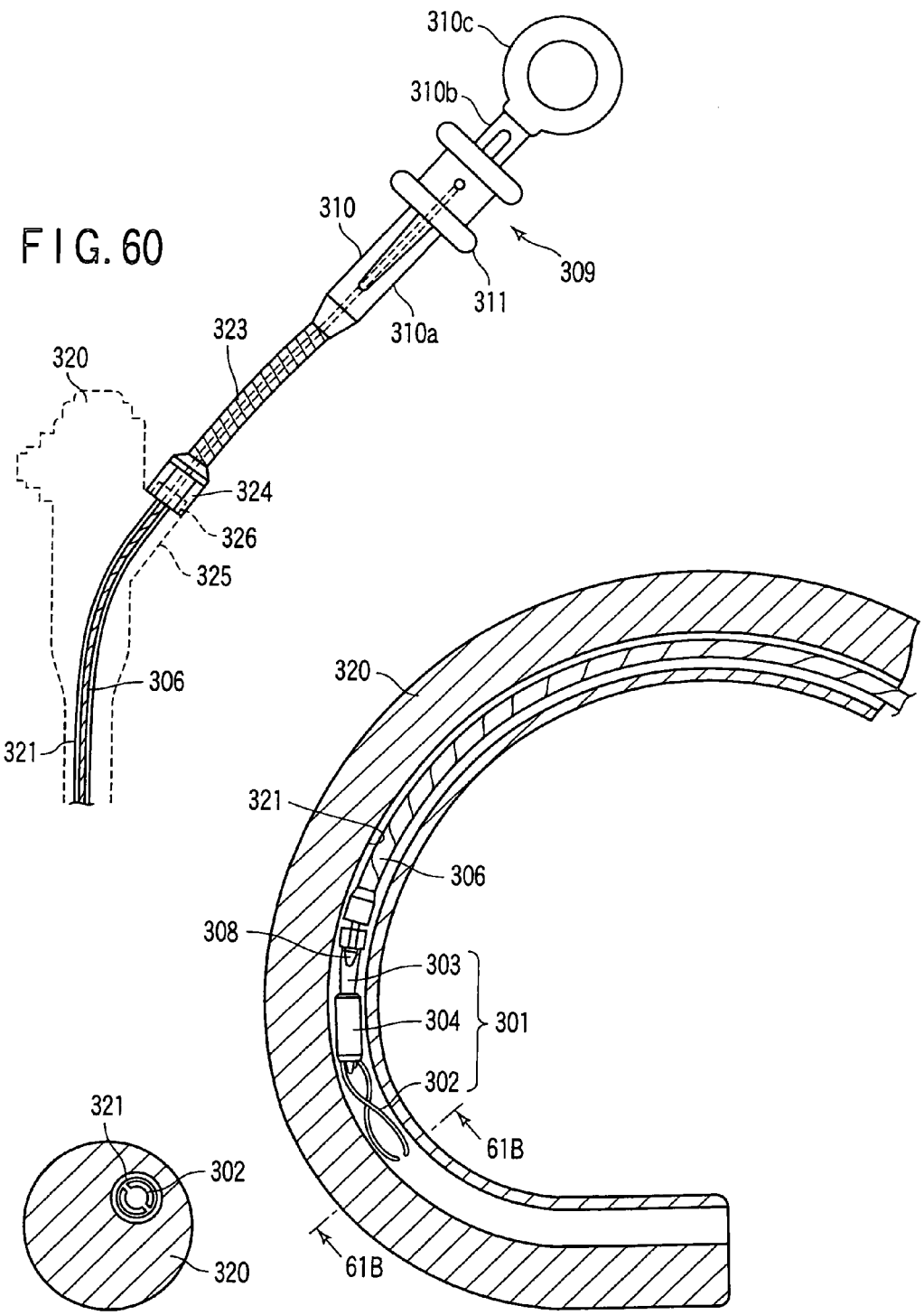

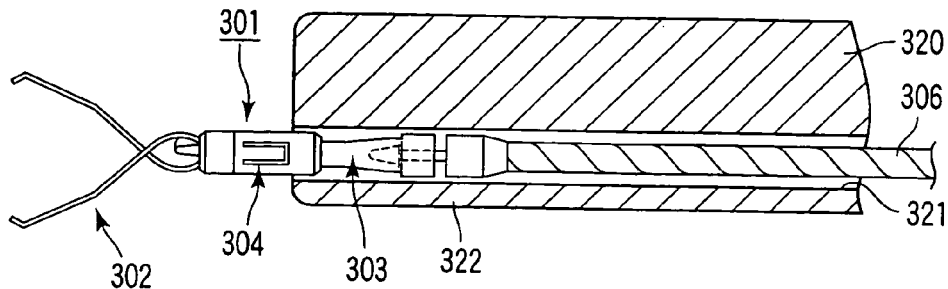
F I G. 64A
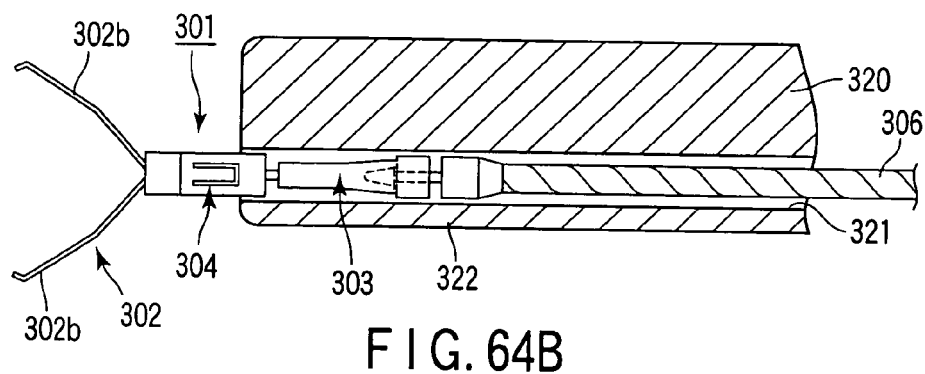
F I G. 64B
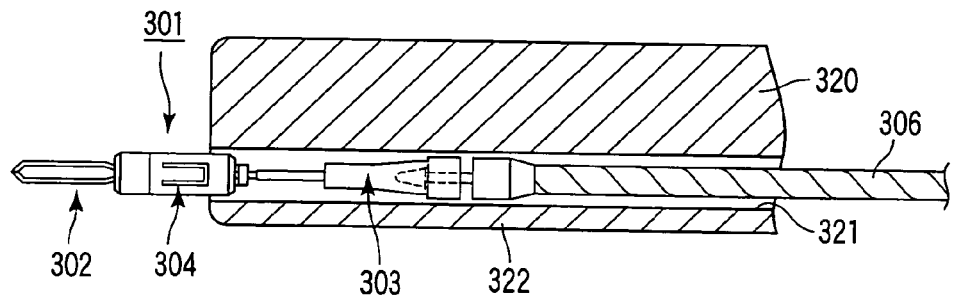
F I G. 64C
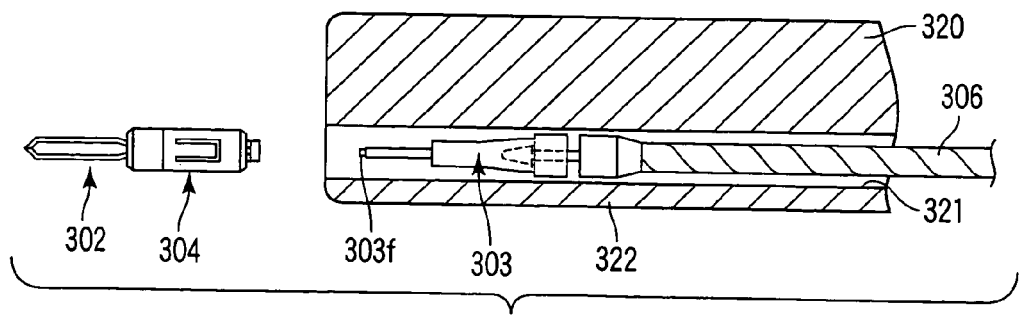
F I G. 64D

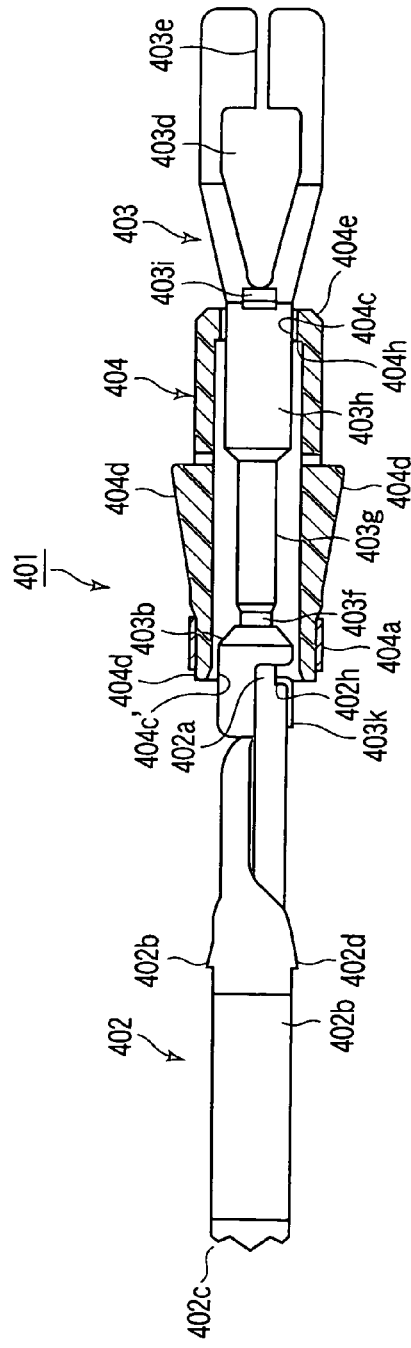
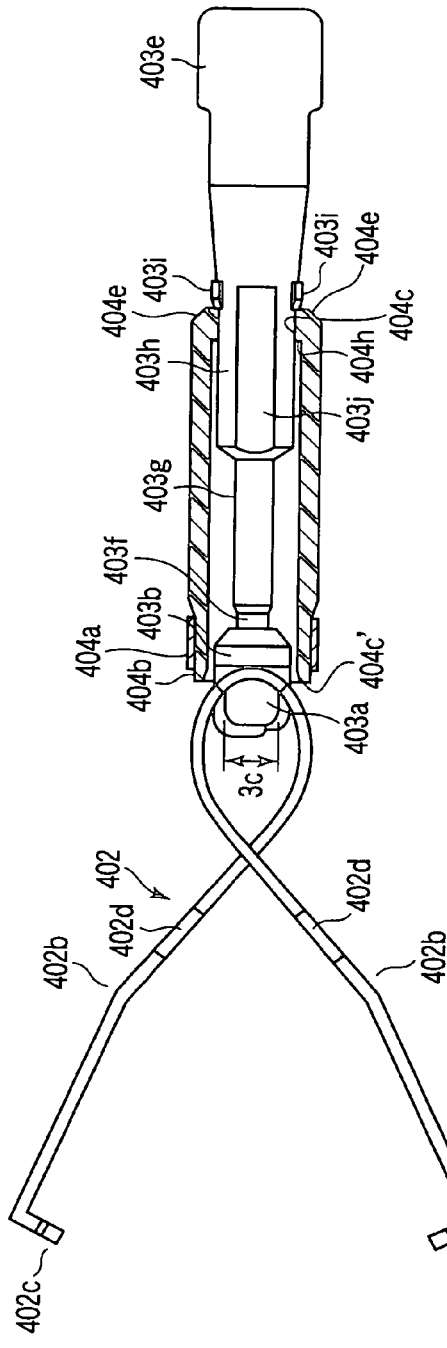
FIG. 70A
FIG. 70B

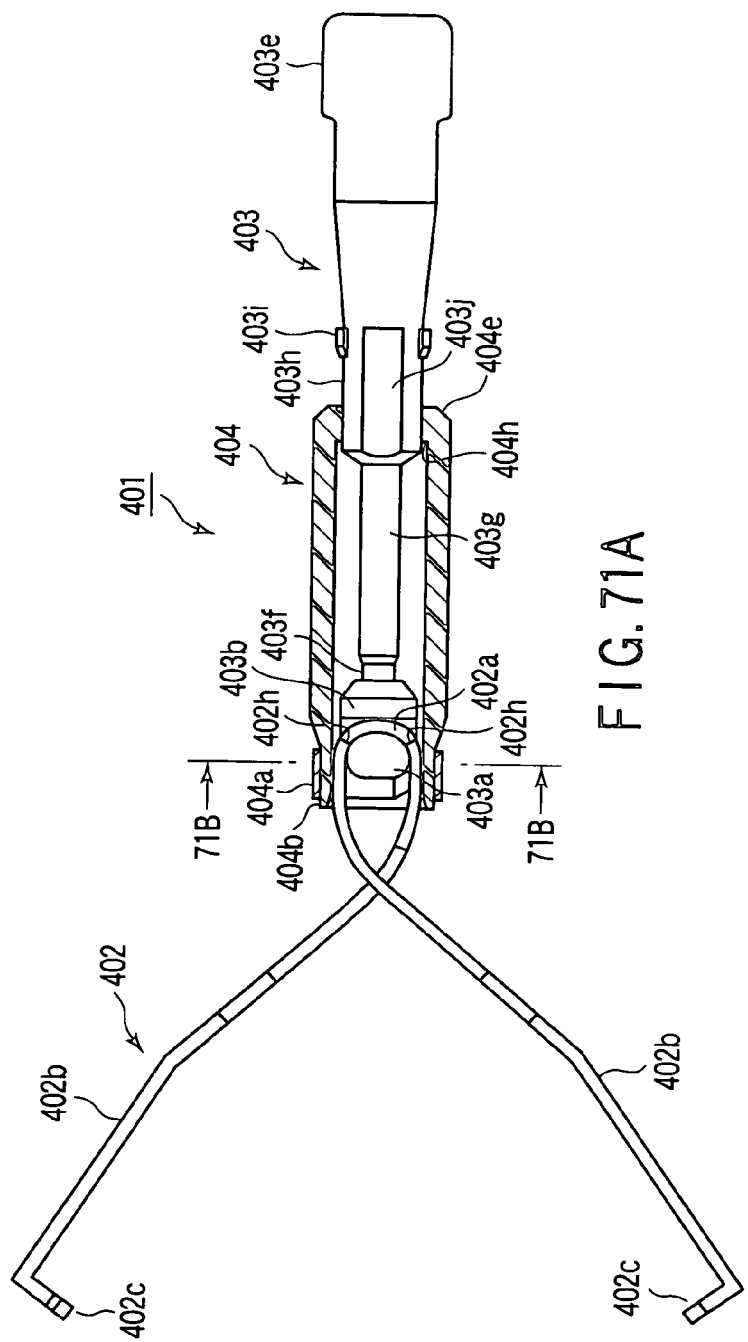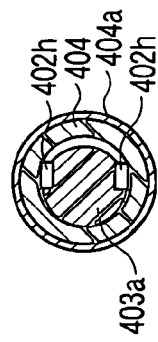
F I G. 71A
F I G. 71B

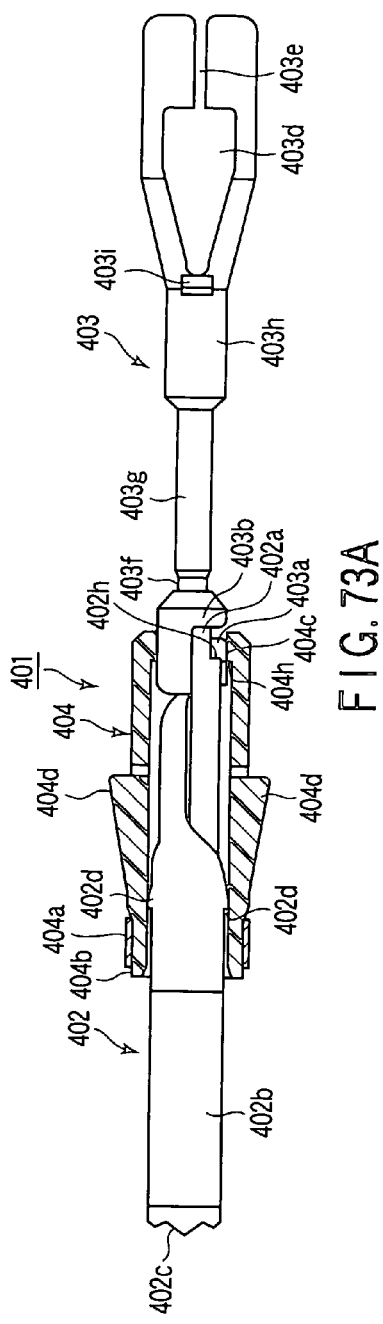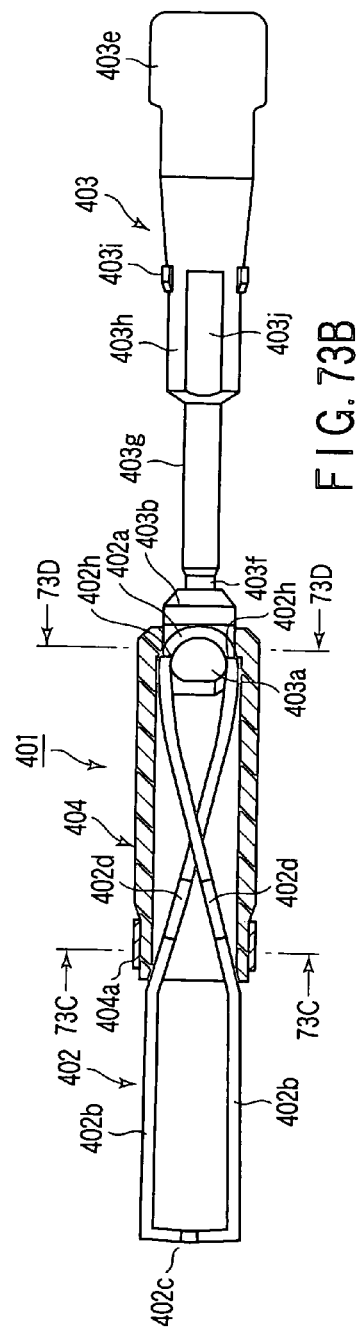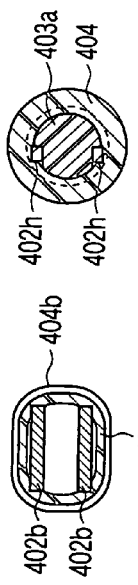
F I G. 73A
F I G. 73B
F I G. 73D
F I G. 73C

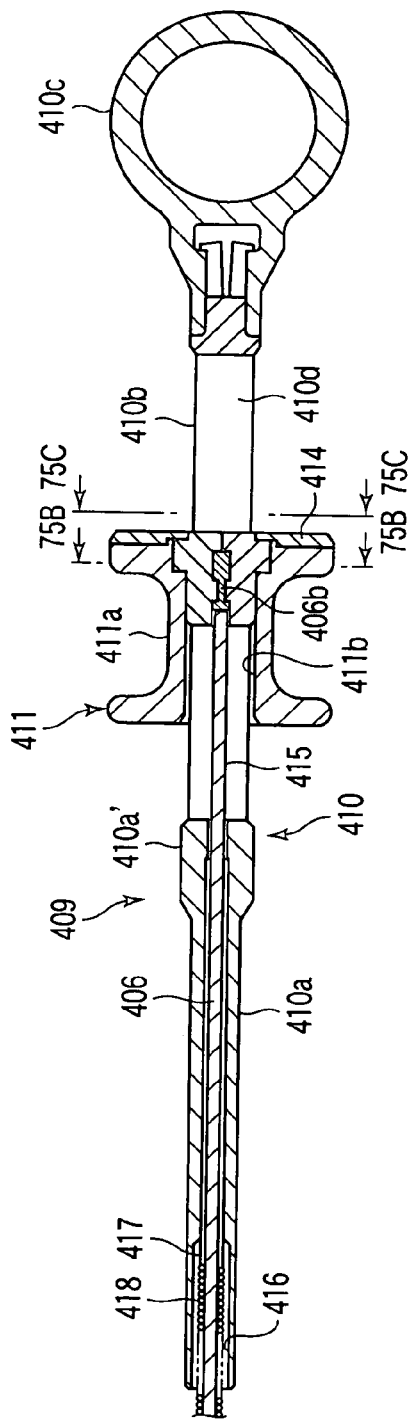
F I G. 75A
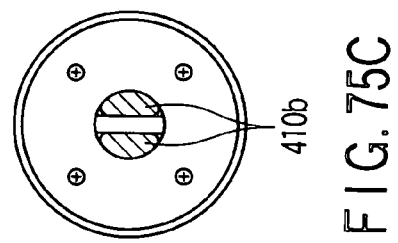
F I G. 75C
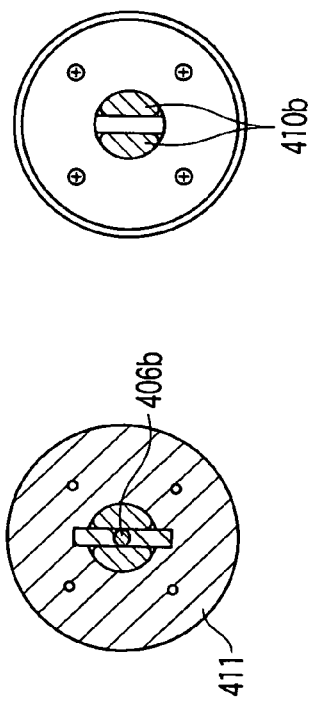
F I G. 75B

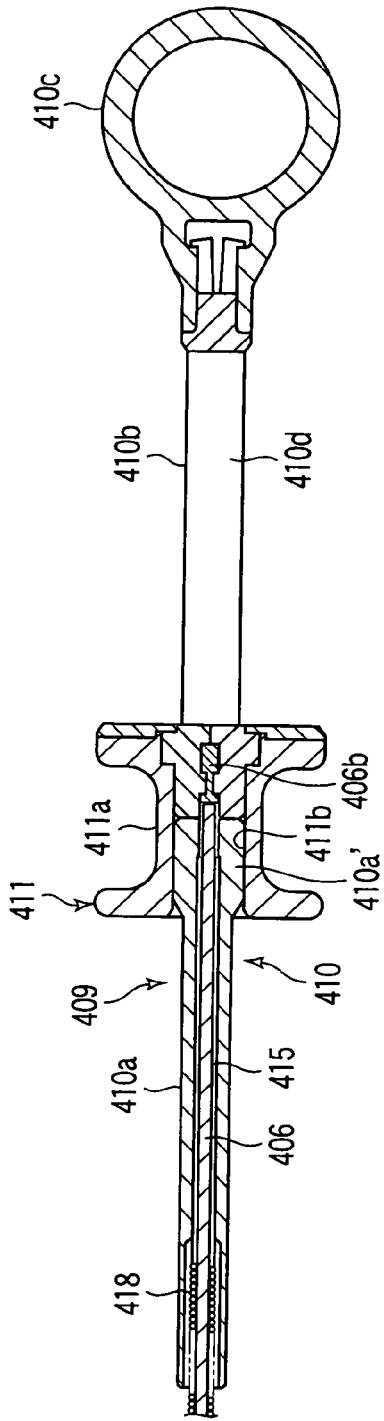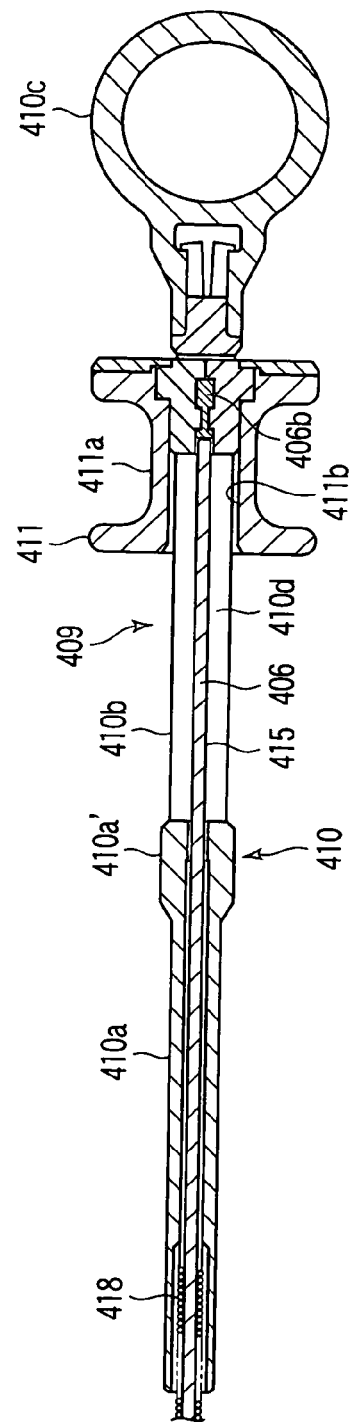
F I G. 76A
F I G. 76B

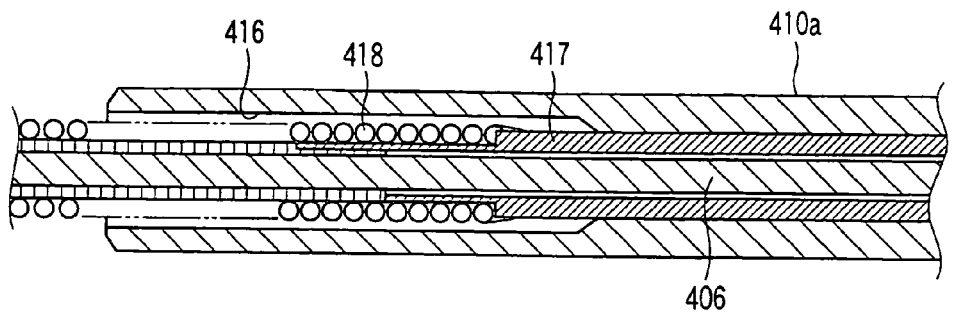
FIG. 77
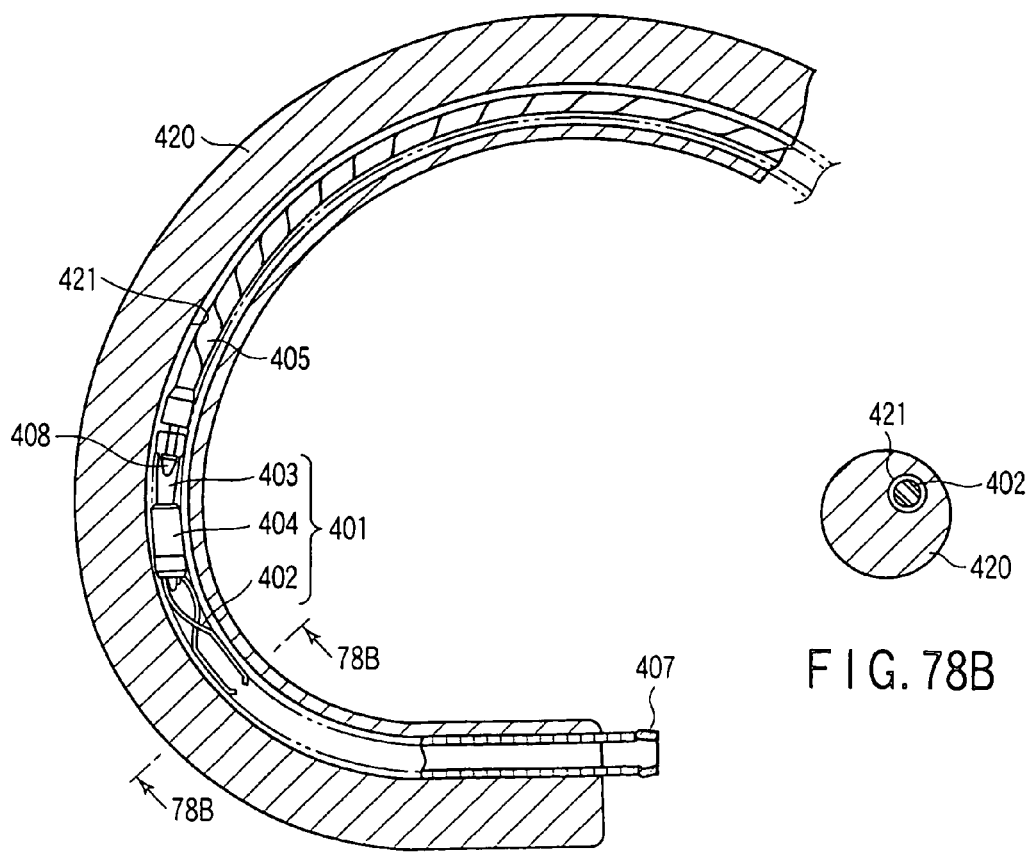
FIG. 78B
FIG. 78A

LIVING TISSUE LIGATION DEVICE

CROSS-REFERENCE TO RELATED APPLICATIONS

This is a Continuation Application of PCT Application No. PCT/JP03/10598, filed Aug. 21, 2003, which was not published under PCT Article 21(2) in English.

This application is based upon and claims the benefit of priority from prior Japanese Patent Applications No. 2002-240673, filed Aug. 21, 2002; No. 2002-288934, filed Oct. 1, 2002; and No. 2002-288935, filed Oct. 1, 2002, the entire contents of all of which are incorporated herein by reference.

BACKGROUND OF THE INVENTION

1. Field of the Invention

The present invention relates to a living tissue ligation device which is endoscopically inserted into a body cavity and ligates living tissue with a clip.

2. Description of the Related Art

As a living tissue ligation device, for example, Jpn. Pat. Appln. KOKAI Publication No. 8-280701 has been known. As a polypectomy snare device, WO 01/10321A1 has been known. Jpn. Pat. Appln. KOKAI Publication No. 8-280701 discloses a device which is designed such that when a clip having a pair of arms which grip living tissue is fitted in a clamping ring, the arms of the clip are closed, and when the clip is made to protrude from the clamping ring, the arms spread apart. The clip and clamping ring can be housed in an introduction tube which is made to extend through a channel of an endoscope. The clip is connected, through a coupling member, to an operating wire which is made to retractably extend through the introduction tube.

According to this device, the clip can be closed and opened by moving the operating wire back and forth using an operator-side operating portion. In addition, the orientation of the clip can be changed by rotating the operating wire using a rotating operating member of the operator-side operating portion. This makes it possible to approach the clip to a target region.

According to the device disclosed in WO 01/10321A1, a snare is provided at a distal end portion of a shaft retractably extending through a sheath. This device comprises a first handle which changes the orientation of the snare by rotating the snare and a second handle which opens/closes the snare.

A patent application for a clip case which houses a clip unit has already been filed as Japanese Patent Application No. 2001-244402. This clip case is molded by a transparent synthetic resin material, and the clip unit is sterilized while being housed in the clip case. The clip case is designed to be connected to the operating wire extending through the introduction tube without being touched with fingers while being housed in the clip case.

For this purpose, the clip case has a clip unit housing portion and introduction tube insertion portion. When the introduction tube is inserted into the clip case through the introduction tube insertion portion, the introduction tube is pressed with elastic restoring force by the elastic press portion provided for the clip case. When the operating wire extending through the introduction tube is moved forward, the arrowhead hook provided at the distal end portion of the operating wire elastically engages with the coupling member of the clip unit.

The devices disclosed in Jpn. Pat. Appln. KOKAI Publication No. 8-280701 and WO 01/10321A1 are structured to change the orientations of the clip and snare by rotating them using the operator-side operating portion. However, this structure is designed to rotate the operating wire, and hence a large torque cannot be obtained, and the structure becomes complicated.

According to the device disclosed in Jpn. Pat. Appln. KOKAI Publication No. 8-280701, even while living tissue is ligated by pulling the clip into the clamping ring and closing the arms of the clip, the clamping ring is only pressing the clip so as to close the arms. Therefore, the gripping force applied to the living tissue may decrease.

The clip case disclosed in Japanese Patent Application No. 2001-244402 is structured to press the introduction tube with the elastic restoring force of the elastic press portion provided for the clip case. This force is insufficient as holding force for the introduction tube. Therefore, the introduction tube is moved to a direction to come off the introduction tube insertion portion of the clip case owing to the reactive force generated when the operating wire is moved forward to elastically engage the arrowhead hook with the coupling member. This makes it impossible to engage the arrowhead hook with the coupling member by one-touch operation.

If the elastic restoring force of the elastic press portion is increased to solve this problem, the insertion force required for the introduction tube also increases. By repeatedly mounting the clip on the introduction tube, an excessive load is placed on the introduction tube. This may induce buckling of the introduction tube.

BRIEF SUMMARY OF THE INVENTION

It is an object of the present invention to provide a living tissue ligation device by which an improvement in the gripped state of living tissue can be expected by allowing a clip to engage with a clamping member when the living tissue is gripped with the clip, and the ability to stop bleeding is improved.

According to one aspect of the present invention, there is provided a living tissue ligation device comprising:

a clip having a plurality of arms which close to grip living tissue;

a clamping member into which the clip is inserted to close the arms of the clip;

a coupling member which is to be inserted into the clamping member and engages with the clip to allow the clip to be inserted into the clamping member; and a lock portion which holds the arms of the clip in a closed state when the clip engages with the clamping member.

The lock portion is preferably provided for at least one of the clip and the clamping member.

Preferably, the lock portion is provided for the clamping member, and the material for the clamping member is softer than that for the clip.

According to another aspect of the present invention, there is provided a living tissue ligation device comprising:

a pair of arms which grip living tissue;

a clamping member which engages with the arms and moves the arms in a direction to close; and a lock member which inhibits the arms from moving in a direction to open, once closing the arms.

The lock member is preferably provided for at least the arms or the clamping member.

According to the device of an embodiment, when the clip is pulled into the clamping member, the arms of the clip are closed by the clamping member, and the living tissue is gripped with the clip. In addition, the clip engages with the clamping member to be held in the closed state. Therefore, the gripping state of the clip is not weakened, and the gripped state of the living tissue can be maintained.

According to the device of another embodiment, when the arms are closed by the clamping member, the living tissue is gripped with the arms, and the arms engage with the clamping member to hold the closed state of the arms. Therefore, the gripping state of the clip is not weakened, and the gripped state of the living tissue can be maintained.

As described above, according to the device of the present invention, when the clip is pulled into the clamping member, the arms of the clip are closed by the clamping member, and the living tissue is gripped with the clip. In addition, the clip engages with the clamping member to be held in the closed state. Therefore, the gripping state of the clip is not weakened, and the gripped state of the living tissue can be maintained.

According to the other embodiments described above, when the arms are closed by the clamping member, the living tissue is gripped with the arms, and the arms engage with the clamping member to hold the closed state of the arms. Therefore, the gripping state of the clip is not weakened, and the gripped state of the living tissue can be maintained.

BRIEF DESCRIPTION OF THE SEVERAL VIEWS OF THE DRAWING

FIG. 4A is a partially cutaway side view showing the clip unit in a state wherein the clip according to the embodiment is open, FIG. 4B is a sectional view taken along a line 4B-4B of FIG. 4A, and FIG. 4C is a partially cutaway plan view of the clip unit;

FIGS. 5A and 5B are a partially cutaway side view and a partially cutaway plan view showing the clip unit in a state wherein the clip according to the embodiment is closed;

FIG. 9A is a partially cutaway side view showing the operating portion of the ligation device according to the embodiment, FIG. 9B is a sectional view taken along a line 9B-9B of FIG. 9A, and FIG. 9C is a sectional view taken along a line 9C-9C of FIG. 9A;

FIGS. 10A and 10B are partially cutaway side views of the operating portion of the ligation device according to the embodiment, showing different states;

FIG. 14A is a plan view of a lower case according to the embodiment, and FIG. 14B is a partially cutaway side view of the clip case;

FIG. 15A is a sectional view taken along a line 15A-15A of FIG. 14A, FIG. 15B is a sectional view taken along a line 15B-15B of FIG. 14B, and FIG. 15C is a sectional view taken along a line 15C-15C of FIG. 14B;

FIG. 18A to 18C are sectional views showing the clip case according to the embodiment in different states to explain the function of the clip case;

FIG. 20 is a sectional view showing the clip case according to the embodiment to explain the function of the clip case;

FIG. 27A is a perspective view of a clip according to the third embodiment of the present invention, FIG. 27B is a perspective view of a loop portion, and FIG. 27C is a sectional view taken along a line 27C-27C of FIG. 27A;

FIG. 29A is a partially cutaway side view showing the clip unit in a state wherein the clip is open according to the embodiment, and FIG. 29B is a sectional view taken along a line 29A-29A;

FIG. 30 is a partially cutaway side view showing the clip unit in a state wherein the clip is open according to the embodiment;

FIG. 31A is a partially cutaway plan view showing a state wherein the clip is closed according to the embodiment, FIG. 31B is a partially cutaway, FIG. 31C is a sectional view taken along a line 31C-31C of FIG. 31B, and FIG. 31D is a sectional view taken along a line 31D-31D of FIG. 31B;

FIG. 32A is a partially cutaway side view showing the clip unit according to the embodiment, and FIG. 32B is a sectional view taken along a line 32B-32B of FIG. 32A;

FIG. 33A is a partially cutaway side view showing a modification of the clip unit according to the embodiment, and FIG. 33B is a sectional view taken along a line 33B-33B of FIG. 33A;

FIG. 34 is a partially cutaway side view showing a modification of the clip according to the embodiment in a state wherein the clip is made to extend through an introduction tube;

FIGS. 35A and 35B are a partially cutaway plan view and a partially cutaway side view of a clip unit according to the fourth embodiment of the present invention;

FIG. 36A is a partially cutaway side view showing the clip unit in a state wherein the clip is open according to the embodiment, FIG. 36B is a sectional view taken along a line 36B-36B of FIG. 36A, and FIG. 36C is a partially cutaway plan view of the unit;

FIG. 40 is an exploded perspective view of a clip rotating operating portion of the device according to the embodiment;

FIG. 41 is a view for explaining the function of the clip rotating operating portion according to the embodiment;

FIG. 44A is a partially cutaway side view of the operating portion according to the embodiment, FIG. 44B is an enlarged sectional view taken along a line 44B-44B of FIG. 44A, and FIG. 44C is an enlarged partially cutaway side view of a portion indicated by R in FIG. 44A;

FIG. 46A is a sectional view of the operating portion of the device according to the embodiment, and 46B is a sectional view taken along a line 46B-46B of FIG. 46A;

FIGS. 54A and 54B are a partially sectional plan view and a partially sectional side view of the clip unit according to the embodiment;

FIGS. 56A and 56B are a partially cutaway plan view and a partially cutaway side view showing a state wherein the clip according to the embodiment is closed;

FIG. 57A is a side view of the distal end portion of a ligation device according to the embodiment, FIG. 57B is a longitudinal sectional side view of a coupling member, and FIG. 57C is a sectional view showing the fixing structure of an arrowhead hook;

FIG. 60 is a view showing the arrangement of the operating portion of the ligation device according to the embodiment;

FIG. 61A is a longitudinal sectional view of the insertion portion of an endoscope according to the embodiment, and FIG. 61B is a sectional view taken along a line 61B-61B of FIG. 61A;

FIGS. 64A to 64D are views for explaining the operation of the device according to the embodiment;

FIGS. 70A and 70B are a partially cutaway plan view and a partially cutaway side view of the clip unit according to the embodiment;

FIG. 71A is a partially cutaway side view showing the clip unit in a state wherein the clip according to the embodiment is open, and FIG. 71B is a sectional view taken along a line 71B-71B of FIG. 71A;

FIGS. 73A and 73B are a partially cutaway plan view and a partially cutaway side view showing a state wherein the clip according to the embodiment is closed, and FIGS. 73C and 73D are respectively a sectional view taken along a line 73C-73C of FIG. 73B and a sectional view taken along a line 73D-73D of FIG. 73B;

FIG. 75A is a partially cutaway side view showing the operating portion of the ligation device according to the embodiment, and FIGS. 75B and 75C are respectively sectional views taken along a line 75B-75B and a line 75C-75C of FIG. 75A;

FIGS. 76A and 76B are partially cutaway side views showing the operating portion of the ligation device according to the embodiment in different states;

FIG. 77 is a longitudinal sectional view of the distal end portion of an operating portion body according to the embodiment;

FIG. 78A is a longitudinal sectional view of the insertion portion of an endoscope according to the embodiment, and FIG. 78B is a sectional view taken along a line 78B-78B of FIG. 78A;

DETAILED DESCRIPTION OF THE INVENTION

The embodiments of the present invention will be described below with reference to the views of the accompanying drawing.

Figure 1:
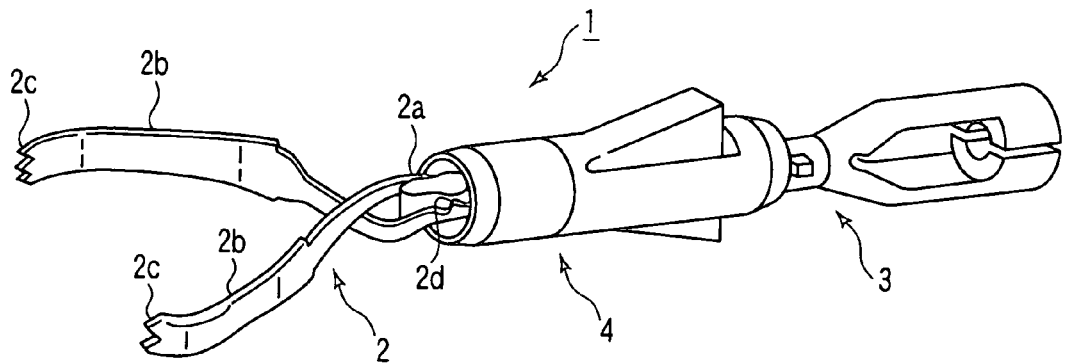
FIG. 1 is a perspective view of a clip unit according to the first embodiment of the present invention.

FIGS. 1 to 23 are associated with the first embodiment. FIG. 1 is a perspective view of a clip unit 1 of a living tissue ligation device. The clip unit 1 is comprised of a clip 2, a coupling member 3, and a press tube 4 serving as a fastening member.

Figure 2A:
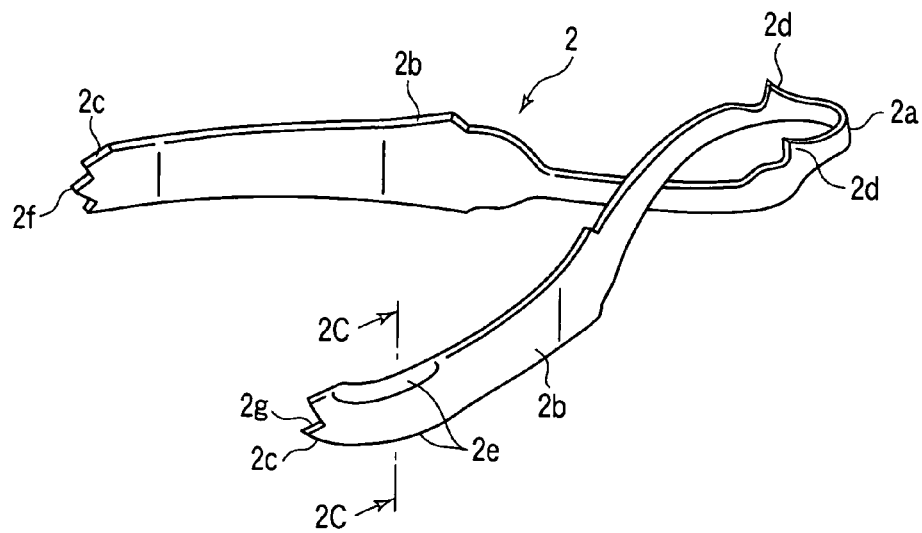
FIG. 2A is a perspective view of a clip according to the embodiment.
Figure 2B:
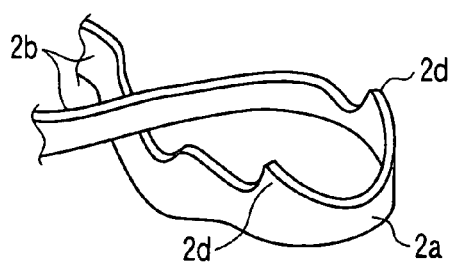
FIG. 2B is a perspective view of the loop portion of the clip.
Figure 2C:
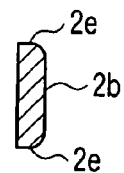
FIG. 2C is a sectional view taken along a line 2C-2C of FIG. 2A.

As shown in FIGS. 2A to 2C, the clip 2 is formed such that after a loop portion 2a is formed by bending a metal plate member such as a leaf spring member made of stainless steel or the like at its middle portion, a pair of arms 2b having a property of spreading apart are made to intersect at a position near the loop portion 2a and extend with their distal end portions being spaced apart from each other. Tissue gripping portions 2c are formed on the distal end portions of the arms so as to face each other.

That portion of the metal plate member which corresponds to the intersecting portion of the arms 2b of the clip 2 is formed to have a width smaller than that of the distal end portions, thereby preventing the intersecting portion from becoming wide. Sawtooth-like projections 2d protruding in the widthwise direction of the plate member are provided on the upper edges of those portions of the respective arms 2b which are located near the loop portion 2a. Each projection 2d is formed to have an inclined surface with an acute angle on the tissue grip portion side and an obtuse angle on the loop portion side such that the projection slidably moves on the inner surface of the press tube 4 in the direction in which the clip 2 is pulled into the press tube 4 and bites into the inner surface of the press tube 4 in the direction opposite to the pulling direction.

Both side edge portions 2e of that portion of each arm 2b which is near the distal end portion are chamfered or rounded by 0.05 mm or more to allow the arm 2b to easily slide on the inner surface of an introduction tube (to be described later). Each tissue gripping portion 2c is bent inward at an angle of about 90° to 150° (an angle θ in FIG. 3B). One tissue gripping portion 2c is formed into an almost triangular convex portion 2f, whereas the other tissue gripping portion 2c is formed into an almost triangular concave portion 2g so as to engage with the convex portion 2f.

The dimensions of the clip 1 will be described next. The size of the clip is set in consideration of gripping ability for the living tissue and insertion into an endoscope. For example, the clip has a thickness of 0.1 mm to 0.5 mm and a total length of 5 mm to 10 mm. When the loop portion 2a is elliptic, it has a major axis length of 1 mm to 5 mm and a minor axis length of 1 mm to 5 mm. If the loop portion is circular, its diameter is 1 mm to 5 mm. Each tissue gripping portion 2c has a length of about 1 mm and a width of about 1 mm to 2 mm. The width and thickness of each projection 2d are set to allow the projection 2d to be pulled into the press tube 4 and a distal end tube (to be described later).

Figure 3A:
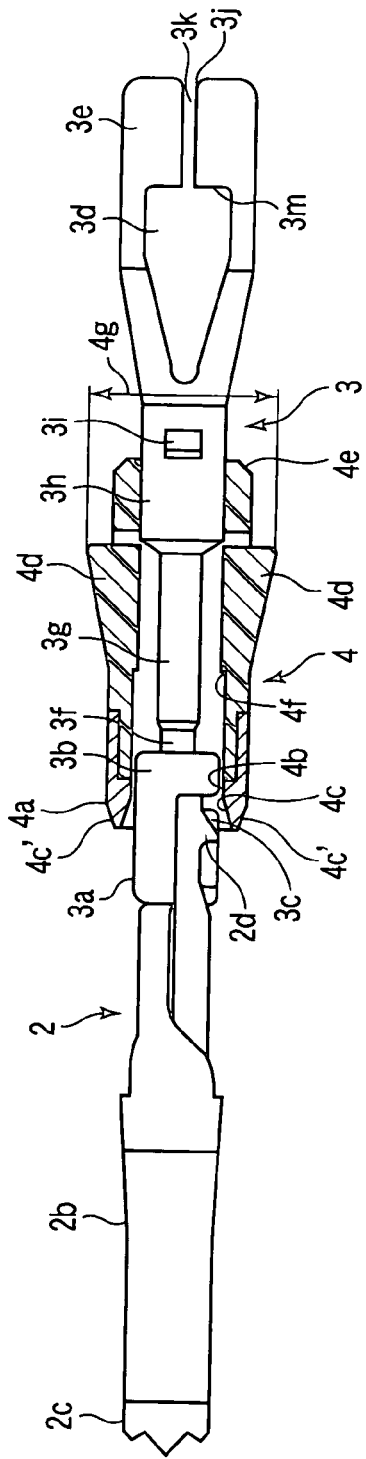
FIG. 3A is a partially cutaway plan view of the clip unit according to the embodiment.
Figure 3B:
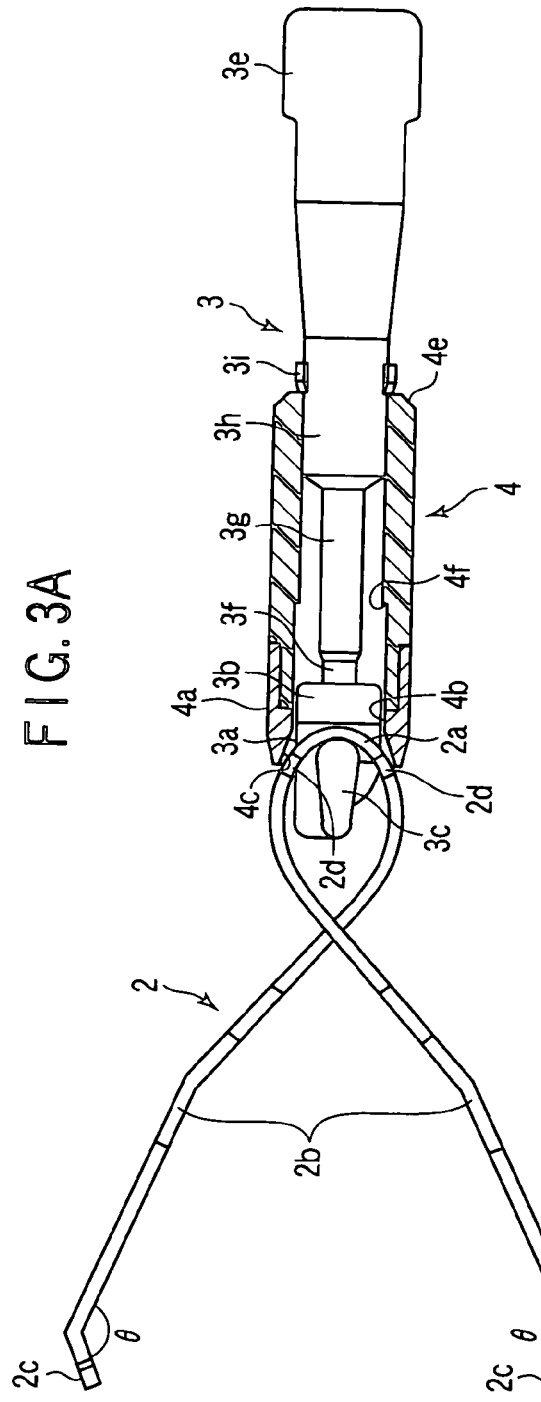
FIG. 3B is a partially cutaway side view of the clip unit.

As shown in FIGS. 3A and 3B, the coupling member 3 is manufactured by injection-molding a high-strength resin material such as a liquid crystal polymer or nylon, and has a cylindrical, rodlike shape. A protruding portion 3a is provided on the distal end portion of the coupling member. A proximal portion 3b of the protruding portion 3a has an almost disk-like shape. A flat, elliptic projection portion 3c which is long in the axial direction is formed on that portion of the protruding portion 3a which is located closer to the distal end than the proximal portion 3b. The loop portion 2a of the clip 2 is hooked on the projection portion 3c to engage the clip 2 with the coupling member 3.

The other end portion of the coupling member 3 is bifurcated, and a gripping portion 3e which has a notched portion 3d including a slit portion extending from the proximal portion of the coupling member 3 and is used to grip an arrowhead hook (to be described later) is formed at the bifurcated portion. The intermediate portion of the coupling member 3 is formed into a small-diameter portion 3f serving as a fracture portion, an intermediate-diameter portion 3g, and a large-diameter portion 3h which extends from the distal end side to the proximal end side. The dimensions of small-diameter portion 3f are so set as to fracture when a fracturing force of 20 N to 60 N is applied thereto. The outer diameter of the large-diameter portion 3h is set such that it tightly fits on the inner circumferential surface of the press tube 4. Lock projections 3i are provided on portions of the outer circumferential surface of the large-diameter portion 3h.

The dimensions of the coupling member 3 will be described. The total length of the coupling member 3 is about 10 mm. The projection portion 3c has a height of 0.2 mm or more and a width of 0.2 mm or more. The inner diameter of the gripping portion 3e is about 0.6 mm. The outer diameter of the large-diameter portion 3h is 1 mm to 1.3 mm. The height of each lock projection 3i is set to 0.1 mm or more.

The press tube 4 is formed by injection-molding a material softer than the clip 2, for example, a high-rigidity resin having appropriate elasticity such as PPA (polyphthalamide) or PA (polyamide). The press tube 4 closes the arms 2b of the clip 2 when the clip 2 is inserted and mounted therein such that the inner surfaces of the arms 2b come into contact with each other.

A distal end tube 4a made of a high-strength metal such as stainless steel is fitted on the distal end portion of the press tube 4. The outer diameter of the distal end tube 4a is equal to that of the press tube 4. An inclined surface 4c is formed on the inner circumferential surface of the distal end tube 4a so as to gradually increase the inner diameter of the distal end tube 4a from a smallest-diameter portion 4b at the proximal end portion to the distal end portion. The outer circumferential surface of the distal end portion of the distal end tube 4a is formed into an inclined surface 4c' so as to gradually reduce the outer diameter of the distal end portion, thereby allowing the distal end tube 4a to smoothly slide on the inner portion of the introduction tube.

A pair of retractable wings 4d which are elastically retractable in the radial direction are provided on the outer circumferential portion of the press tube 4 at an angular interval of 180°. In addition, a rear end inclined surface 4e is provided on the rear end edge portion of the press tube 4. The inner diameter of the distal end side of the press tube 4 is slightly larger than that of the rear end side so as to form an inner-diameter stepped portion 4f therebetween.

The dimensions of the press tube 4 will be described. The total length and inner and outer diameters of the press tube 4 are set in accordance with the size of the clip 2. The inclined surface 4c has an angle of 15 to 90° and an entrance diameter of about 1.6 mm, which are suitable for allowing the clip 2 to grip the tissue. The outside inclined surface 4c' has an angle of 5 to 120°, and is designed to come into surface contact with the bent introduction tube. The retractable wings 4d are almost triangular and have a maximum protrusion width 4g of 2 mm, which is equal to or more than the inner diameter of the introduction tube.

A level difference @ between rear end inclined surface 4e of the press tube 4 and the large-diameter portion 3h of the coupling member 3 is set to 5 mm or less, and the height of the inner-diameter stepped portion 4f is set to 0.1 mm or more.

The assembly of the clip unit 1 will be described next. As shown in FIGS. 3A and 3B, the coupling member 3 is inserted from the rear end side of the press tube 4, and the projection portion 3c of the coupling member 3 is made to protrude from the distal end tube 4a of the press tube 4. In this state, the loop portion 2a of the clip 2 is hooked on the projection portion 3c to engage the clip 2 with the coupling member 3. The coupling member 3 is then pulled to the operator side to make the loop portion 2a of the clip 2 come into contact with the inclined surface 4c of the distal end tube 4a of the press tube 4. At this time, the lock projections 3i of the coupling member 3 engage with the rear end face of the press tube 4. As a consequence, the clip 2, coupling member 3, and the press tube 4 are set in an engaged state, thus completing the assembly, as shown in FIGS. 3A and 3B.

When the coupling member 3 is pulled to the operator side in this state, the loop portion 2a of the clip 2 is pulled into the press tube 4 from the distal end tube 4a of the press tube 4. As a result, the loop portion 2a of the clip 2 is flattened to open the arms 2b.

When the coupling member 3 is further pulled to the operator side, as shown in FIGS. 4A to 4C, the projections 2d of the clip 2 come into contact with the inner-diameter stepped portion 4f of the press tube 4 to lightly block the clip 2 from being further pulled into the press tube 4, thereby holding the arms 2b in the maximum open state.

When the coupling member 3 is further pulled to the operator side, the projections 2d of the clip 2 move over the inner-diameter stepped portion 4f of the press tube 4, and the clip 2 is pulled into the press tube 4. As this pulling operation proceeds, the upper and lower end edges of the outside surfaces of the arms 2b come into slidable contact with the inner circumferential surface of the distal end tube 4a of the press tube 4, and hence the arms 2b of the clip 2 close, as shown in FIGS. 5A and 5B.

At this time, since the press tube 4 is made of a resin having appropriate elasticity which is softer than the clip 2, the projections 2d of the clip 2 bite into the inner wall of the press tube 4. This restricts the clip 2 from moving into the press tube 4 in the axial direction and maintains the closed state. Since the projections 2d of the clip 2 are formed into sawtooth-like shapes protruding in the widthwise direction of the loop portion 2a, the clip 2 can slightly move to the clamping side (the direction to close the arms 2b), but cannot move to the return side (the direction to open the arms 2b) because the projections 2d bite into the inner wall of the press tube 4.

An introduction tube 5 and operating wire 6 shown in FIGS. 6A, 6B, and 6C will be described next. The introduction tube 5 is comprised of an operator-side coil 5a having flexibility which is formed by tightly winding a spring material such as stainless steel, and a distal end coil 5b having flexibility which is connected to the distal end portion of the operator-side coil 5a and formed by tightly winding a spring material such as stainless steel.

The operator-side coil 5a has an outer diameter that allows it to extend through the channel of an endoscope, for example, 2 mm to 6 mm, and an inner diameter that allows the operating wire 6 to extend through the operator-side coil 5a. The operator-side coil 5a has a thickness of about 0.25 to 0.7 mm. The distal end coil 5b has an outer diameter that allows it to extend through the channel of the endoscope, for example, 2 mm to 6 mm, and an inner diameter that allows the clip unit 1 and operating wire 6 to extend through the distal end coil 5b. The distal end coil 5b has a thickness of about 0.25 to 0.7 mm. In addition, a thin portion 5c is formed near the distal end of the distal end coil 5b by a post-process such as grinding. The thin portion 5c has a length of about 1 mm to 10 mm and a thickness of about 0.2 mm to 0.65 mm.

Providing the thin portion 5c near the distal end of the distal end coil 5b increases the flexibility and improves the insertibility and removability with respect to the channel of the endoscope. The distal end coil 5b has undergone a heat treatment. After the heat treatment, the distal end coil 5b is grounded to form the thin portion 5c. Consequently, the thin portion 5c has a glossy metal surface distinctive from the remaining portions, and hence provides a marking effect. Therefore, when the distal end coil 5b protrudes from the distal end portion of the endoscope, the operator can check the protrusion amount with the endoscope.

A distal end chip 7 made of a metal such as stainless steel is provided at the distal end portion of the distal end coil 5b. The distal end chip 7 has an outer diameter that allows it to extend through the channel of the endoscope, for example, 2 mm to 6 mm, and an inner diameter that allows the clip unit 1 or operating wire 6 to extend through the distal end coil 5b, e.g., 2 mm or more. A chip inclined surface 7a having an angle of 5° to 90° is formed on the outer circumferential surface of the distal end chip 7 so as to gradually reduce the diameter.

The operating wire 6 is formed by using a stranded wire comprised of core and side strands of metal wires having appropriate elasticity, e.g., stainless steal or NiTi. If, for example, the inner diameter of the introduction tube 5 is about 2 mm, the operating wire 6 has an outer diameter of 1.2 mm to 1.8 mm to have a clearance of 0.4 mm or less between itself and the inner diameter of the distal end coil 5b. In addition, a Teflon (registered trademark) coat is formed on the outer surface of the operating wire 6. Reducing the clearance between the distal end coil 5b and the operator-side coil 5a to 0.4 mm or less by thickening the operating wire 6 makes it possible to restrict the displacement of the operator-side coil 5a and distal end coil 5b, thereby preventing the operator-side coil 5a and distal end coil 5b from deforming and buckling.

Setting a small clearance as described above can reduce the deformation of the operating wire 6 when it is pushed to the distal end side, and hence can efficiently transmit the pushing force. The surface of the operating wire 6 is covered with a Teflon (registered trademark) coat to reduce the sliding resistance with the introduction tube 5.

A cylindrical wire fixing portion 8a made of a metal material such as stainless steel is fitted on the distal end portion of the operating wire 6. An arrowhead hook 8 is integrally provided with the wire fixing portion 8a through a shaft portion 8c. A fixing hole 8e is formed in the wire fixing portion 8a. The wire fixing portion 8a is fixed to the operating wire 6 by pouring a brazing material into the fixing hole 8e.

The arrowhead hook 8 has an arrowhead inclined portion 8b having a conical shape and an angle of 10° to 120°. An arrowhead large-diameter portion 8d has a diameter of about 0.8 mm to 1.2 mm. The diameter of the shaft portion 8c is about 0.6 mm. The arrowhead hook 8 has an almost vertical push surface 8f, which allows efficient application of force when the clip unit is made to protrude from the introduction tube 5.

Figure 7A:
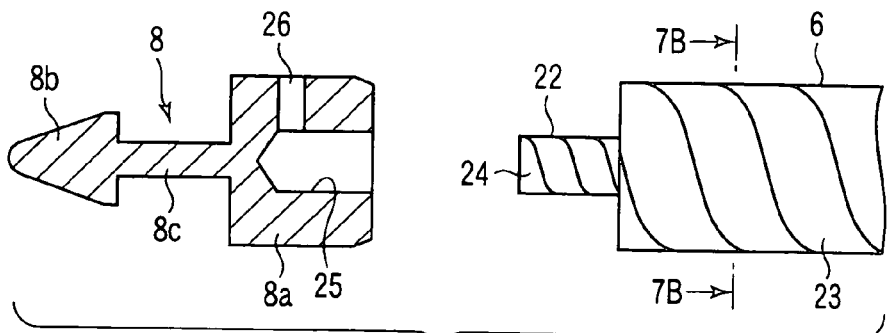
FIG. 7A is a sectional view showing the fixing structure of the arrowhead hook according to a modification to the embodiment.
Figure 7B:
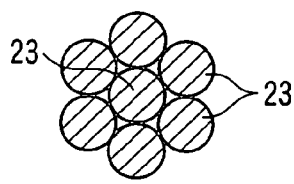
FIG. 7B is a sectional view taken along a line 7B-7B of FIG. 7A.

FIGS. 7A and 7B show a modification of the fixing structure of the arrowhead hook 8 provided at the distal end portion of the operating wire 6. The operating wire 6 is formed from a stranded wire comprised of one core strand 22 and a plurality of side strands 23. The single core strand 22 is made to protrude from the end faces of the side strands 23 to form a protruding portion 24.

An insertion hole 25 in which the protruding portion 24 is inserted and a fixing hole 26 perpendicular to the insertion hole 25 are formed in the wire fixing portion 8a of the arrowhead hook 8. The arrowhead hook 8 is fixed to the operating wire 6 by pouring a brazing material into the fixing hole 26 while the protruding portion 24 is inserted in the insertion hole 25. According to this modification, the operating wire 6 and wire fixing portion 8a can be formed to have the same outer diameter to eliminate the level difference in the first embodiment. This makes it possible to operate the operating wire 6 in the introduction tube 5 more smoothly.

Figure 6A:
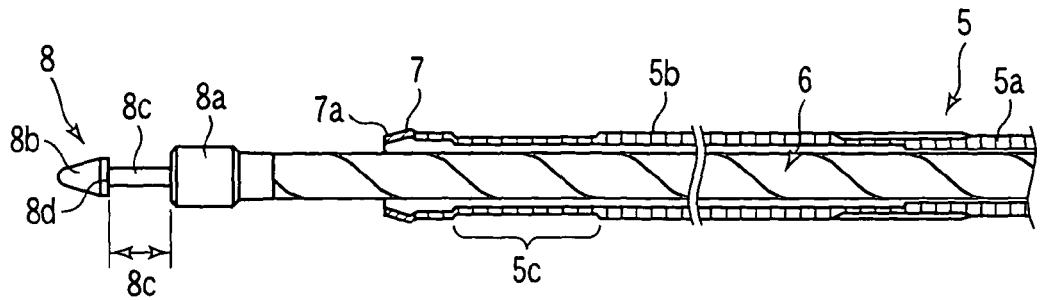
FIG. 6A is a partially cutaway side view of the distal end portion of a ligation device according to the embodiment.
Figures 8A, 8B:
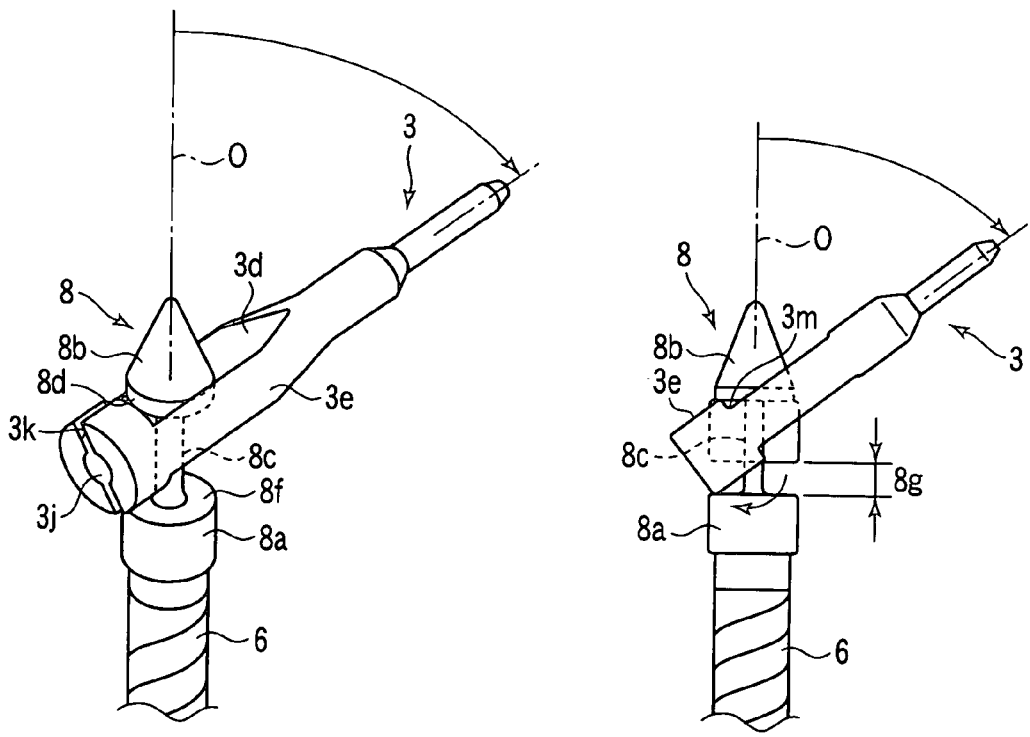
FIGS. 8A and 8B are perspective views showing a state wherein the coupling member is removed from the arrowhead hook according to the embodiment.
Figure 11:
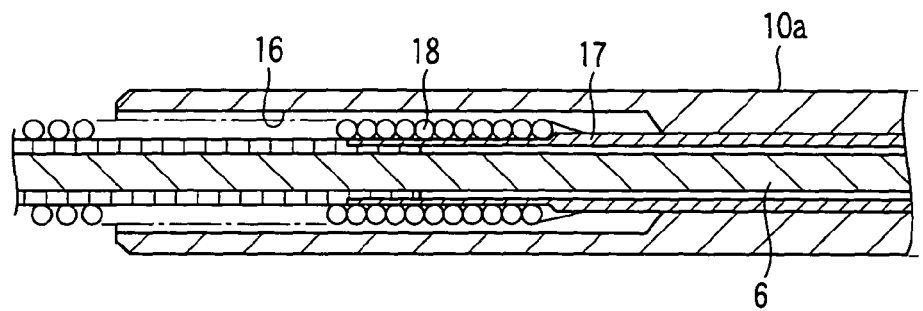
FIG. 11 is a partially cutaway side view of the distal end portion of an operating portion body according to the embodiment.
Figure 12:
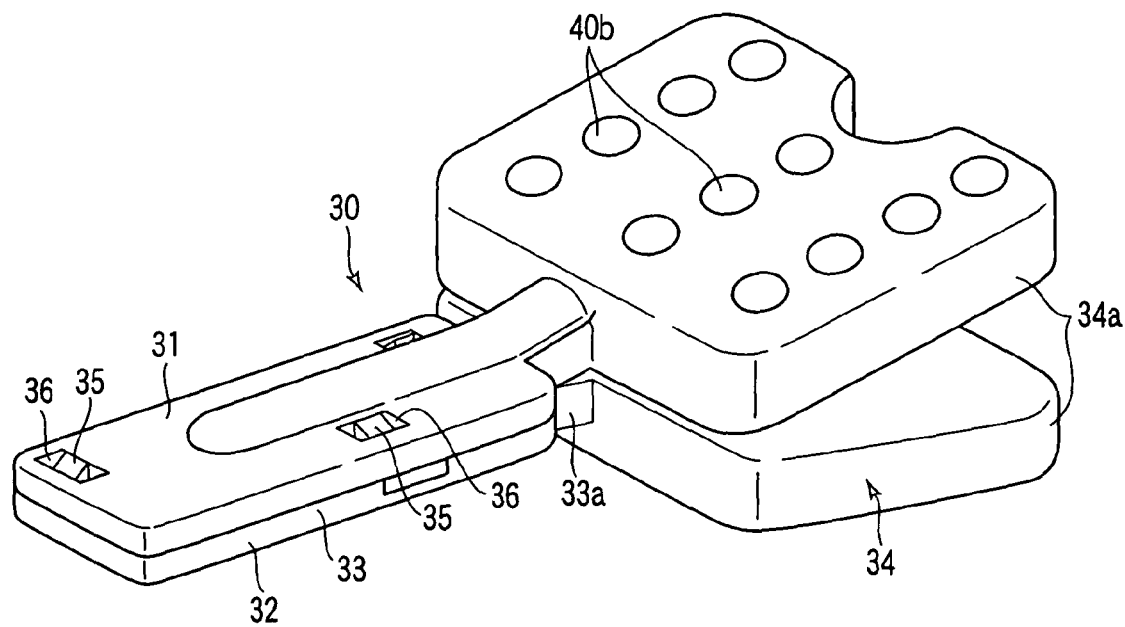
FIG. 12 is a perspective view of a clip case according to the embodiment.
Figure 13:
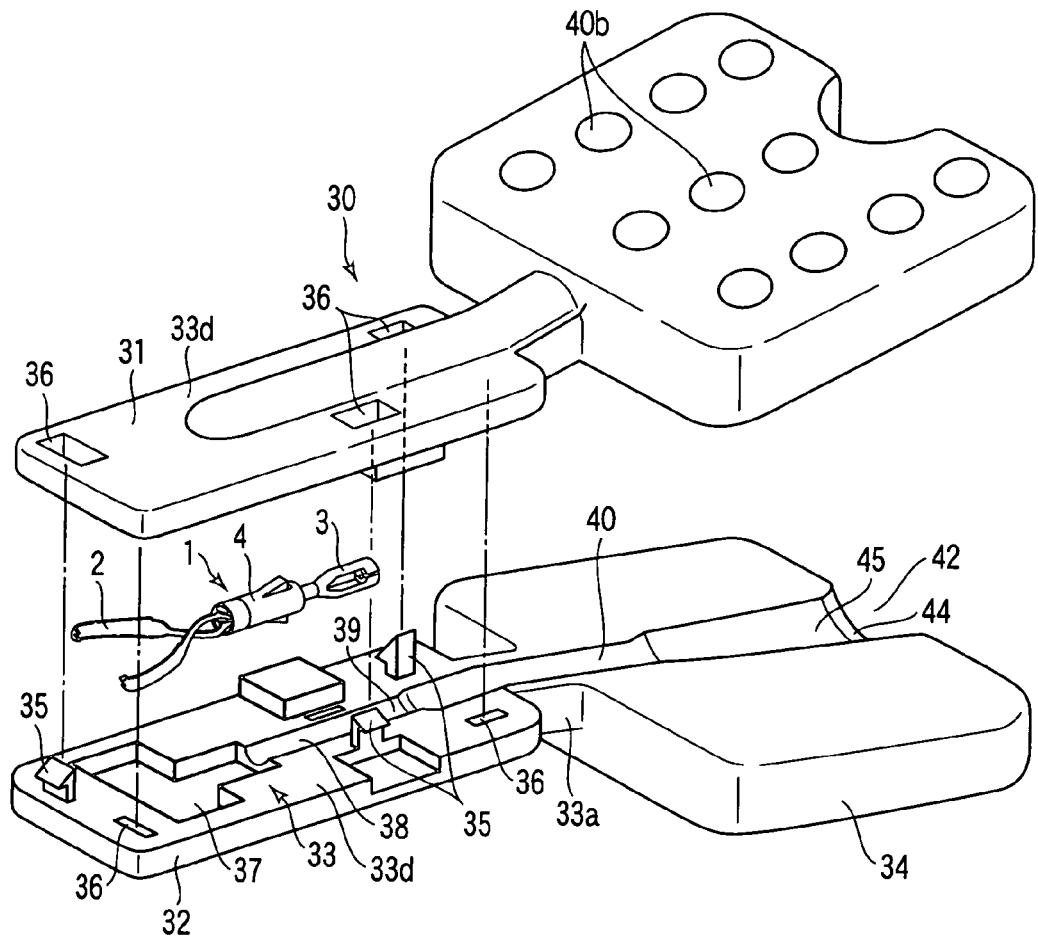
FIG. 13 is an exploded perspective view of the clip case according to the embodiment.

As shown in FIG. 6A, the arrowhead hook 8 is detachably engaged with the gripping portion 3e of the coupling member 3. A length 8c' of the shaft portion 8c is longer than the length of the gripping portion 3e by 0.5 mm or more. As shown in FIG. 8B, therefore, while the arrowhead hook 8 is engaged with the gripping portion 3e of the coupling member 3, a spacing 8g is formed between the rear end face of the gripping portion 3e and the distal end abutment surface of the wire fixing portion 8a.

Figure 6B:
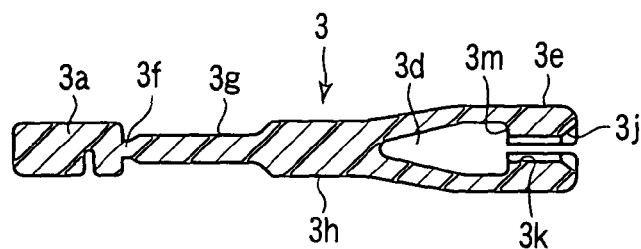
FIG. 6B is a partially cutaway view of the coupling member of the device.
Figure 6C:
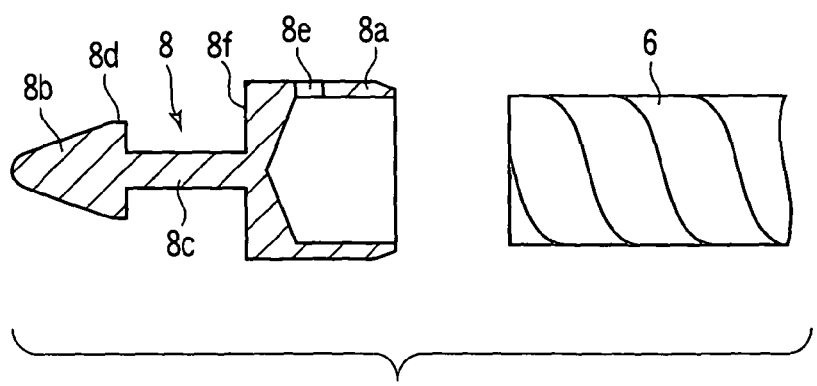
FIG. 6C is a sectional view showing the fixing structure of an arrowhead hook.

As shown in FIG. 6B, a conical hole 3j conforming to the inclined surface of the arrowhead inclined portion 8b is formed in the gripping portion 3e of the coupling member 3 to allow the coupling member 3 to be easily coupled to the arrowhead hook 8. A concave groove 3k fitted on the shaft portion 8c is formed in the gripping portion 3e continuously with the conical hole 3j. When the arrowhead hook 8 is engaged with the gripping portion 3e, the arrowhead hook 8 is fitted in the notched portion 3d, and the arrowhead large-diameter portion 8d is engaged with a stepped portion 3m of the gripping portion 3e.

When, therefore, the distal end portion of the arrowhead hook 8 is pressed against the conical hole 3j formed in the gripping portion 3e of the coupling member 3, and the arrowhead hook 8 is pushed into the gripping portion 3e, the gripping portion 3e is coupled to the arrowhead hook 8. When the coupling member 3 is to be removed from the arrowhead hook 8, as shown in FIGS. 8A and 8B, the coupling member 3 is pivoted along the opening direction of the notched portion 3d with respect to an axis o of the operating wire 6. This allows the arrowhead hook 8 to be removed from the notched portion 3d of the coupling member 3. At this time, since the spacing 8g is formed between the rear end face of the gripping portion 3e and the distal end abutment face of the wire fixing portion 8a, there is no chance that the gripping portion 3e will interfere with the wire fixing portion 8a.

FIGS. 9A to 11 show an operating portion 9. An operation portion body 10 is comprised of a cylindrical portion 10a on the distal end side, a shaft-like portion 10b which extends to the rear end side integrally with the cylindrical portion 10a, and a finger rest ring 10c which is rotatably provided at the proximal end portion of the shaft-like portion 10b. A slit 10d is provided in the shaft-like portion 10b of the operation portion body 10 in the axial direction. A slider 11 having a finger rest concave portion 11a is retractably provided on the outer circumferential surface of the slit 10d.

The proximal end portion of the operating wire 6 which extends through the cylindrical portion 10a of the operation portion body 10 is introduced into a lumen 11b of the slider 11. A two-piece wire fixing member 12 is provided at a position offset to the proximal end side of the lumen 11b of the slider 11. A proximal end portion 6b of the operating wire 6 is clamped and fixed by the two-piece wire fixing member 12. The wire fixing member 12 is fixed to the slider 11 by a lid member 14 fixed with screws 13.

When, therefore, the slider 11 is moved back and forth with respect to the operation portion body 10, the operating wire 6 is moved back and forth in the introduction tube 5. Since the distal end side of the lumen 11b of the slider 11 is open, when the slider 11 is moved forward to the limit, a proximal end large-diameter portion 10a' of the cylindrical portion 10a of the operation portion body 10 is fitted in the slider 11. This makes it possible to increase the stroke of the slider 11 while decreasing the length of the operating portion 9.

Although the wire fixing member 12 is provided at the position offset to the proximal end side of the lumen 11b of the slider 11, the same effect as described above can be obtained even by providing the wire fixing member 12 at a position offset to the distal end side of the lumen 11b of the slider 11 so as to be fitted in the proximal end side of the operation portion body 10.

A pipe 15 made of stainless steel is fitted on the operating wire 6 which extends through the cylindrical portion 10a of the operation portion body 10. An inner circumference large-diameter portion 16 is formed at the distal end portion of the cylindrical portion 10a, and a coil joint tube 17 fixed to the cylindrical portion 10a is fixed to the inner circumference large-diameter portion 16.

A fracture prevention tube 18 is coupled to the coil joint tube 17. The fracture prevention tube 18 is formed by using a spring material such as stainless steel or a resin material having appropriate softness such as a silicone heat-shrinkable tube, and is fitted on the operator-side coil 5a of the introduction tube 5 which is coupled to the coil joint tube 17 while being fitted on the operating wire 6. The fracture prevention tube 18 is provided to protect the coupling portion between the coil joint tube 17, which is susceptible to fracture, and the fracture prevention tube 18. Providing the coupling portion between the coil joint tube 17 and the fracture prevention tube 18 inside the operation portion body 10 allows the operation portion body 10 to protect the coupling portion having low strength. This can greatly improve the durability.

FIGS. 12 to 17C show a clip case 30 which houses the clip unit 1. The clip case 30 is comprised of upper and lower cases 31 and 32 having the same dimensions and shape, which can be molded by the same mold. The upper and lower cases 31 and 32 are manufactured by injection-molding a transparent resin having appropriate hardness, e.g., ABS, PC, PP, PS, acrylic, or cycloolefin polymer. The clip case 30 is formed to have a size that allows the operator to easily hold it with his/her hand, having a width of about 10 mm to 20 mm, a length of about 50 mm, and a thickness of about 5 mm.

Clip unit housing portions 33 are provided at one end portion of the upper and lower cases 31 and 32 in the longitudinal direction, and compressing portions 34 are provided at the other end portion. The compressing portions 34 are formed to have a size that is suitable for the operator to grip them with his/her fingers, having a size of about 20 mm×20 mm. Coupling portions 33a between the clip unit housing portions 33 and the compressing portions 34 are bent so that the compressing portions 34 of the upper and lower cases 31 and 32 are spaced apart from each other so as to form a spacing 34a between the compressing portions 34.

Three engaging pawls 35 extend vertical from each of the inner surfaces of the clip unit housing portions 33 of the upper and lower cases 31 and 32, and three engaging holes 36 are provided for each of the inner surfaces. The engaging pawls 35 of the upper case 31 engage with the engaging holes 36 of the lower case 32, and the engaging pawls 35 of the lower case 32 engage with the engaging holes 36 of the upper case 31, thereby assembling the upper and lower cases 31 and 32.

Since the upper and lower cases 31 and 32 have the same shape, only the lower case 32 will be described below. A clip housing portion 37 formed from an almost T-shaped concave portion in which the clip 2 of the clip unit 1 is housed in the open state is provided on the inner surface of the clip unit housing portion 33. A press tube housing portion 38 and coupling member housing portion 39 which are formed from arcuated grooves are formed continuously with the clip housing portion 37. The bottom portion of the press tube housing portion 38 has a retractable wing housing concave portion 38a in which the retractable wings 4d are housed. The bottom portion of the coupling member housing portion 39 has a grip portion clearance concave portion 39a to allow the coupling member housing portion 39 to deform when the gripping portion 3e engages with the arrowhead hook 8.

An introduction tube insertion portion 40 formed from an arcuated groove is provided on the inner surface of the compressing portion 34 continuously with the coupling member housing portion 39. A plurality of semispherical concave portions 40b, each having a diameter of about 1 mm to 3 mm, are provided on the outer surface of the compressing portion 34 so as to form an anti-slip portion.

A retractable wing diameter reducing portion 41 which has a distal end chip abutment portion 41a having a rear end as a flat vertical surface and also has an inclined surface having an angle of about 5° to 90° formed on the front portion is provided at the boundary portion between the coupling member housing portion 39 and the introduction tube insertion portion 40. When the press tube 4 passes through the retractable wing diameter reducing portion 41, the retractable wings 4d are pushed inside.

The introduction tube insertion portion 40 is provided with an inclined surface portion 43 to gradually increase the diameter toward an inlet 42. An arcuated surface 44 which has a diameter of 3 mm or more and is semicircular in plan view is formed at the inlet 42. A convex portion having a length of 1 mm to 5 mm is formed in the bottom surface of the introduction tube insertion portion 40. This convex portion forms an introduction tube fixing portion 45 which presses and fixes the introduction tube 5 in the vertical direction.

Engaging concave portions 46 are provided in the two side walls of the clip housing portion 37 so as to face each other. Engaging convex portions 48 provided on the two ends of a clip abutment portion 47 are detachably engaged with the engaging concave portions 46. The clip abutment portion 47 has abutment surfaces 47a and 47b on its front and rear portions to prevent the clip 2 from moving forward. The engaging convex portions 48 are provided to be offset from the abutment surfaces 47a and 47b.

Figure 16A:
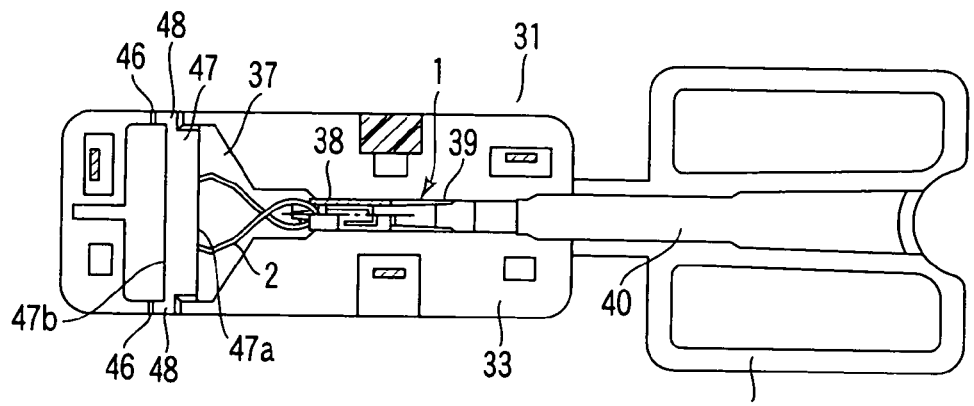
FIGS. 16A to 16C are plan views respectively showing different states of the lower case according to the embodiment.
Figure 16B:
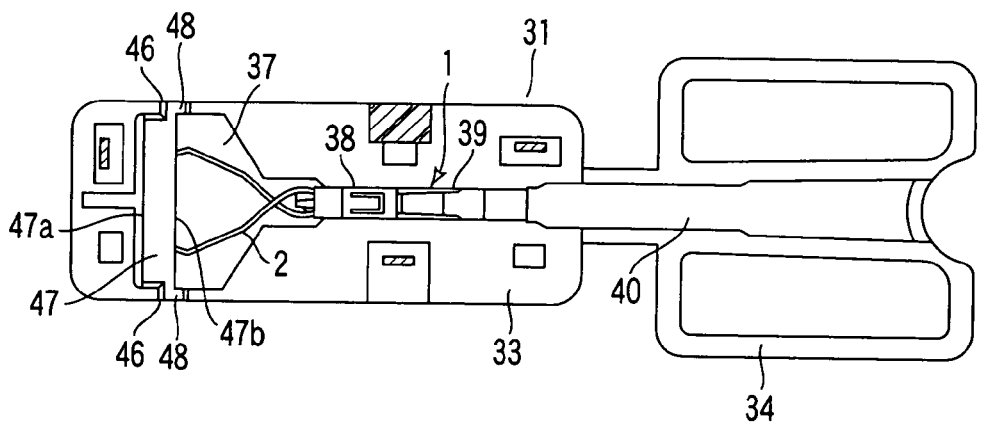
Figure 16C:
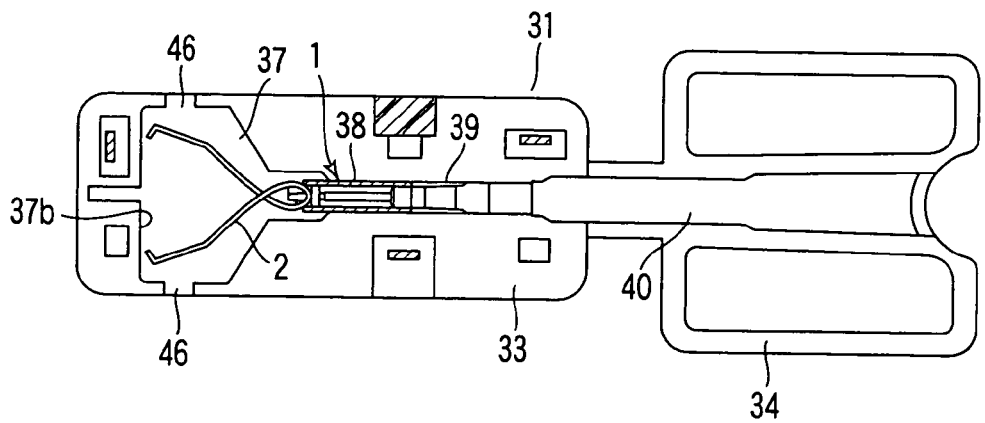

If, therefore, the clip 2 to be housed in the clip housing portion 37 has a small size, the engaging convex portions 48 of the clip abutment portion 47 can be engaged with the engaging concave portions 46 so as to make the abutment surface 47a abut against the clip 2, as shown in FIG. 16A. If the clip 2 to be housed in the clip housing portion 37 has a medium size, the clip abutment portion 47 can be inverted to engage the engaging convex portions 48 with the engaging concave portions 46 so as to make the abutment surface 47b abut against the clip 2, as shown in FIG. 16B. If the clip 2 to be housed in the clip housing portion 37 has a large size, the clip abutment portion 47 can be removed to make the clip 2 abut against a front wall 37a of the clip housing portion 37, as shown in FIG. 16C.

Figure 17A:
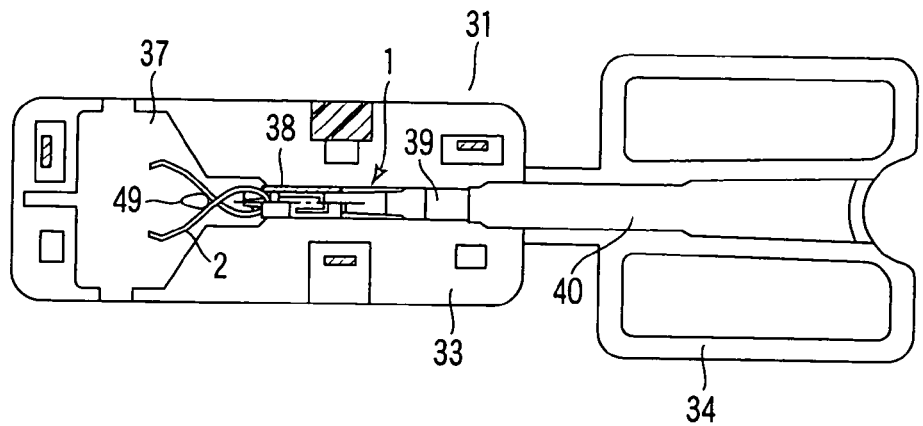
FIGS. 17A to 17C are plan views respectively showing different states of the lower case according to a modification to the embodiment.
Figure 17B:
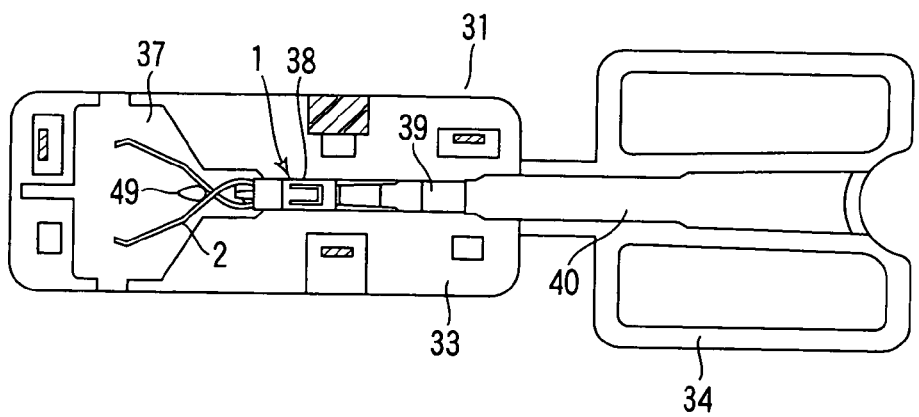
Figure 17C:
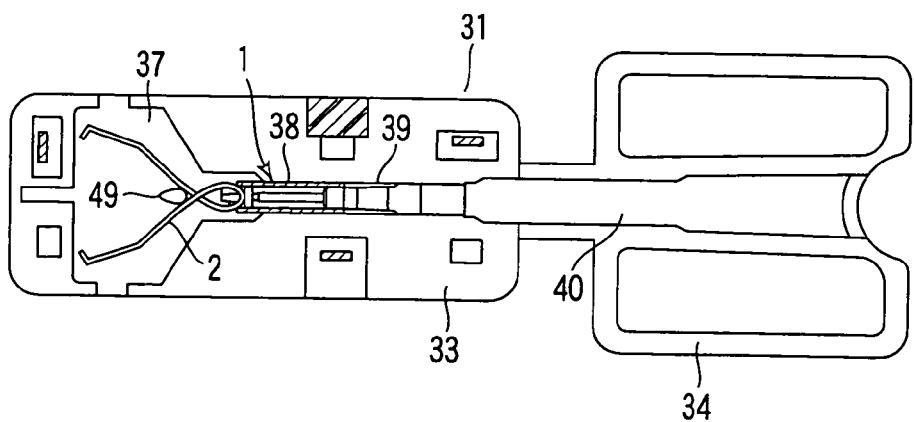

As shown in FIGS. 17A to 17C, the clip abutment portion 47 may have a clip abutment member 49 in the form of a projection provided on the bottom portion of the clip housing portion 37. According to this modification, the intersecting portion of the arms 2b of the clip 2 abut against the clip abutment member 49 to prevent the clip 2 from moving forward regardless of the size of the clip 2.

The function of the living tissue ligation device having the above arrangement will be described next.

The clip unit 1 is housed between the upper and lower cases 31 and 32 of the clip case 30, and the clip 2, press tube 4, and coupling member 3 are respectively set in the clip housing portion 37, press tube housing portion 38, and coupling member housing portion 39.

When the clip unit 1 is to be attached to the ligation device in this state, first of all, as shown in FIG. 18A, the distal end portion of the introduction tube 5 is inserted into the introduction tube insertion portion 40 through the inlet 42 of the clip case 30, and the distal end chip 7 is made to abut against the distal end chip abutment portion 41a.

When the compressing portions 34 of the clip case 30 are then gripped with fingers, the compressing portions 34 elastically deform, and the introduction tube 5 is clamped by the introduction tube fixing portion 45 so as not to move in the axial direction, as shown in FIG. 18B.

Figure 19A:
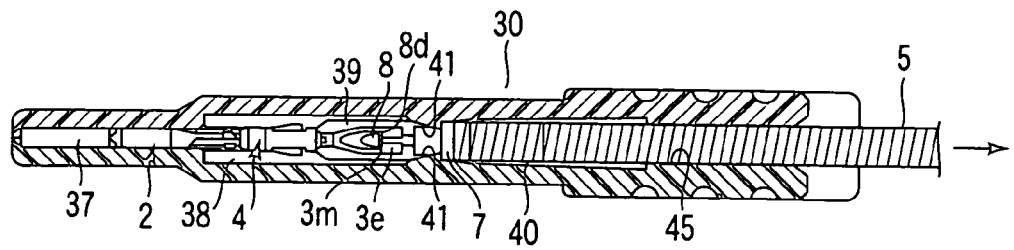
FIGS. 19A to 19C are sectional views showing the clip case according to the embodiment in different states to explain the function of the clip case.

When the slider 11 of the operating portion 9 is moved to the distal end side in this state, the arrowhead hook 8 protrudes from the distal end portion of the introduction tube 5 through the operating wire 6. As a consequence, the distal end portion of the arrowhead hook 8 abuts against the conical hole 3j formed in the gripping portion 3e of the coupling member 3. As shown in FIG. 18C, when the slider 11 is further moved to the distal end side, the gripping portion 3e is expanded outward by the arrowhead inclined portion 8b. When the arrowhead hook 8 is pushed into the gripping portion 3e afterward, the gripping portion 3e is closed by elastic force when the arrowhead hook 8 passes the projection portion 3k, and the shaft portion 8a is clamped by the gripping portion 3e, as shown in FIG. 19A. Since the arrowhead large-diameter portion 8d of the arrowhead hook 8 engages with the stepped portion 3m of the gripping portion 3e in this state, the arrowhead hook 8 cannot be removed from the gripping portion 3e, and the clip unit 1 is coupled to the operating wire 6.

Figure 19B:
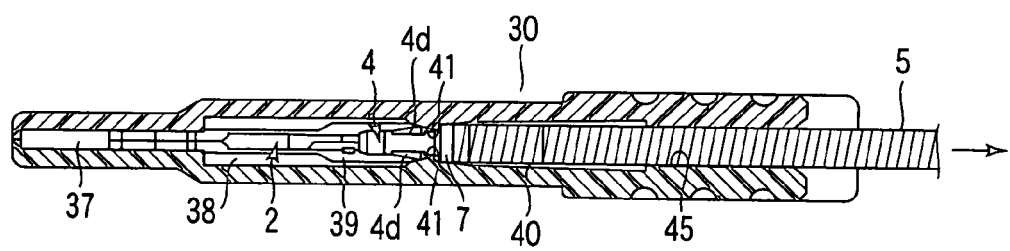
Figure 19C:
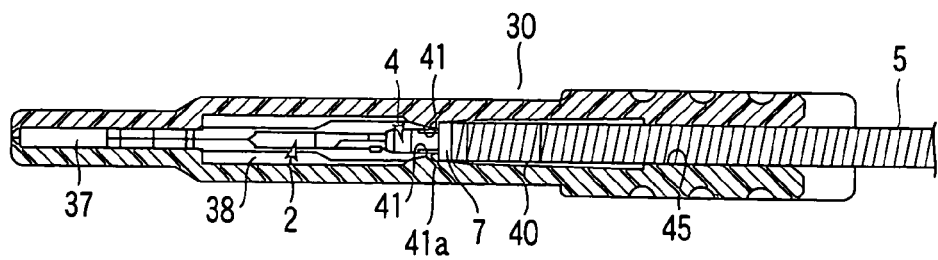

When the slider 11 is moved to the proximal end side in this state, the clip unit 1 is pulled into the introduction tube 5 through the operating wire 6. At this time, as shown in FIG. 19B, the retractable wings 4d of the press tube 4 are pushed inside by the inclined surface of the retractable wing diameter reducing portion 41 and pulled into the press tube 4. As shown in FIG. 19C, therefore, the clip unit 1 is pulled into the introduction tube 5 without causing the retractable wings 4d to be caught on the end face of the distal end chip 7.

At this time, the arms 2b of the clip 2 are closed so as to conform to the inner diameter of the introduction tube 5. In addition, the retractable wings 4d of the press tube 4 are in contact with the inner surface of the introduction tube 5, and hence elastically deform to be kept housed in the press tube 4.

When the gripping force of the compressing portion 34 of the clip case 30 is reduced after the clip unit 1 is completely pulled into the introduction tube 5, the compressing portions 34 spread apart in the vertical direction owing to the elastic restoring force. As shown in FIG. 20, the introduction tube 5 can be removed from the introduction tube insertion portion 40 of the clip case 30.

Figure 21A:
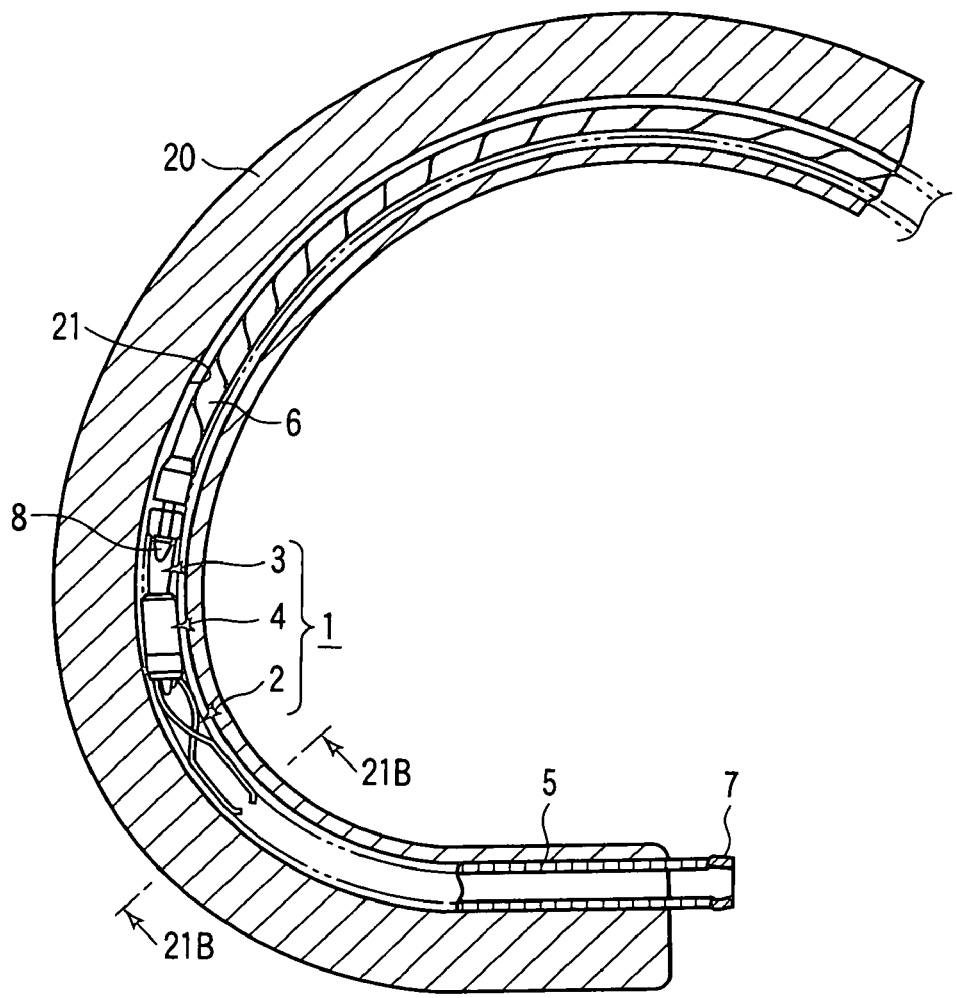
FIG. 21A is a partially cutaway side view of the insertion portion of an endoscope according to the embodiment.
Figure 21B:
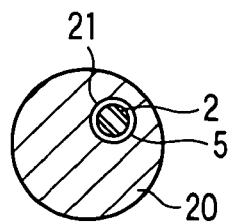
FIG. 21B is a sectional view taken along a ling 21B-21B of FIG. 21A.

As shown in FIG. 21A, the introduction tube 5 is introduced into the body cavity through the channel 21 of the endoscope 20 which is inserted in the body cavity in advance. The operator then guides the distal end of the introduction tube 5 to a target region while observing the body cavity with the endoscope 20.

Figure 22A:
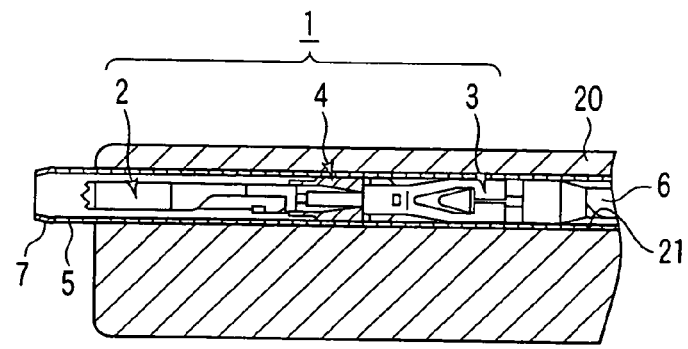
FIGS. 22A to 22C are views for explaining a sequence of ligating the living tissue with the clip.

FIGS. 22A to 23D show a sequence of ligating the tissue by using the clip 2. When the slider 11 is pushed out to the distal end side, the clip unit 1 moves forward in the introduction tube 5 through the operating wire 6, as shown in FIG. 22A. At this time, since the inclined surface 4c' is formed on the outside of the distal end tube 4a of the press tube 4 to gradually decrease the outer diameter of the distal end tube 4a toward the distal end portion so as to make the distal end tube 4a smoothly slide on the inside of the introduction tube 5, the clip unit 1 smoothly moves in the introduction tube 5.

Figure 22B:
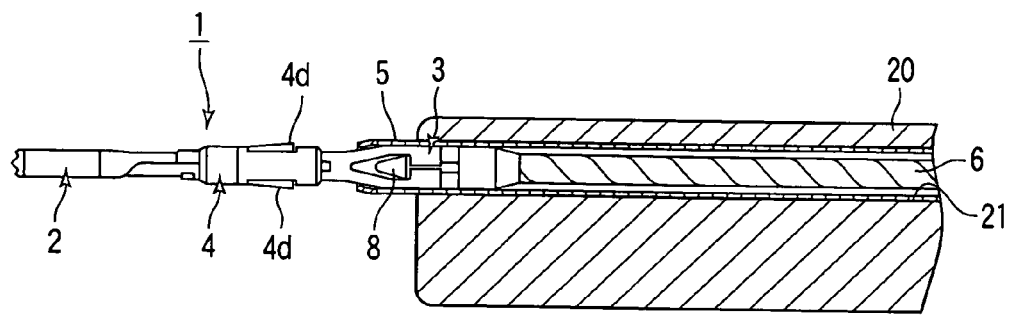
Figure 23A:
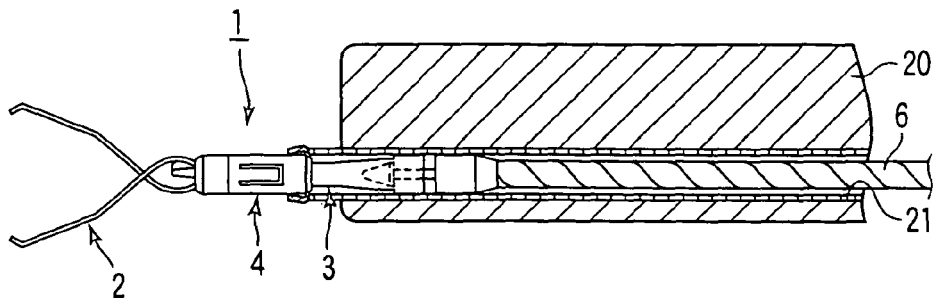
FIGS. 23A to 23D are views showing a sequence of ligating the living tissue with the clip.

When the operating wire 6 is further moved forward by using the slider 11, the clip unit 1 protrudes from the introduction tube 5, as shown in FIG. 22B. At this time, since each retractable wing 4d of the press tube 4 has a down grade toward the distal end side, the clip unit 1 is pushed out smoothly without any resistance. At this time, the retractable wings 4d of the press tube 4 are released from the contact state with the inner surface of the introduction tube 5, and protrude in the outer circumferential direction of the press tube 4. In addition, as shown in FIG. 23A, since the pair of arms 2b of the clip 2 have the property of spreading apart, they spread apart to some degree at the same time when they protrude from the introduction tube 5.

Figure 22C:
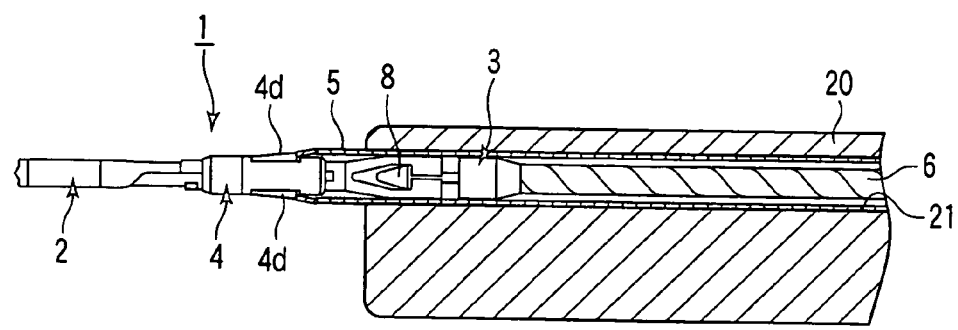

When the slider 11 is moved to the proximal end side afterward, the operating wire 6 is pulled back to the proximal end side, as shown in FIG. 22C, and the proximal end faces of the retractable wings 4d of the press tube 4 engage with the end face of the distal end chip 7.

Figure 23B:
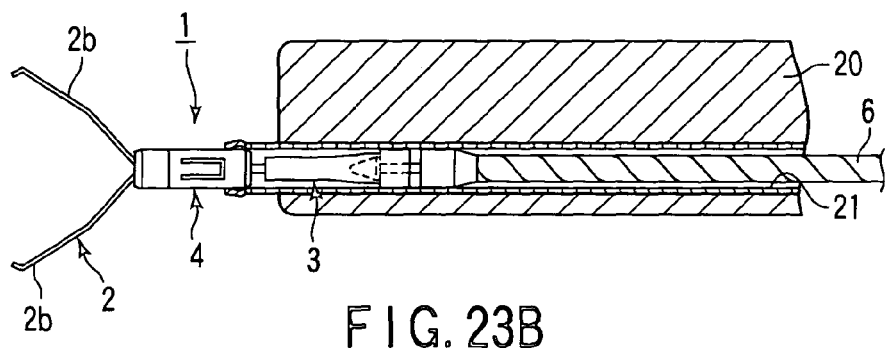

When the slider 11 is further moved to the proximal end side to pull back the operating wire 6, the loop portion 2a of the clip 2 is pulled into the press tube 4 through the coupling member 3, and the clip 2 opens. The projections 2d of the clip 2 then come into contact with the inner-diameter stepped portion 4f of the press tube 4, and the arms 2b spread apart to the limit, as shown in FIGS. 4C and 23B.

In this state, the operator approaches the clip 2 to a target region of the living tissue while observing it with the endoscope 20, and presses the tissue gripping portion 2c of the clip 2 against the target region. At this time, the operator inserts his/her thumb into the finger rest ring 10c of the operating portion 9 and grips the slider 11 with his/her index finger and middle finger to operate the operating portion 9. The finger rest ring 10c is rotatable with respect to the operation portion body 10. When the clip 2 is to be rotated to change its orientation, the operation portion body 10 is rotated. At this time, the operation portion body 10 can be rotated while the thumb is kept inserted in the finger rest ring 10c.

Figure 23C:
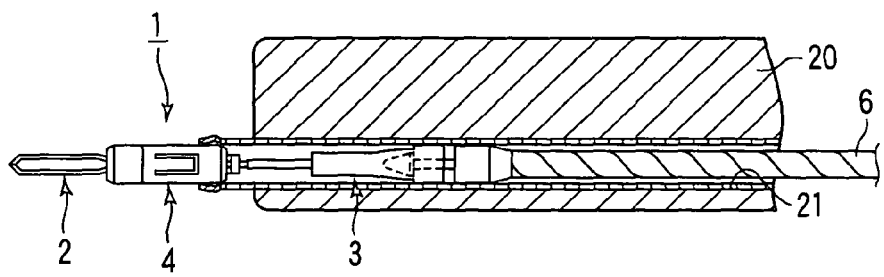

When the slider 11 is further moved to the proximal end side, the operating wire 6 is moved backward, and the arms 2b of the clip 2 are pulled into the press tube 4 through the coupling member 3. As a consequence, the projections 2d of the clip 2 move over the inner-diameter stepped portion 4f of the press tube 4, and the arms 2b of the clip 2 are closed, as shown in FIGS. 5A, 5B, and 23C. As a result, the living tissue is reliably clamped between the arms 2b of the clip 2. At this time, since the press tube 4 is made of a resin having appropriate elasticity which is softer than the clip 2, the projections 2d of the clip 2 bite into the inner wall of the press tube 4 to restrict the clip 2 from moving in the press tube 4 in the axial direction, thereby maintaining the closed state.

Figure 23D:
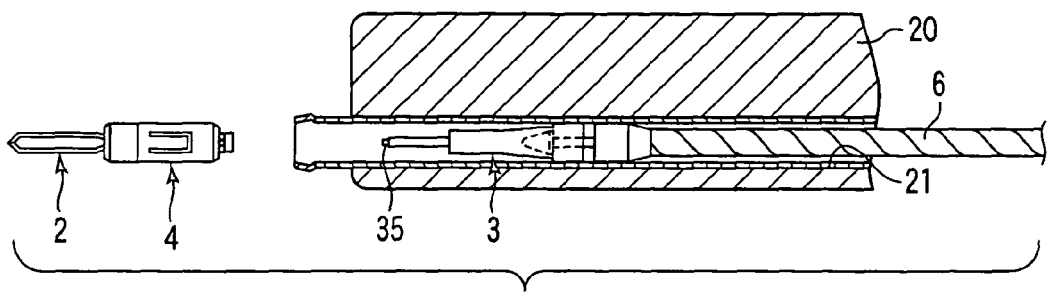

When the slider 11 is further moved to the proximal end side to move the operating wire 6 backward, the small-diameter portion 3f serving as the fracture portion of the coupling member 3 of the clip 2 fractures, as shown in FIG. 23D. The clip 2 is then disengaged from the coupling member 3, and separates from the ligation device, together with the press tube 4. As a consequence, the clip 2 is indwelled in the body cavity while gripping the living tissue.

For example, the living tissue of a bleeding region in the body cavity is clamped and pressed between the arms 2b of the clip 2, and the clip 2 is indwelled in the body cavity in this state. This makes it possible to stop bleeding by pressing the blood vessel in the bleeding region. The clip 2 is left alone for several days until the bleeding stops while gripping the living tissue. The projections 2d of the clip 2 bite into the inner wall of the press tube 4 to restrict the clip 2 from moving in the press tube 4 in the axial direction, thereby maintaining the closed state.

After the clip 2 is indwelled in the body cavity, the ligation device is removed from the channel 21 of the endoscope 20. When the coupling member 3 is to be removed from the arrowhead hook 8, as shown in FIGS. 8A and 8B, the coupling member 3 is pivoted in the direction indicated by the arrow along the opening direction of the notched portion 3d of the coupling member 3 with respect to the axis of the operating wire 6. With this operation, the arrowhead hook 8 can be removed from the notched portion 3d of the coupling member 3. At this time, since the spacing 8g is formed between the wire fixing portion 8a and a distal end contact surface 6b, there is no chance that the gripping portion 3e will interfere with the wire fixing portion 8a.

Figure 24:
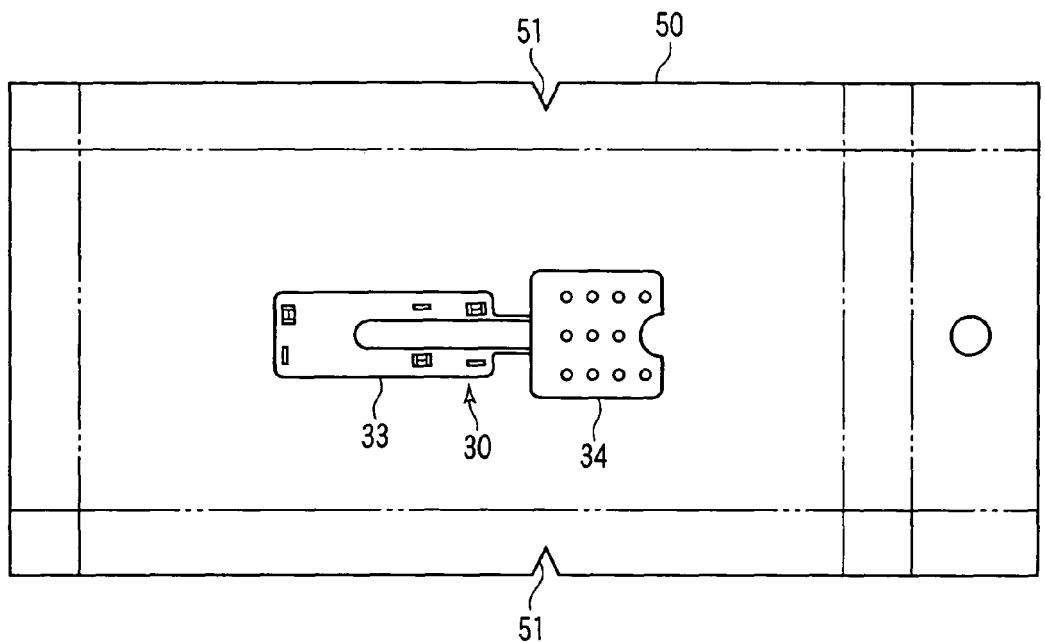
FIG. 24 is a plan view of a peel pack according to the second embodiment of the present invention.
Figure 25:
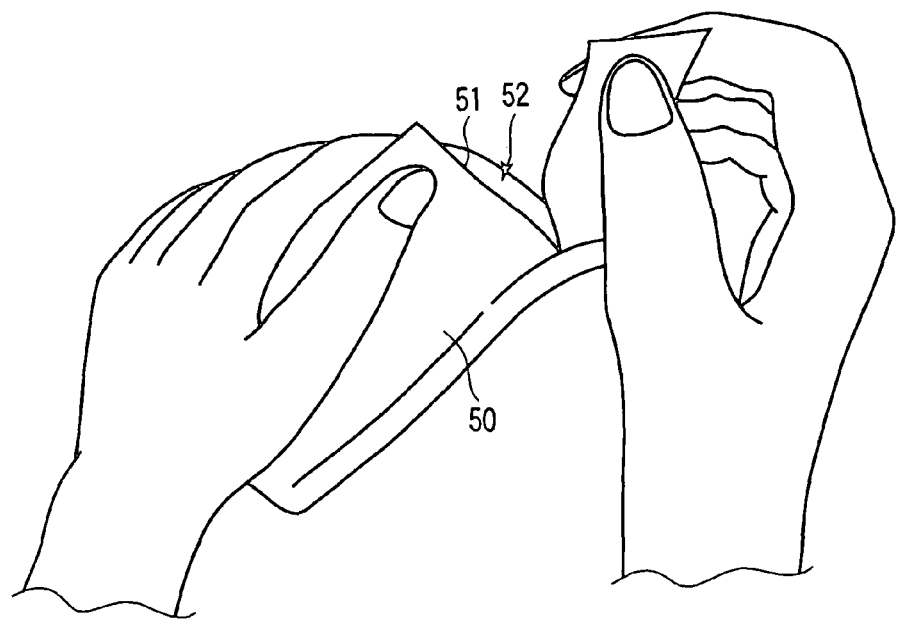
FIG. 25 is a perspective view of the peel pack according to the embodiment.

FIGS. 24 to 26C show the second embodiment, and show a peel pack 50 which houses a sterilized clip case 30. As shown in FIG. 24, the peel pack 50 is a combination of a high-density polyethylene mount with a polyethylene coating and a polyethylene and PET multilayer film and has a rectangular, bag-like shape. The peel pack 50 has triangular notched portions 51. As shown in FIG. 25, therefore, an operator can form an opening portion 52 by tearing the peel pack 50 from the notched portion 51 with his/her fingers.

Figure 26A:
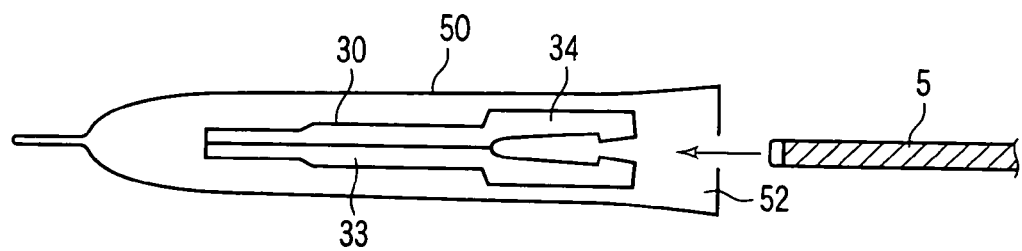
FIGS. 26A to 26C are views of different operation states for explaining the function of the peel pack according to the embodiment.
Figure 26B:
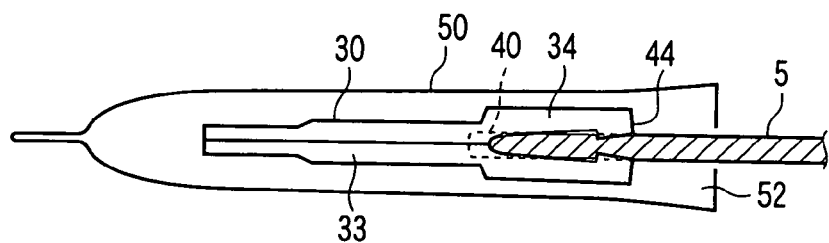
Figure 26C:
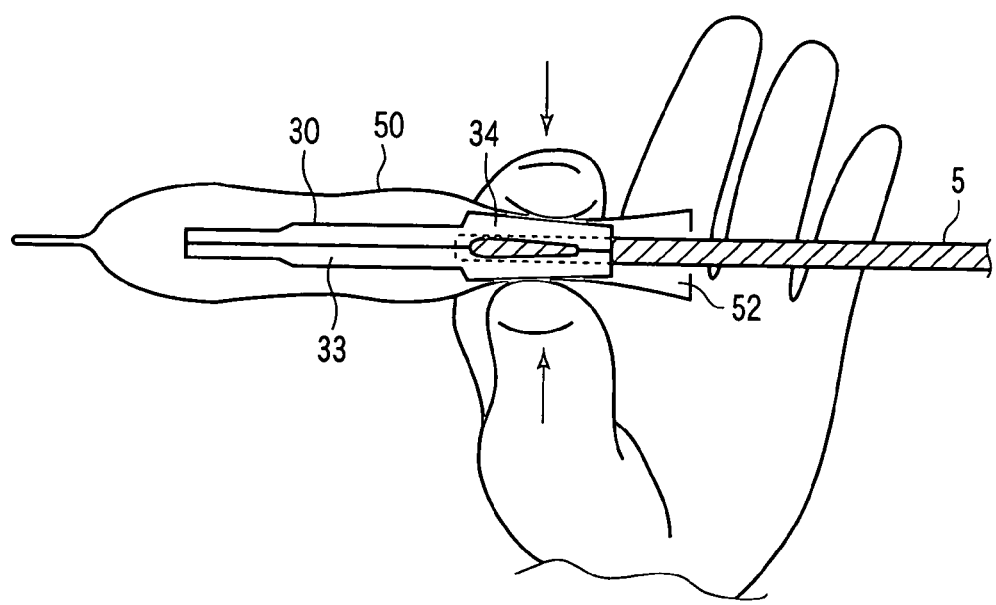
Figure 28A:
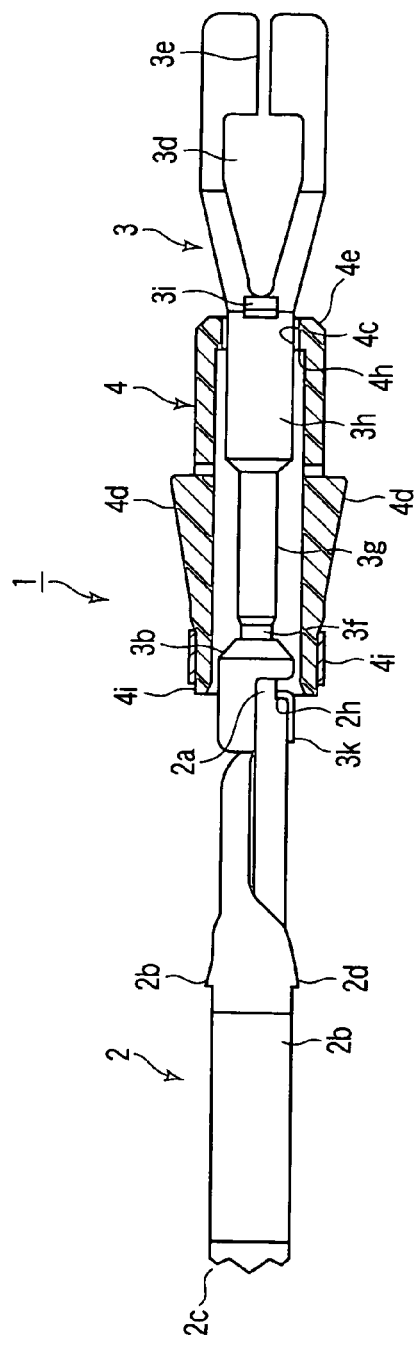
FIGS. 28A and 28B are a partially cutaway plan view of a clip unit according to the embodiment and a partially cutaway side view of the clip unit.
Figure 28B:
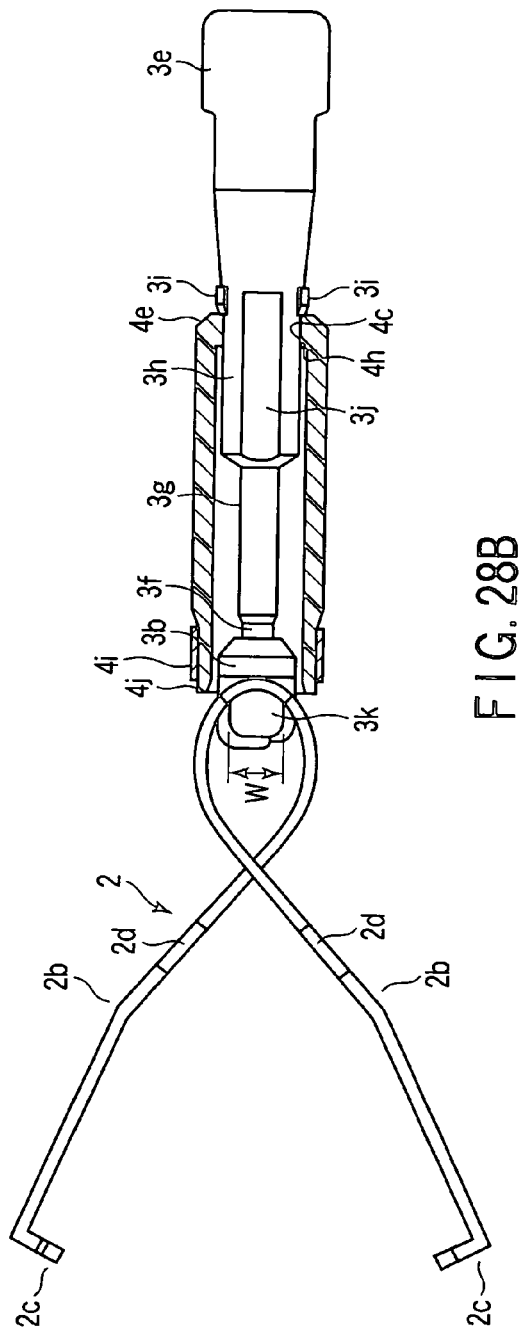

After the peel pack 50 housing the clip case 30 is provided with the opening portion 52, a clip unit 1 is attached to a ligation device in the following manner. First of all, as shown in FIG. 26A, the distal end portion of an introduction tube 5 is inserted from the opening portion 52 of the peel pack 50 in the direction indicated by the arrow. As shown in FIG. 26B, the introduction tube 5 is inserted into an introduction tube insertion portion 40 from an introduction tube insertion inlet 44 of the clip case 30. The operator then grips compressing portions 34 of the clip case 30 through the peel pack 50 with his/her fingers from the direction indicated by the arrows, and can attach the clip unit 1 to the ligation device by the sequence shown in FIGS. 18A to 19C.

FIGS. 27A to 34 show the third embodiment. The same reference numerals as in the first embodiment denote the same constituent parts in the third embodiment, and a description thereof will be omitted. According to Jpn. Pat. Appln. KOKAI Publication No. 8-280701 described in the prior art, the click is pulled into the clamping ring by using the operating wire, and the living tissue is ligated by closing the arms of the clip. The clamping ring is structured such that the coupling member is inserted in the cylindrical tube-like member having the two open ends. The loop portion of the clip is engaged with the distal end portion of the coupling member, and the coupling member is pulled to the operator side to house the clip in the clamping ring in the closed state.

The coupling member may therefore move in the axial direction of the clamping ring inside the clip case or introduction tube to disengage from the clip. As a result, the clip may separate from the coupling member. This embodiment is directed to solve the above problem.

As shown in FIGS. 27A to 27C, the proximal end portion of a loop portion 2a of a clip 2 forming a clip unit 1 is formed to have a width smaller than those of the remaining portions, and loop stepped portions 2h serving as lock members are formed on the two side portions of the loop portion 2a which are continuous from the proximal end portion. The almost intermediate portions of arms 2b are provided with sawtooth-like projections 2d protruding in the plate width direction. The projections 2d slide on the inner surface of a press tube 4 in the direction in which the clip 2 is pulled into the press tube 4, but bite into the inner surface of the press tube 4 in the direction opposite to the pulling direction.

The dimensions of the clip 2 will be described. Each loop stepped portion 2h has a width of 0.1 mm or more, and each projection 2d has a width that allows the clip 2 to be pulled into the press tube 4 and a distal end tube (to be described later), i.e., a width of 1 mm or more.

As shown in FIGS. 28A to 31D, the coupling member 3 is manufactured by, for example, injection-molding a high-strength resin material such as a liquid crystal polymer or nylon, and has a cylindrical, rodlike shape. The coupling member 3 has a projection portion 3k provided at its distal end portion. The projection portion 3k protrudes from a proximal portion 3b. A width w of the projection portion 3k is about 0.6 mm to 1.2 mm. The clip 2 is designed such that when the clip 2 is pulled into the press tube 4 while the loop portion 2a of the clip 2 is hooked on the projection portion 3k, the clip 2 is slidably moved in tight contact with the inner circumferential surface of the press tube 4, i.e., gradually pulled into the press tube 4 with a large sliding resistance.

Flat surface portions 3j serving as engaging portions are formed on the opposing surfaces of a large-diameter portion 3h of the coupling member 3 along the axial direction. That is, the large-diameter portion 3h is formed into a noncircular shape. Lock projections 3i are provided on portions of the outer circumferential surface of the large-diameter portion 3h at the terminal portions of the flat surface portions 3j.

The dimensions of the coupling member 3 will be described. The coupling member 3 has a total length of about 10 mm. A gripping portion 3e has an inner diameter of 0.6 mm. A small-diameter portion 3f has an outer diameter of 0.3 mm or more. The large-diameter portion 3h has a diameter of 1 mm to 1.3 mm. In addition, the height of the lock projection 3i is set to 0.1 mm or more.

The press tube 4 is manufactured by injection-molding a material softer than the clip 2, for example, a high-rigidity resin having appropriate elasticity such as PPA (polyphthalamide) or PA (polyamide). The press tube 4 serves to close the arms 2b of the clip 2 when the press tube 4 is fitted on the arms 2b of the clip 2. A distal end tube 4i made of a high-strength metal such as stainless steel is fitted on the distal end portion of the press tube 4.

The distal-end tube 4i has an inner diameter that allows it to be fitted on the press tube 4, and an outer diameter that is almost equal to that of the press tube 4, and is shorter than a distal end fitting portion 4j of the press tube 4. The distal end tube 4i is located behind the distal end of the distal end fitting portion 4j, so that the two end portions form a pseudo-tapered portion. This allows the distal end tube 4i to smoothly move in a bent introduction tube 5 without being caught on the inner wall of the introduction tube 5.

The inner diameter of the proximal end portion of the press tube 4 has a rear end diameter reducing portion 4c to tightly fit the proximal end portion on the large-diameter portion 3h of the coupling member 3, thereby forming an inner diameter stepped portion 4h serving as a lock member having a level difference of 0.1 mm or more. When the clip 2 is pulled into the press tube 4, the loop stepped portions 2h of the clip 2 engages (comes into contact) with the inner diameter stepped portion 4h, thereby preventing the clip 2 from being pulled into the press tube 4 beyond the closing position.

The assembly of the clip unit 1 will be described below. As shown in FIGS. 32A and 32B, the distal end portion of the coupling member 3 is inserted from the proximal end portion side of the press tube 4, and the projection portion 3k of the distal end portion of the coupling member 3 is made to protrude from the distal end portion of the press tube 4. At this time, when the large-diameter portion 3h of the coupling member 3 is press-fitted in the press tube 4, since the large-diameter portion 3h is formed into a noncircular shape by the flat surface portions 3j, the press tube 4 smoothly deforms into an almost elliptic shape without causing the lock projections 3i provided on the large-diameter portion 3h to cut or deform the inner circumferential surface of the press tube 4.

In this state, after the loop portion 2a of the clip 2 is engaged with the projection portion 3k of the coupling member 3, the coupling member 3 is moved to the proximal end side, and the lock projections 3i are made to protrude from the proximal end portion of the press tube 4 to be engaged therewith. In this manner, the press tube 4 is directly engaged with the coupling member 3 by the lock projections 3i, and the coupling member 3 does not accidentally move in the press tube 4 in the axial direction. This can prevent the clip 2 from separating from the coupling member 3 inside a clip case 30 and introduction tube 5.

According to the third embodiment described above, when the coupling member 3 is inserted into the press tube 4 at the time of assembly of the clip unit 1 and is pulled into the press tube 4 while the clip 2 is engaged with the distal end portion of the coupling member 3, the clip 2 is housed in the press tube 4. As a consequence, the press tube 4 is directly engaged with the coupling member 3 so as to prevent the coupling member 3 from accidentally moving in the press tube 4 in the axial direction. This can prevent the clip 2 from separating from the coupling member 3 in the clip case 30 and introduction tube 5.

In the third embodiment, the flat surface portions 3j are formed on the shaft portion of the coupling member 3 to allow the press tube 4 to directly engage with the coupling member 3 so as to prevent the coupling member 3 from accidentally moving in the press tube 4 in the axial direction. However, the shaft portion of the coupling member 3 may be formed into a polygonal shape or elliptic shape. That is, the shape of the shaft portion is not specifically limited.

FIGS. 33A and 33B show a modification to the press tube 4. A pair of key grooves 4j are formed in that portion of the inner circumferential surface of the press tube 4 which is located on the operator side in correspondence with the pair of lock projections 3*i* provided on the coupling member 3 so as to be spaced apart from each other by 180°. According to this modification, at the time of assembly of the clip unit 1, the lock projections 3*i* engage with the key grooves 4*j* to restrict the coupling member 3 from moving in the press tube 4 in the axial direction and circumferential direction.

FIG. 34 shows a modification of the clip 2. Tissue gripping portions 2*c* respectively provided at the distal end portions of the pair of arms 2*b* of the clip 2 are bent at an angle of almost 90°. In addition, the lengths of the arms 2*b* are made to differ by the plate thickness, so that the tissue gripping portions 2*c* overlap one another in the lateral direction when the arms are closed. According to this modification, the width by which the arms 2*b* are closed can be reduced to allow the clip 2 to smoothly move in the press tube 4.

FIGS. 35A to 36C show the fourth embodiment. The same reference numerals as in the first embodiment denote the same constituent parts in the fourth embodiment, and a description thereof will be omitted. According to Jpn. Pat. Appln. KOKAI Publication No. 8-280701 described in the prior art, when the clip is pulled into the clamping ring by using the operating wire, the loop portion of the clip is pressed by the inner circumferential surface of the clamping ring to open the arms of the clip to the limit and press the arms against the living tissue. When the clip is further pulled into the clamping ring in this state, the arms of the clip are pulled into the clamping ring to close the arms, thereby ligating the living tissue.

The above clamping ring is a tube-like member which has two open ends and has no stepped portion on the cylindrical inner surface. For this reason, when the clip is pulled into the clamping ring by using the operating wire to temporarily open the arms of the clip, it is difficult for an operator to determine whether or not the arms are opened to the limit, unless he/she carefully observes the open state of the arms of the clip with an endoscope. If the operator applies slightly excessive force on the clip, the arms close upon passing over the maximum open state. That is, the operator cannot hold the open state of the arms. This makes it impossible to obtain an intended amount of tissue gripped, and results in poor operability. This embodiment is directed to solve the above problem.

As shown in FIGS. 35A to 36C, a sawtooth-like projection 2*d* protruding in the plate width direction is provided near a loop portion 2*a* of a clip 2. The projection 2*d* slidably moves on the inner surface of the press tube 4 in the direction in which the clip 2 is pulled into a press tube 4, but bites into the inner surface of the press tube 4 in the direction opposite to the pulling direction.

The press tube 4 is designed to close arms 2*b* of the clip 2 when it is fitted on the arms 2*b*. The inner diameter of the distal end side of the press tube 4 is set to be slightly large to form an inner-diameter stepped portion 4*f* which locks the projection 2*d* of the clip 2 between the inner diameter of the distal end side and that of the rear end side.

As shown in FIGS. 35A and 35B, therefore, a coupling member 3 is pulled to the operator side, the loop portion 2*a* of the clip 2 is pulled into the press tube 4 from a distal end tube 4*a* of the press tube 4. As a consequence, the loop portion 2*a* of the clip 2 is flattened to open the arms 2*b*.

When the coupling member 3 is further pulled to the operator side, the projection 2*d* of the clip 2 comes into contact with the inner-diameter stepped portion 4*f* of the press tube 4 to temporarily stop pulling the clip 2, and the arms 2*b* are opened to the limit, as shown in FIGS. 36A to 36C.

In this state, the operator approaches the clip 2 to a target region of the living tissue while performing observation with an endoscope, and the tissue gripping portions 2*c* of the clip 2 is pressed against the target region. At this time, the projection 2*d* of the clip 2 comes into contact with the inner-diameter stepped portion 4*f* of the press tube 4, and the operator temporarily stops pulling the clip 2. The arms 2*b* are held in a state wherein they are opened to the limit.

According to this embodiment, the clip 2 is held in the state wherein the chip 2 is opened to the limit. When the clip 2 is pressed against the living tissue in this state and closed, the living tissue can be gripped with the clip 2 by an intended amount. This can therefore increase the amount of living tissue gripped with the clip 2, and the arms 2*b* can be held in the state wherein they are opened to the limit. Therefore, the operability can be improved.

Figure 37:
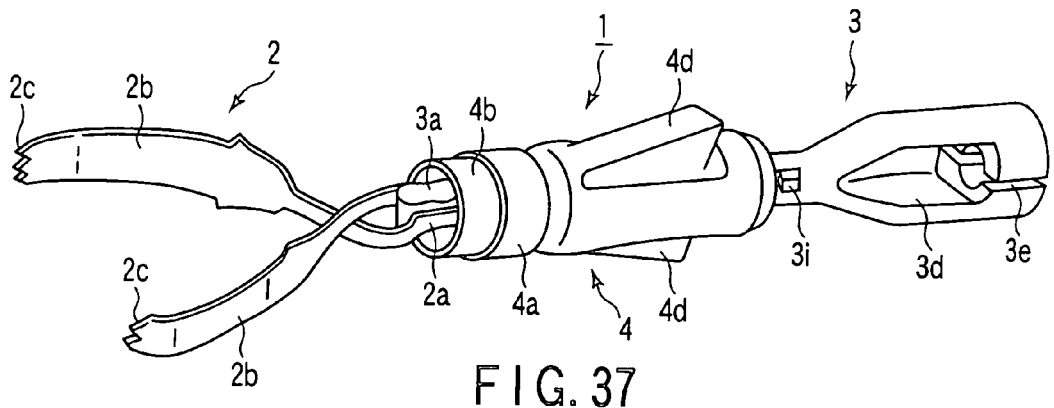
FIG. 37 is a perspective view of a clip unit according to the fifth embodiment of the present invention.

FIG. 37 shows the fifth embodiment. The same reference numerals as in the first embodiment denote the same constituent parts in the fifth embodiment, and a description thereof will be omitted. According to Jpn. Pat. Appln. KOKAI Publication No. 8-280701 described in the prior art, the clip, clamping ring, and coupling member are all formed by using a stainless steel material. According to Japanese Patent Application No. 2001-244402 as a previous application by the present applicant, only the clip is formed by using a stainless steel material, but the remaining members are formed by using a synthetic resin material.

If the clamping ring is formed by using a stainless steel material or by using a whitish resin without coloring it or changing its color, the color of the ring becomes near white. When illumination light from the endoscope strikes the ring, halation occurs, resulting in poor visibility.

If this resin is colored in a color similar to that of the tissue in the body cavity, the visibility of the clip, clip clamping ring, and coupling member become poor. This makes it difficult for an operator to approach the clip to a target region of the living tissue and reliably ligate the living tissue. This embodiment is directed to solve the above problem.

As shown in FIG. 37, the outer circumferential surface of a press tube 4 forming a clip unit 1 is colored in a color with good visibility within the visual field of the endoscope. A color with good visibility is a color different from that of the living tissue in the body cavity, e.g., blue or green. For example, red and white are preferably avoided because red or a similar color is almost the same color as that of the living tissue in the body cavity and provides poor visibility, and white causes halation upon application of illumination light from the endoscope. In addition, the outer circumferential surface of a coupling member 3 is colored in a color with good visibility within the visual field of the endoscope.

In the above embodiment, both the coupling member 3 and press tube 4 are colored in a color with good visibility within the visual field of the endoscope. It, however, suffices if at least one of the coupling member 3 and press tube 4 is colored, and the coupling member 3 and press tube 4 are colored in different colors. Although some effect can be obtained by coloring either coupling member 3 or the press tube 4, a more effect can be obtained by coloring the press tube 4 because the press tube 4 is indwelled in the body, together with a clip 2.

According to the clip unit 1 having the above arrangement, when the operator approaches the clip 2 to a target region of the living tissue while making observation with an endoscope 20, and presses tissue gripping portions 2*c* of the clip 2 against the target region, since the coupling member 3 and press tube 4 are colored in a color with good visibility within the visual field of the endoscope, e.g., blue or green, the operator can easily discriminate them from the living tissue in the body cavity, and can press the clip 2 against the target region of the living tissue without causing halation by light from the endoscope. The operator can therefore approach the clip 2 to the target region of the living tissue and reliably ligate the living tissue.

Figure 38:
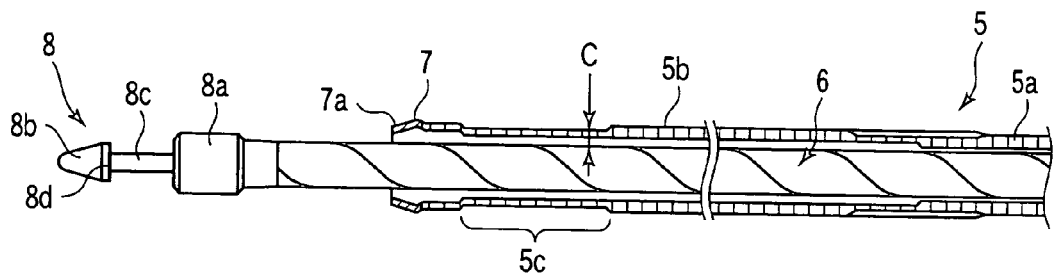
FIG. 38 is a partially cutaway side view of the distal end portion of a ligation device according to the sixth embodiment of the present invention.

FIG. 38 shows the sixth embodiment. The same reference numerals as in the first embodiment denote the same constituent parts in the sixth embodiment, and a description thereof will be omitted. According to Jpn. Pat. Appln. KOKAI Publication No. 8-280701 described in the prior art, the introduction tube is formed from a coil sheath having flexibility, and the operating wire formed from a stranded wire is made to retractably extend through the introduction tube. When the operating wire is moved forward by using the operator-side operating portion, the clip and clamping ring are made to protrude from the distal end opening of the introduction tube through the coupling member so as to open the arms of the clip. When the operating wire is moved backward, the clip is pulled into the clamping ring to close the arms of the clip, thereby ligating the living tissue.

The outer diameter of the operating wire is sufficiently smaller than the inner diameter of the introduction tube so as to allow the operating wire to easily move back and forth in the introduction tube. If, therefore, there is a clearance between the inner diameter of the introduction tube and the outer diameter of the operating wire, and the operating wire is moved back and forth by using the operator-side operating portion, the introduction tube may buckle by an amount corresponding to the clearance, and the forward/backward movement of the operating wire may not reliably transferred to the clip.

An endoscope is often used in a bent state, and the introduction tube also bends along the bent portion. If closing of the clip and fracturing of the coupling member are repeated in this state, the introduction tube may buckle. In addition, when the clip is made to protrude from the introduction tube, the operating wire meanders in the introduction tube, and the protrusion amount does not sufficiently reach the distal end of the sheath. This embodiment is directed to solve the above problem.

As shown in FIG. 38, a distal end chip 7 made of a metal such as stainless steel is provided at the distal end portion of a distal end coil 5b of an introduction tube 5. The distal end chip 7 is formed to have an outer diameter that allows it to extend through the channel of the endoscope, e.g., 2 mm to 6 mm, and an inner diameter that allows a clip unit 1 and operating wire 6 to extend through the distal end chip 7, e.g., about 2 mm. A chip inclined surface 7a having an angle of 5° to 90° is formed on the outer circumferential surface of the distal end chip 7 to gradually the diameter of the distal end chip 7.

The operating wire 6 is formed by using a stranded wire comprised of core and side strands of metal wires having appropriate elasticity, e.g., stainless steal or NiTi. The operating wire 6 has an outer diameter of 1.2 mm or more so as to set a clearance C with the inner diameter of the distal end coil 5b to 0.3 mm or less. In addition, the outer surface of the operating wire 6 is covered with a Teflon (registered trademark) coat. Reducing the clearance C with the inner diameter of the distal end coil 5b to 0.3 mm or less by thickening the operating wire 6 in this manner can prevent the introduction tube 5 from deforming and buckling.

According to this embodiment, since the clearance C between the inner diameter of the introduction tube 5 and the outer diameter of the operating wire 6 is small, the operating wire 6 meanders less, and the pushing force applied to the slider 11 can be efficiently transferred to the distal end side.

The fracturing force of the coupling member 3 is 20 N to 60 N. When the coupling member 3 fractures, compressing force similar to the fracturing force is also applied to the introduction tube 5. However, since the clearance C with the operating wire 6 is set to as small as 0.3 mm or less, the operating wire 6 acts as a reinforcing member to prevent the introduction tube 5 from buckling.

FIGS. 39A to 42 show the seventh embodiment. The same reference numerals as in the first embodiment denote the same constituent parts in the seventh embodiment, and a description thereof will be omitted. According to Jpn. Pat. Appln. KOKAI Publication No. 8-280701 and WO 01/10321A1 described in the prior art, the orientations of the clip and snare can be changed by rotating them by operating the operating portion. Since the structure for rotating the operating wire is used, a large torque cannot be obtained. In addition, the operating wire extending through the sheath must be basically fixed and rotated from outside, requiring a complicated structure.

In addition, in consideration of the transfer of torque and operability, it is necessary to rotate the operating wire near the forceps hole of the endoscope. In the case described in the above references, however, since the position of the rotating handle is fixed, a plurality of products with rotating handles fixed at different positions must be prepared for endoscopes having different lengths. This increases the manufacturing cost and causes confusion for the users. This embodiment is directed to solve the above problem.

Figure 39A:
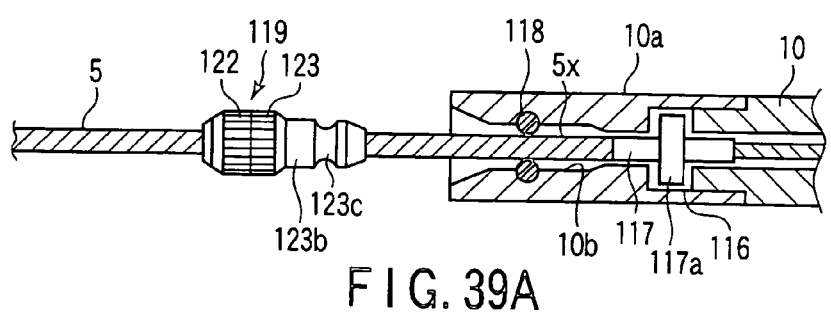
FIGS. 39A and 39B are partially cutaway side views respectively showing different states of the distal end portion of the operating portion body of a device according to the seventh embodiment of the present invention.
Figure 39B:
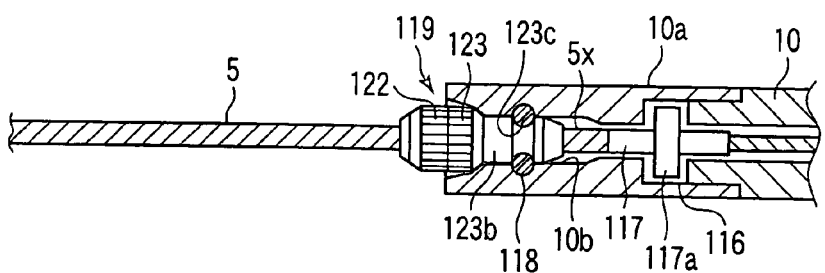
Figure 42:
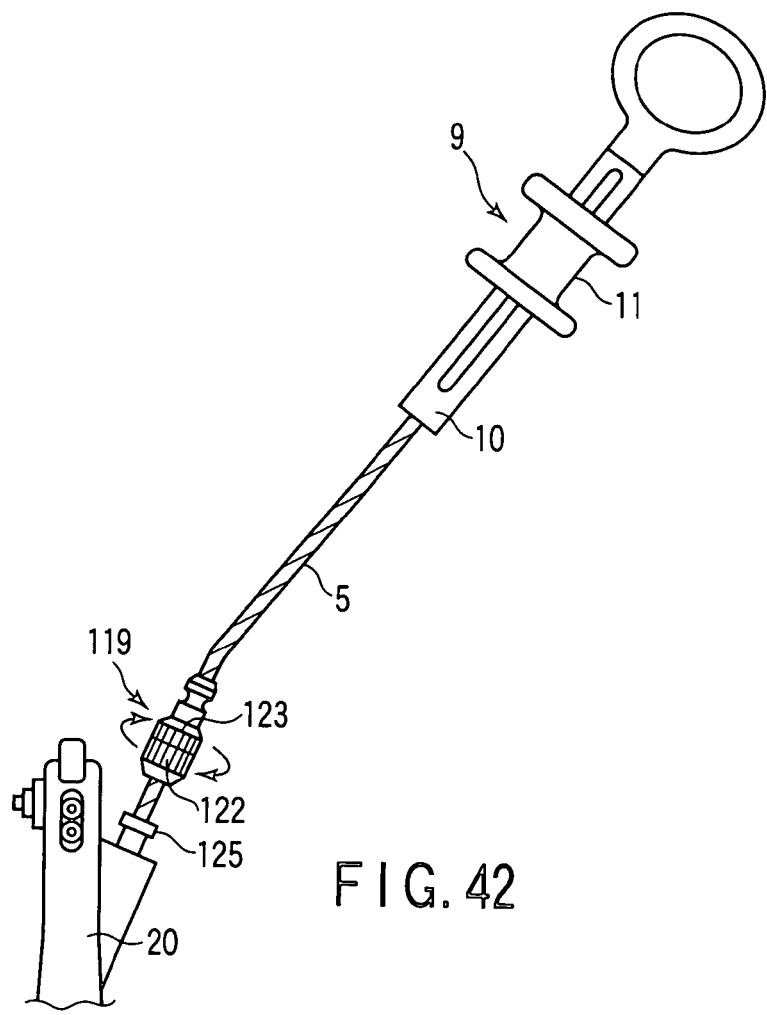
FIG. 42 is a view showing a state different from that in FIG. 41 to explain the function of the clip rotating operating portion according to the embodiment.

As shown in FIGS. 39A and 39B, an annular groove 116 is formed in the inner circumferential portion of the coupling portion between an operation portion body 10 and a cylindrical portion 10a. A collar portion 117a of a coil joint tube 117 made of a stainless steel material which couples an operator side end portion 5x of an introduction tube 5 to the operation portion body 10 is engaged with the annular groove 116. The coil joint tube 117 is rotatably provided for the operation portion body 10.

A diameter increasing portion 10b is formed on the inner circumferential portion of the distal end side of the cylindrical portion 10a of the operation portion body 10, and an O-ring 118 made of silicone rubber or the like is provided on the inner circumferential portion of the introduction tube 5 to have a function of fixing the rotating operating portion and operation portion body 10.

A clip rotating operating portion 119 is provided at a position closer to the distal end side than the cylindrical portion 10a of the operation portion body 10. As shown in FIG. 40, the clip rotating operating portion 119 is comprised of a grip tube 120 made of silicone rubber or the like which is fitted on the introduction tube 5, a grip tube body 121 which has a plurality of grip pawls 121a in the circumferential direction and slot grooves 121b between the grip pawls 121a in the axial direction and is fitted on the grip tube 120, a first grip 122 fitted on the distal end portion of the grip tube body 121, and a second grip 123 which is fitted on the proximal end portion of the grip tube body 121 and screwed into the first grip 122.

The first grip 122 has a tapered lumen 122a and female thread portion 122b in which the grip pawls 121a of the grip tube body 121 are fitted, and the outer circumferential surface of the first grip 122 is knurled. A male thread portion 123a with which the female thread portion 122b is threadably engaged is provided at the distal end portion of the second grip 123. The proximal end portion of the second grip 123 is provided with a cylindrical portion 123b which can be inserted into the diameter increasing portion 10b of the cylindrical-portion 10a. The cylindrical portion 123b is provided with a concave groove 123c which engages with the O-ring 118. In addition, the outer circumferential surface of the second grip 123 is knurled.

According to the clip rotating operating portion 119 having the above arrangement, when the operator rotates the second grip 123 while gripping the first grip 122 to fasten the male thread portion 123a to the female thread portion 122b, the grip tube body 121 decreases in diameter and can grip the introduction tube 5 through the grip tube 120. As a consequence, the clip rotating operating portion 119 is fixed to the introduction tube 5. When the clip rotating operating portion 119 is rotated, the introduction tube 5 and an operating wire 6 rotate, thereby changing the orientation of a clip 2.

When the male thread portion 123a is loosened with respect to the female thread portion 122b, since the grip tube body 121 increases in diameter, the clip rotating operating portion 119 becomes movable in the axial direction with respect to the introduction tube 5. The clip rotating operating portion 119 can therefore be moved to an arbitrary position. As shown in FIG. 41, therefore, while the introduction tube 5 is made to extend through the channel from the forceps opening 125 of the endoscope 20, the clip rotating operating portion 119 can be moved to the operation portion body 10 or can be moved to the introduction tube 5 near the forceps opening 125 to grip it, as shown in FIG. 41.

Making the clip rotating operating portion 119 grip the introduction tube 5 near the forceps opening 125 makes it possible to eliminate a torque loss, finely adjust the direction of the clip 2, and easily approach the clip 2 to the target region.

The function of the living tissue ligation device having the above arrangement will be described next. As in the first embodiment, the operator introduces the introduction tube 5 into the body cavity through a channel 21 of an endoscope 20 which is inserted into the body cavity in advance, and guides the distal end of the introduction tube 5 to a target region while observing the inside of the body cavity with the endoscope 20. The operator then moves the clip unit 1 forward in the introduction tube 5 through the operating wire 6 by pushing a slider 11 to the distal end side. When the slider 11 is further moved forward by using the operating wire 6, the clip unit 1 protrudes from the introduction tube 5 through a coil pipe 8. At this time, since each of retractable wings 4d of a press tube 4 is an inclined surface having a down grade toward the distal end side, the clip unit 1 is pushed out smoothly without any resistance. The retractable wings 4d of the press tube 4 are then released from the contact state with the inner surface of the introduction tube 5 and protrude from the press tube 4 in the outer circumferential direction. In addition, since a pair of arms 2b of the clip 2 have the property of spreading apart, they spread apart as soon as they protrude from the introduction tube 5.

Subsequently, when the slider 11 is moved to the proximal end side, the operating wire 6 is pulled back to the proximal end side, and the proximal end faces of retractable wings 4d of the press tube 4 are engaged with the end face of a distal end chip 7. Since the retractable wings 4d and distal end chip 7 are pressed against each other, a large frictional resistance is generated. If, therefore, the introduction tube 5 rotates, the clip unit 1 also rotates to follow up the rotation. In order to obtain a higher frictional resistance, the surface of the distal end chip 7 may be roughened or provided with projections.

When the slider 11 is further moved to the proximal end side to pull back the operating wire 6, a loop portion 2a of the clip 2 is pulled into the press tube 4 through the coupling member 3. As a projection 2d of the clip 2 comes into contact with an inner-diameter stepped portion 4f of the press tube 4, the arms 2b open to the limit.

In this state, the operator approaches the clip 2 to a target region of the living tissue while observing it, and presses tissue gripping portions 2c of the clip 2 against the target region. At this time, the clip 2 is rotated to change its direction as follows. As the clip rotating operating portion 119 is gripped and rotated in the direction indicated by the arrow, the introduction tube 5 and operating wire 6 are rotated. This makes it possible to finely adjust the direction of the clip 2 and easily approach it to the target region.

Figure 43:
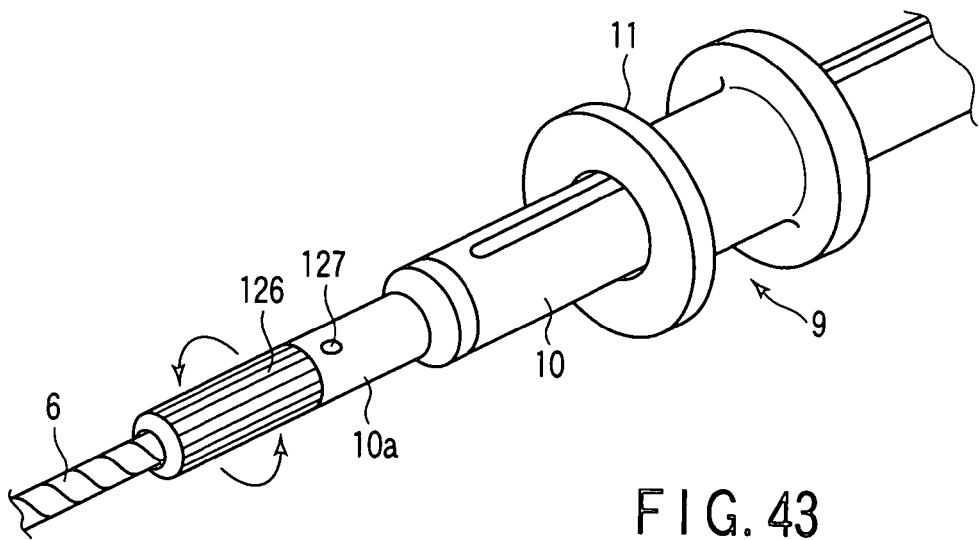
FIG. 43 is a perspective view of the operating portion of a device according to the eighth embodiment of the present invention.

FIGS. 43 to 44C show the eighth embodiment, which has the same object as that of the seventh embodiment. FIGS. 43 and FIGS. 44A to 44C show an operating portion 9. An operation portion body 10 is comprised of a cylindrical portion 10a on the distal end side, a shaft-like portion 10b extending to the proximal end side integrally with the cylindrical portion 10a, and a finger rest ring 10c rotatably provided on the proximal end portion of the shaft-like portion 10b. The shaft-like portion 10b of the operation portion body 10 is provided with a slit 10d extending along the axial direction. A slider 11 having a finger rest concave portion 11a is retractably fitted on the outer circumferential surface of the slit 10d.

The proximal end portion of the above operating wire 6 extending through the shaft-like portion 10b of the operation portion body 10 is introduced into a lumen 11b of the slider 11. A two-piece wire fixing member 12 is provided in the lumen 11b of the slider 11 at a position offset to the proximal end side. The proximal end portion 6b of the operating wire 6 is clamped and fixed by the two-piece wire fixing member 12. The wire fixing member 12 is fixed by a lid member 14 which is fixed to the slider 11 with screws 13.

A pipe 15 made of stainless steel is fitted on the operating wire 6 extending through the cylindrical portion 10a of the operation portion body 10. The fitting concave portion 10b is concentrically provided on the distal end portion of the cylindrical portion 10a. A fitting convex portion 126a of a rotating grip 126 is rotatably fitted in the fitting concave portion 10b. An annular groove 126b is provided on the outer circumferential surface of the fitting convex portion 126a. Fixing pins 127 extending vertically from the outer circumference of the cylindrical portion 10a in the radial direction are engaged with the annular groove 126b. Therefore, the rotating grip 126 is rotatably fitted in the cylindrical portion 10a. In addition, the outer circumferential surface of the rotating grip 126 is knurled.

An inner circumference large-diameter portion 128 is formed on the distal end portion of the rotating grip 126. A coil joint tube 129 fixed to the rotating grip 126 is fixed to the inner circumference large-diameter portion 128. The coil joint tube 129 is coupled to an operator-side coil 5a of the introduction tube 5.

Figure 45:
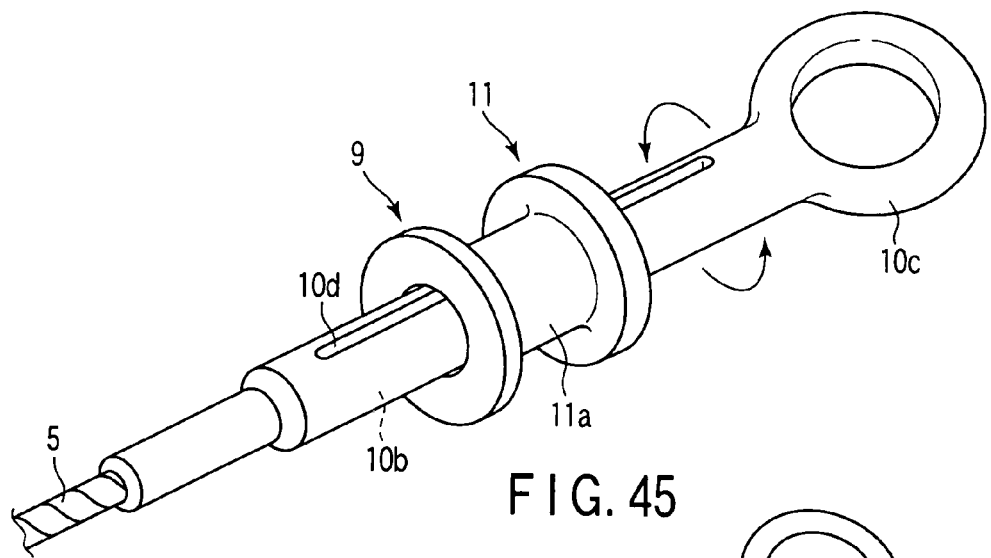
FIG. 45 is a perspective view of the operating portion of a device according to the ninth embodiment of the present invention.

FIGS. 45 to 46B show the ninth embodiment, which has the same object as that of the seventh embodiment. In the ninth embodiment, the proximal end portion of an introduction tube 5 is fixed to the distal end portion of a cylindrical portion 10a of an operation portion body 10, and an operating wire 6 extending through the introduction tube 5 extends to a slider 11.

A two-piece wire fixing member 12 is provided in a lumen 11b of the slider 11. A flat wire receiving member 6c integrally coupled to a proximal end portion 6b of the operating wire 6 is clamped and fixed by the two-piece wire fixing member 12. The wire fixing member 12 is fixed by a lid member 14 fixed to the slider 11 with screws 13.

Since the introduction tube 5 and operating wire 6 can be integrally rotated by rotating the operation portion body 10 in the direction indicated by the arrow in FIG. 45, a larger torque can be generated than when the introduction tube 5 is rotated alone. In addition, the direction of a clip 2 can be finely adjusted, and the operator can easily approach to a target region.

Figure 47:
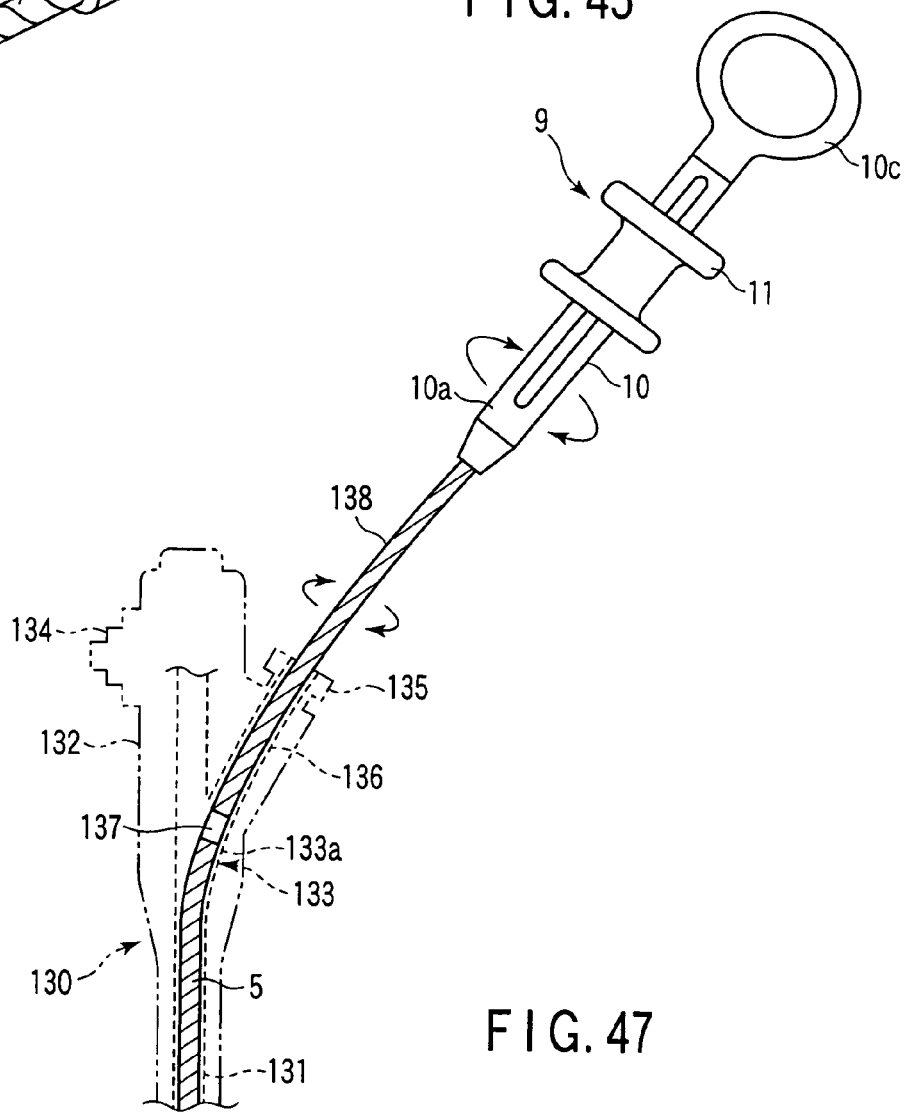
FIG. 47 is a side view of the operating portion of a device according to the 10th embodiment of the present invention.

FIG. 47 shows the 10th embodiment, which has the same object as that of the seventh embodiment. Referring to FIG. 47, the proximal end portion of a channel 131 incorporated in the insertion portion of an endoscope 130 is connected to a branch tube 133 inside an operating portion body 132. One tube of the branch tube 133 communicates with a push button 134 of the operating portion body 132, and the other tube communicates with a forceps opening 135. A connection tube 136 between a branch portion 133a of the branch tube 133 and the forceps opening 135 is formed to have a large inner diameter.

A large-diameter introduction tube 138 which can be inserted into the connection tube 136 is connected to the proximal end portion of the introduction tube 5 through a connection tube 137, thereby connecting the large-diameter introduction tube 138 to the operating portion body 132.

According to this embodiment, when the operating portion body 132 is rotated, the rotation can be transferred to the introduction tube 5 through the large-diameter introduction tube 138 with a large torque. As a consequence, the introduction tube 5 and an operating wire 6 (not seen in FIG. 47) integrally rotate in the direction indicated by the arrow. This makes it possible to finely adjust the orientation of the clip 2 and easily approach it to a target region.

According to the seventh to 10th embodiments described above, the introduction tube is rotated by using the clip rotating operating portion provided on the operator-side operating portion side of the introduction tube to change the orientation of the clip, thereby rotating the clip and approaching it to a target region. In addition, as compared with the case wherein the operating wire is rotated, this operation requires only a simple structure, and can generate a larger torque.

Figure 48A:
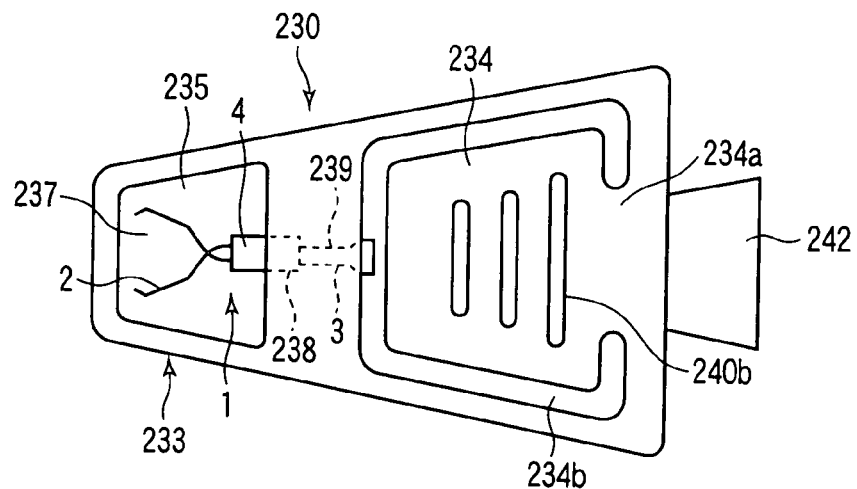
FIGS. 48A to 48C are a plan view showing a clip case according to the 11th embodiment of the present invention, a partially cutaway side view, and a partially cutaway side view showing a state wherein compressing portions are compressed by fingers.
Figure 48B:
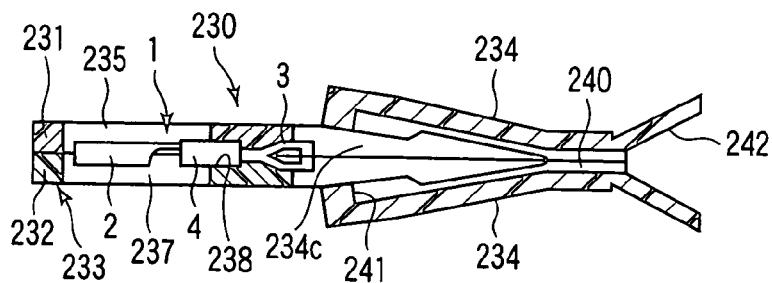
Figure 48C:
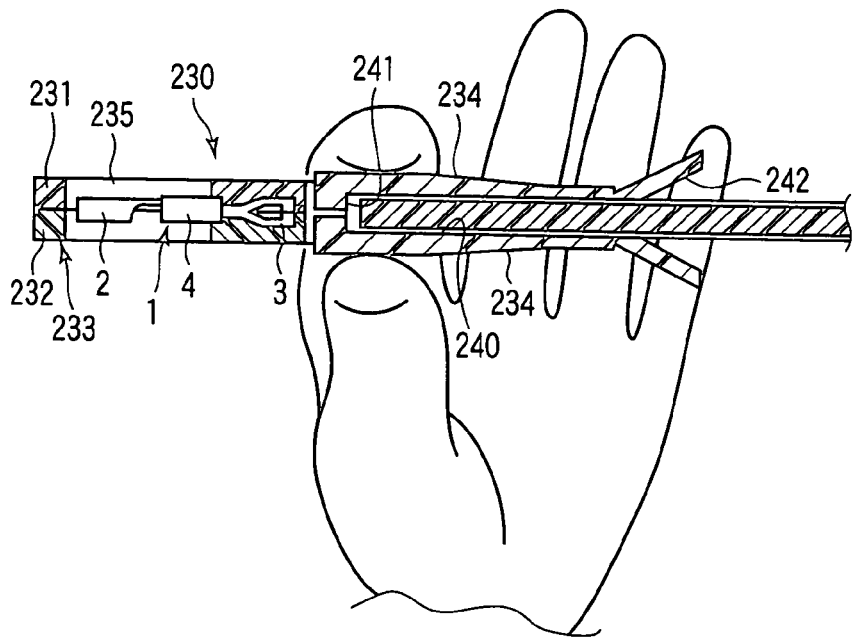
Figure 49:
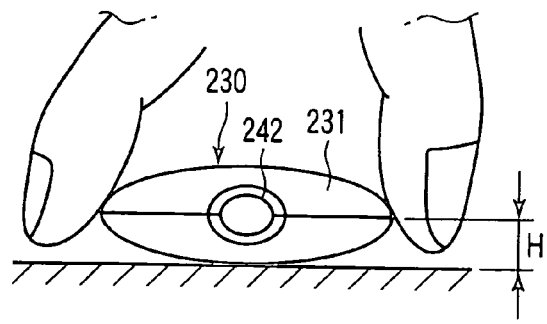
FIG. 49 is a front view of a clip case according to the embodiment.

FIGS. 48A to 49 show the 11th embodiment. The clip case in Japanese Patent Application No. 2001-244402 is formed by using a transparent synthetic resin material, and the clip unit is sterilized while being housed in the clip case. The clip unit can be connected to the operating wire extending through the introduction tube while being housed in the clip case without being touched by the fingers of the operator.

The above clip case is structured such that the introduction is pressed with the elastic restoring force of the elastic press portion provided in the clip case. This structure provides only insufficient holding power for the introduction tube. Therefore, the introduction tube is moved in a direction to come off the introduction tube insertion portion of the clip case by the reactive force generated when the arrowhead hook is elastically engaged with the coupling member by moving the operating wire forward. This makes it impossible to engage the arrowhead hook with the coupling member by one-touch operation.

If the elastic restoring force of the elastic press portion is increased to solve this problem, the insertion force required for the introduction tube also increases. By repeatedly mounting the clip on the introduction tube, an excessive load acts on the introduction tube. This may induce buckling of the introduction tube. This embodiment is directed to solve the above problem.

FIGS. 48A to 48C and FIG. 49 show a clip case 230 housing a clip unit 1. The clip case 230 is formed to have an almost trapezoidal shape in plan view by using upper and lower cases 231 and 232 having the same dimensions and same shape, which can be molded by the same mold. The upper and lower cases 231 and 232 are manufactured by injection-molding a transparent resin having appropriate hardness, e.g., ABS, PC, PP, PS, acrylic, or cycloolefin polymer. The clip case 230 is formed to have a size that allows the operator to easily hold it with his/her hand, having a width of about 10 mm to 20 mm, a length of about 50 mm, and a thickness of about 5 mm.

Clip unit housing portions 233 are provided at one end portion of the upper and lower cases 231 and 232 in the longitudinal direction, and compressing portions 234 are provided at the other end portion. A clip checking window 235 formed from a trapezoidal opening portion is provided at a portion corresponding to the clip unit housing portion 233. The compressing portions 234 are formed to have a trapezoidal shape with a size that is suitable for the operator to grip them with his/her fingers. A continuous slit 234b is formed in three side portions of each compressing portion 234 with a coupling portion 234a being left on one side portion. The clip case 230 is bent at the coupling portions 234a so that the compressing portions 234 of the upper and lower cases 231 and 232 are spaced apart from each other, and a spacing 234c is provided between the compressing portions 234.

When the compressing portions 234 of the upper and lower cases 231 and 232 are gripped with fingers, the compressing portions 234 elastically deform at the coupling portions 234a serving as fulcrums.

Since the upper and lower cases 231 and 232 have the same shape, only the lower case 232 will be described below. A clip housing portion 237 in which a clip 2 of a clip unit 1 is housed in the open state is provided on the inner surface of the clip unit housing portion 233. A press tube housing portion 238 and coupling member housing portion 239 which are formed from arcuated grooves are formed continuously with the clip housing portion 237. The bottom portion of the press tube housing portion 238 has a wing housing concave portion 238a in which retractable wings 4d are housed. An introduction tube insertion portion 240 formed from an arcuated groove is provided on the inner surface of the compressing portion 234 continuously with the coupling member housing portion 239. A plurality of convex strips 240b are provided on the outer surface of the compressing portion 234 to form an anti-slip portion. A stopper 234d protruding to the inner surface of the compressing portion 234 is provided at the inward end portion of the introduction tube insertion portion 240, and an insertion hole 242 is provided at the outward end portion of the introduction tube insertion portion 240. The insertion hole 242 has a tapered portion 242a which gradually increases in diameter toward the insertion inlet, allows the operator to identify the introduction tube insertion portion 240 with a glance, and designed to guide an introduction tube 5 into the insertion hole 242.

As shown in FIG. 49, the clip case 230 having the above arrangement is formed into an almost arcuated shape having a thick middle portion and two thin end portions. Therefore, when the clip case 230 is placed on a table or the like, a spacing H between the two end portions of the clip case 230 and the table becomes 1 mm or more, allowing the operator to easily pick up the clip case 230.

The function of the clip case having the above arrangement will be described next. The clip unit 1 is housed between the upper and lower cases 231 and 232 of the clip case 230, and the clip 2, a press tube 4, and a coupling member 3 are respectively set in the clip housing portion 237, press tube housing portion 238, and coupling member housing portion 239.

In order to attach the clip unit 1 to the ligation device in this state, first of all, as shown in FIG. 48B, the compressing portions 234 of the clip case 230 are gripped with fingers to reduce the spacing to some extent. In this state, the distal end portion of the introduction tube 5 is inserted into the introduction tube insertion portion 240 from the insertion hole 242 of the clip case 230 to abut against a distal end chip 7 against a stopper 241.

When the compressing portions 234 are gripped with fingers, the compressing portions 234 elastically deform to clamp and fix the introduction tube 5 between the inner surfaces of the compressing portions 234 so as not to allow the introduction tube 5 to move in the axial direction, as shown in FIG. 48C.

When a slider 11 of an operating portion 9 is moved to the distal end side in this state, an arrowhead hook 8 protrudes from the distal end portion of the introduction tube 5 through an operating wire 6. When, therefore, the distal end portion of the arrowhead hook 8 comes into contact with a conical hole 3*j* formed in a gripping portion 3*e* of the coupling member 3, and the slider 11 is further moved to the distal end side, the gripping portion 3*e* is spread outward by an arrowhead inclined portion 8*b*. As the arrowhead hook 8 is further pushed into the gripping portion 3*e* thereafter, the gripping portion 3*e* closes with its elastic force when it passes the arrowhead hook 8. As a consequence, a shaft portion 8*c* is clamped by the gripping portion 3*e*. In this state, an arrowhead large-diameter portion 8*d* of the arrowhead hook 8 is engaged with a stepped portion 3*m* of the gripping portion 3*e*, and hence the arrowhead hook 8 cannot be removed from the gripping portion 3*e*, thus coupling the clip unit 1 to the operating wire 6. When the slider 11 is moved to the proximal end side in this state, the clip unit 1 is pulled into the introduction tube 5 through the operating wire 6.

At this time, arms 2*b* of the clip 2 are closed in conformity with the inner diameter of the introduction tube 5. In addition, since retractable wings 4*d* of the press tube 4 are in contact with the inner surface of the introduction tube 5, they are elastically deformed and kept housed in the press tube 4.

When the force with which the compressing portions 234 of the clip case 230 are gripped is weakened after the clip unit 1 is pulled into the introduction tube 5, the compressing portions 234 spread apart in the vertical direction with the elastic restoring force. This allows the operator to remove the introduction tube 5 from the introduction tube insertion portion 240 of the clip case 230.

Figure 50A:
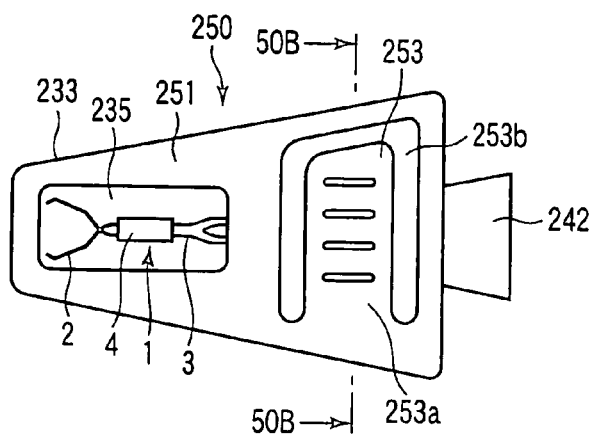
FIG. 50A is a plan view of the lower case of a device according to the 12th embodiment of the present invention.
Figure 50B:
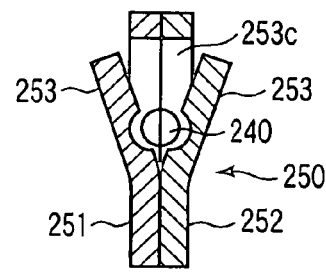
FIG. 50B is a sectional view taken along a line 50A-50A.

FIGS. 50A and 50B show the 12th embodiment. FIG. 50A is a plan view. FIG. 50B is a sectional view taken along a line 50B-50B of FIG. 50A. The same reference numerals as in the 11th embodiment denote the same constituent parts in the 12th embodiment, and a description thereof will be omitted.

Upper and lower cases 251 and 252 constituting a clip case 250 according to this embodiment are formed into translucent members with satin finished surfaces. Compressing portions 253 are provided in the right-angle direction with respect to the inserting direction of an introduction tube insertion portion 240. Each compressing portion 253 has a rectangular shape with a size that is suitable for the operator to grip it with his/her fingers, and a continuous slit 253*b* is formed in three side portions of the compressing portion 253 except for a one side on which a coupling portion 253*a* is left. The clip case is bent at the coupling portions 253*a* so as to separate the compressing portions 253 of the upper and lower cases 251 and 252 from each other, and a spacing 253*c* is provided between the compressing portions 253.

When the compressing portions 253 of the upper and lower cases 251 and 252 are gripped with fingers, the compressing portions 253 elastically deform at the coupling portions 253*a* serving as fulcrums. That is, when the compressing portions 253 are gripped with fingers, the compressing portions 253 elastically deform, and an introduction tube 5 can be clamped and fixed between the inner surfaces of the compressing portions 253 so as not to be movable in the axial direction.

Figure 51A:
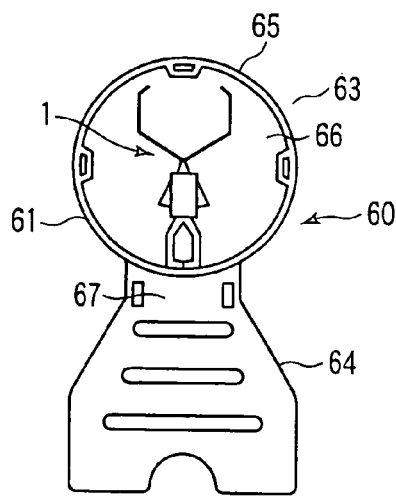
FIGS. 51A and 51B are a plan view and a side view of a lower case according to the 13th embodiment of the present invention.
Figure 51B:
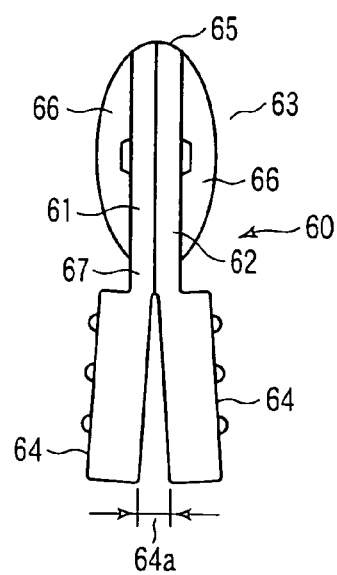

FIG. 51 shows the 13th embodiment. FIG. 51A is a plan view. FIG. 51B is a side view. The upper and lower cases 61 and 62 are manufactured by injection-molding a transparent resin having appropriate hardness, e.g., ABS, PC, PP, PS, acrylic, or cycloolefin polymer.

Clip unit housing portions 63 are provided at one end portion of the clip case 60, and compressing portions 64 are provided at the other end portion. Each clip unit housing portion 63 has an annular frame 65, and the frame 65 is provided with a clip checking window 66 formed from a lens. This allows an operator to observe a magnified view of a clip unit 1 housed in the clip unit housing portions 63.

The compressing portion 64 is formed almost trapezoidal in plan view. The clip case is bent at coupling portions 67 with the clip unit housing portions 63 so that the compressing portions 64 of the upper and lower cases 61 and 62 are spaced apart from each other, and a spacing 64*a* is provided between the compressing portions 64.

When, therefore, the compressing portions 64 of the upper and lower cases 61 and 62 are gripped with fingers, the compressing portions 64 elastically deform at the coupling portions 67 serving as fulcrums. When the compressing portions 64 are gripped with fingers, the compressing portions 64 elastically deform to allow an introduction tube 5 to be clamped and fixed between the inner surfaces of the compressing portions 64 so as not to allow the introduction tube 5 to be movable in the axial direction.

According to the 11th to 13th embodiments, when the compressing portions are compressed with fingers after the introduction tube through which the operating member extends is inserted into the insertion portion of the case body, the introduction tube is fixed to the case body. When the operating member is moved forward in this state, the distal end portion of the operating member engages with the coupling member of the clip unit housed in the case body. As a consequence, the operating member is coupled to the clip unit. In this manner, the operating member can be connected to the clip unit by one-touch operation.

According to each embodiment described above, the following arrangements can be obtained.

1. A ligation device can comprise a clip having arms which grip living tissue, a clamping member which is fitted and mounted on the clip to close the arms, a coupling member which can be inserted into the clamping member and engages with the clip, and an engaging portion which is provided for the coupling member and directly engages the clamping member with the coupling member while being fitted on the clamping member.

The engaging portion is preferably a noncircular portion formed on the shaft portion of the coupling member.

According to the above arrangement, when the clip unit is to be assembled, the coupling member is inserted into the clamping member, and the coupling member is pulled into the clamping member while the clip is engaged with the distal end portion of the coupling member. As a consequence, the clip is housed in the clamping member, and the clamping member is directly engaged with the coupling member to prevent the coupling member from accidentally moving in the clamping member. This makes it possible to prevent the clip from separating from the coupling member inside the clip case or introduction tube.

2. A ligation device can comprise a clip having arms which grip living tissue, a clamping member which is fitted and mounted on the clip to close the arms, a coupling member which can be inserted into the clamping member and engages with the clip, and lock portions which are provided for both the clip and the clamping member and are directly engaged to hold the arms of the clip in an open state.

The lock portions are preferably projections provided for the clip and an inner-diameter stepped portion provided for the clamping member.

According to this arrangement, when the clip is pulled into the clamping member by using the operating member, and the arms of the clip open to the limit, the lock portions of the clip and clamping member engage to hold the clip in the state wherein it opens to the limit. By bringing the clip into contact with the living tissue in this state and closing the clip, the living tissue can be gripped with the clip.

3. A ligation device is a living tissue ligation device which includes a clip having arms which grip living tissue and a clamping member which is fitted and mounted on the clip to close the arms, is endoscopically inserted into a body cavity, and ligates the living tissue with the clip. The clamping member can be colored in a color with good visibility within the visual field of the endoscope.

The clamping member is preferably colored in a color different from that of the tissue in the body cavity.

The clamping member is preferably colored in blue or green.

The clamping member is preferably colored in a color other than white.

4. A ligation device is a living tissue ligation device which comprises a clip having arms which grip living tissue, a clamping member which is fitted and mounted on the clip to close the arms, and a coupling member which is coupled to the clip, is endoscopically inserted into the body cavity, and ligates the living tissue with the clip. The coupling member can be colored in a color with good visibility within the visual field of the endoscope.

The coupling member can be colored in a color different from that of the tissue in the body cavity.

The coupling member can be colored in blue or green.

The coupling member can be colored in a color other than white.

According to any one of the arrangements described above, since the clamping member and coupling member are colored in a color different from that of the tissue in the body cavity, the visibility of the clamping member and coupling member improve within the visual field of the endoscope. This makes it possible to approach the clip to a target region of the living tissue and reliably ligate the living tissue.

5. A ligation device preferably includes a clip having arms which grip living tissue, a clamping member which is fitted and mounted on the clip to close the arms, a coupling member which can be inserted into the clamping member and engages with the clip, an introduction tube which can house the clip and clamping member, and an operating member which is engaged with the coupling member and is made to retractably extend through the introduction tube. The clearance between the inner diameter of the introduction tube and the outer diameter of the operating member is preferably set to 0.3 mm or less.

The introduction tube is preferably formed from a coil sheath having flexibility around which a spring material is tightly wound.

The operating member is preferably formed from an operating wire made of a stranded wire.

According to any one of the arrangements described above, since the clearance between the inner diameter of the introduction tube and the outer diameter of the operating member is very small, the introduction tube does not buckle when the operating member is moved back and forth, and the back-and-forth moving operation of the operating member can be reliably transferred to the clip.

6. A ligation device can comprise a clip having arms which grip living tissue, a clamping member which is fitted and mounted on the clip to close the arms, a coupling member which can be inserted into the clamping member and engages with the clip, a coupling member which engages with the clip, an introduction tube which can house the clip and clamping member, an operating member which is made to retractably extend through the introduction tube, and a clip rotating operating portion which is provided on the operator-side operating portion side of the introduction tube and changes the orientation of the clip by rotating the introduction tube.

The clip rotating operating portion is preferably able to move in the axial direction of the introduction tube.

According to the above arrangement, when the clip rotating operating portion is rotated, the introduction tube and operating member are rotated. This makes it possible to rotate the clip and allow the operator to approach it to a target region.

7. A case for a living tissue ligation clip which houses a clip unit preferably includes a case body which comprises a clip having arms which grip living tissue, a clamping member which is fitted and mounted on the clip to close the arms, and a coupling member which can be inserted into the clamping member and engages with the clip, the case body being provided with a clip unit housing portion, an insertion portion which is provided for the case body and in which an introduction tube connected to the coupling member is inserted, and compressing portions which are provided at portions of the case body and fix the introduction tube by compressing the introduction tube inserted into the insertion portion.

The case body preferably has a shape having a middle portion which is thicker than two end portions.

The insertion portion preferably has an tapered insertion hole whose diameter on the inlet side is increased.

The case body can have an opening window which is formed in part of the case body to allow the user to check the clip housed therein.

According to the case having any one of the above arrangements, when the compressing portions are compressed with fingers after the introduction tube through which the operating member extends is inserted into the insertion portion of the case body, the introduction tube is fixed to the case body. When the operating member is moved forward in this state, the distal end portion of the operating member engages with the coupling member of the clip unit housed in the case body, thereby coupling the operating member to the clip unit.

Figure 52:
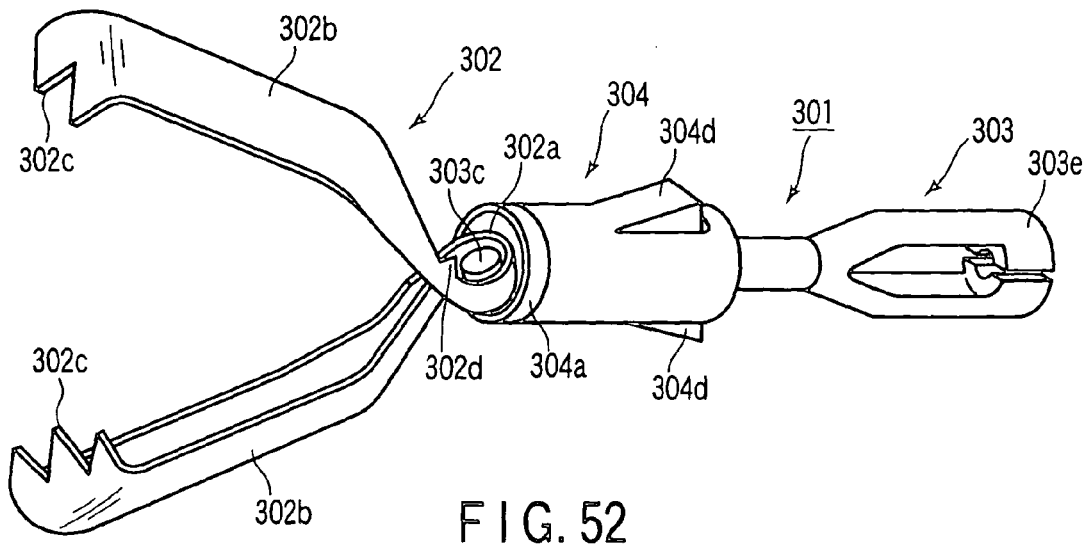
FIG. 52 is a perspective view of a clip unit according to the 14th embodiment of the present invention.

The 14th embodiment will be described below with reference to FIGS. 52 to 64D. FIG. 52 is a perspective view of a clip unit 301 of a living tissue ligation device. The clip unit 301 is comprised of a clip 302, a coupling member 303, and a press tube 304 serving as a clamping member.

Figure 53A:
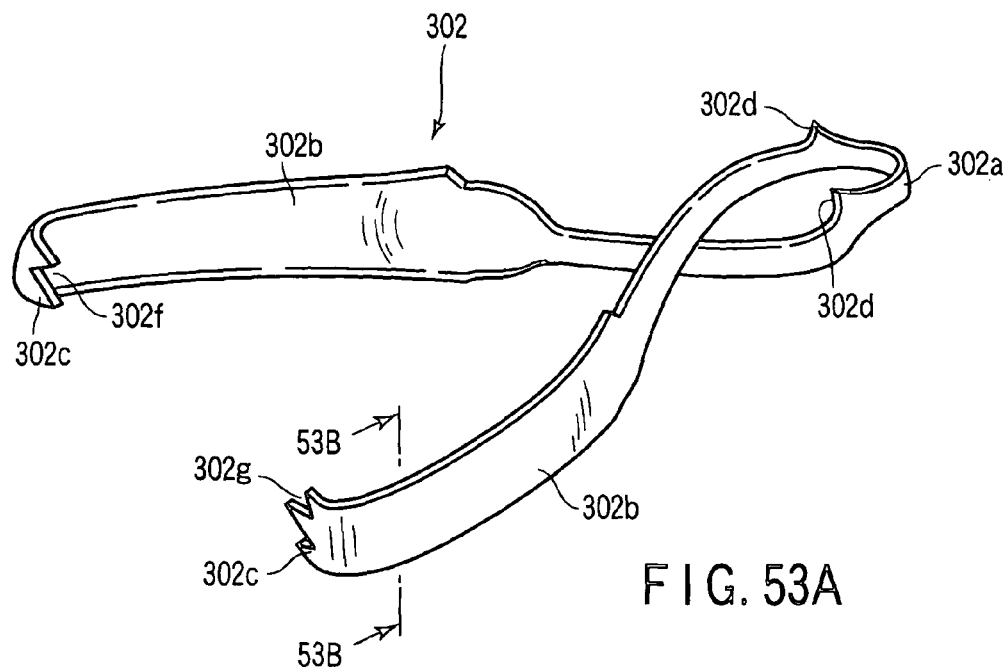
FIG. 53A is a perspective view of a clip according to the embodiment.
Figure 53B:
FIG. 53B is a sectional view taken along a line 53B-53B of FIG. 53A.

As shown in FIGS. 53A and 53B, the clip 302 has a loop portion 302a formed by, for example, bending a metal plate member such as a leaf spring member made of stainless steel or the like at its middle portion. In addition, a pair of arms 302b having the property of spreading apart are made to intersect at a position near the loop portion 302a and extend with their distal end portions spaced apart from each other. Tissue gripping portions 302c are formed on the distal end portions of the arms.

The intersecting portion of the arms 302b of the clip 302 is formed to have a width smaller than that of the distal end portions, and the tissue gripping portions 302c are formed at the distal ends so as to face each other. The proximal end portion of the loop portion 302a of the arms 302b is formed to have a width smaller than those of the remaining portions, and sawtooth-like projections 302d protruding in the widthwise direction are provided on the two side portions of the loop portion 302a. Each projection 302d is formed to have an inclined surface with an acute angle on the tissue grip portion side and an obtuse angle on the loop portion side such that the projection slidably moves on the inner surface of the press tube 304 in the direction in which the clip 302 is pulled into the press tube 304 and bites into the inner surface of the press tube 304 in the direction opposite to the pulling direction.

The arms 302b are formed to have almost arcuated cross-sections conforming to the curvature of the channel of an endoscope (to be described later). When the clip 302 is closed, the pair of arms 302b form an almost cylindrical shape to allow the clip 302 to directly extend through the channel.

Each tissue gripping portion 302c is bent inwardly at 90° to 150° into a spherical shape. One of the tissue gripping portions 302c is formed into an almost triangular convex portion 302f, whereas the other portion is formed into an almost triangular concave portion 302g which meshes with the convex portion 302f.

The dimensions of the clip 302 will be described. The size of the clip is set in consideration of gripping ability for the living tissue and insertion into an endoscope. For example, the clip has a thickness of 0.1 mm to 0.5 mm and a total length of 5 mm to 10 mm. The loop portion 302a has a circular or elliptic shape having a major axis length of 1 mm to 5 mm and a minor axis length of 1 mm to 5 mm. Each tissue gripping portion 302c has a length of about 1 mm and a width of about 1 to 2 mm. Each projection 302d has a width that allows the clip 302 to be pulled into the press tube 304 and a distal end tube (to be described later), i.e., a width of 1 mm or more. The radius of each arm 302b is set to 1 mm to 1.303 mm.

As shown in FIGS. 54A and 54B, the coupling member 303 is manufactured by injection-molding a high-strength resin material such as a liquid crystal polymer or nylon, and has a cylindrical, rodlike shape. A projection portion 303a is provided on the distal end portion of the coupling member. The projection portion 303a protrudes from a proximal portion 303b to a side. A width 303c of the projection portion 303a is about 0.6 mm to 1.2 mm. The clip 302 can be closed by hooking the loop portion 302a of the clip 302 on the projection portion 303a and pulling the clip 302 into the press tube 304.

The other end portion of the coupling member 303 is bifurcated, and a gripping portion 303e which has a notched portion 303d and is used to grip an arrowhead hook (to be described later) is formed at the bifurcated portion. The intermediate portion of the coupling member 303 is formed into a small-diameter portion 303f serving as a fracture portion, an intermediate-diameter portion 303g, and a large-diameter portion 303h which extend from the distal end side to the proximal end side. The dimensions of small-diameter portion 303f are so set as to fracture when a fracturing force of 20 N to 60 N is applied thereto. Flat surfaces 303j are formed on the opposing surfaces of the large-diameter portion 303h along the axial direction. That is, the large-diameter portion 303h is formed into a noncircular shape. Lock projections 303i are provided on portions of the outer circumferential surface of the large-diameter portion 303h at the terminal portions of the flat surface portions 303j.

The dimensions of the coupling member 303 will be described. The coupling member 303 has a total length of about 10 mm. The gripping portion 303e has an inner diameter of 0.6 mm. The small-diameter portion 303f has an outer diameter of 0.303 mm or more. The large-diameter portion 303h has a diameter of 1 mm to 1.303 mm. The height of the lock projection 303i is set to 0.1 mm or more.

The press tube 304 is manufactured by injection-molding a material softer than the clip 302, for example, a high-rigidity resin having appropriate elasticity such as PPA (polyphthalamide) or PA (polyamide). The press tube 304 serves to close the arms 302b of the clip 302 when the press tube 304 is fitted on the arms 302b of the clip 302.

A distal end tube 304a made of a high-strength metal such as stainless steel is fitted on the distal end portion of the press tube 304. The outer diameter of the distal end tube 304a is equal to that of the press tube 304. An inclined surface 304c is formed on the inside of the distal end tube 304a so as to gradually increase its inner diameter from a smallest-diameter portion 304b of the proximal end portion to the distal end portion. In addition, an inclined surface 304c' is formed on the outer circumference of the distal end tube 304a to gradually decrease its outer diameter toward the distal end portion, thereby allowing the distal end tube 304a to smoothly slide on the inside of the channel of the endoscope.

A pair of retractable wings 304d which are elastically retractable in the radial direction are provided on the outer circumferential portion of the press tube 304. In addition, an inclined surface 304e is provided on the rear end portion of the press tube 304. The inner diameter of the distal end side of the press tube 304 is slightly larger than that of the rear end side so as to form an inner-diameter stepped portion 304f therebetween.

The dimensions of the press tube 304 will be described. The total length and inner and outer diameters of the press tube 304 are set in accordance with the size of the clip 302. The inclined surface 304c on the inside of the distal end tube 304a has an angle of 15 to 90° and an entrance diameter of about 1.6 mm, which are suitable for allowing the clip 302 to grip the tissue. The outside inclined surface 304c' has an angle of 5 to 120°, and is designed to come into surface contact with the bent channel of the endoscope. The retractable wings 304d are almost triangular and have a maximum protrusion width 304g of 2 mm or more, which is equal to or more than the inner diameter of the channel.

The level difference between the rear end inclined surface 304e of the press tube 304 and the large-diameter portion 303h of the coupling member 303 is set to 0.5 mm or less, and the height of the inner-diameter stepped portion 304f is set to 0.1 mm or more.

The assembly of the clip unit 301 will be described next. The coupling member 303 is inserted from the rear end side of the press tube 304, and the projection portion 303c of the coupling member 303 is made to completely protrude from the distal end tube 304a of the press tube 304. In this state, the loop portion 302a of the clip 302 is hooked on the projection portion 303c. The coupling member 303 is then pulled to the operator side to make the loop portion 302a of the clip 302 come into contact with the distal end tube 304a of the press tube 304, thus completing the assembly of the clip unit 301.

Figures 55A, 55B, 55C:
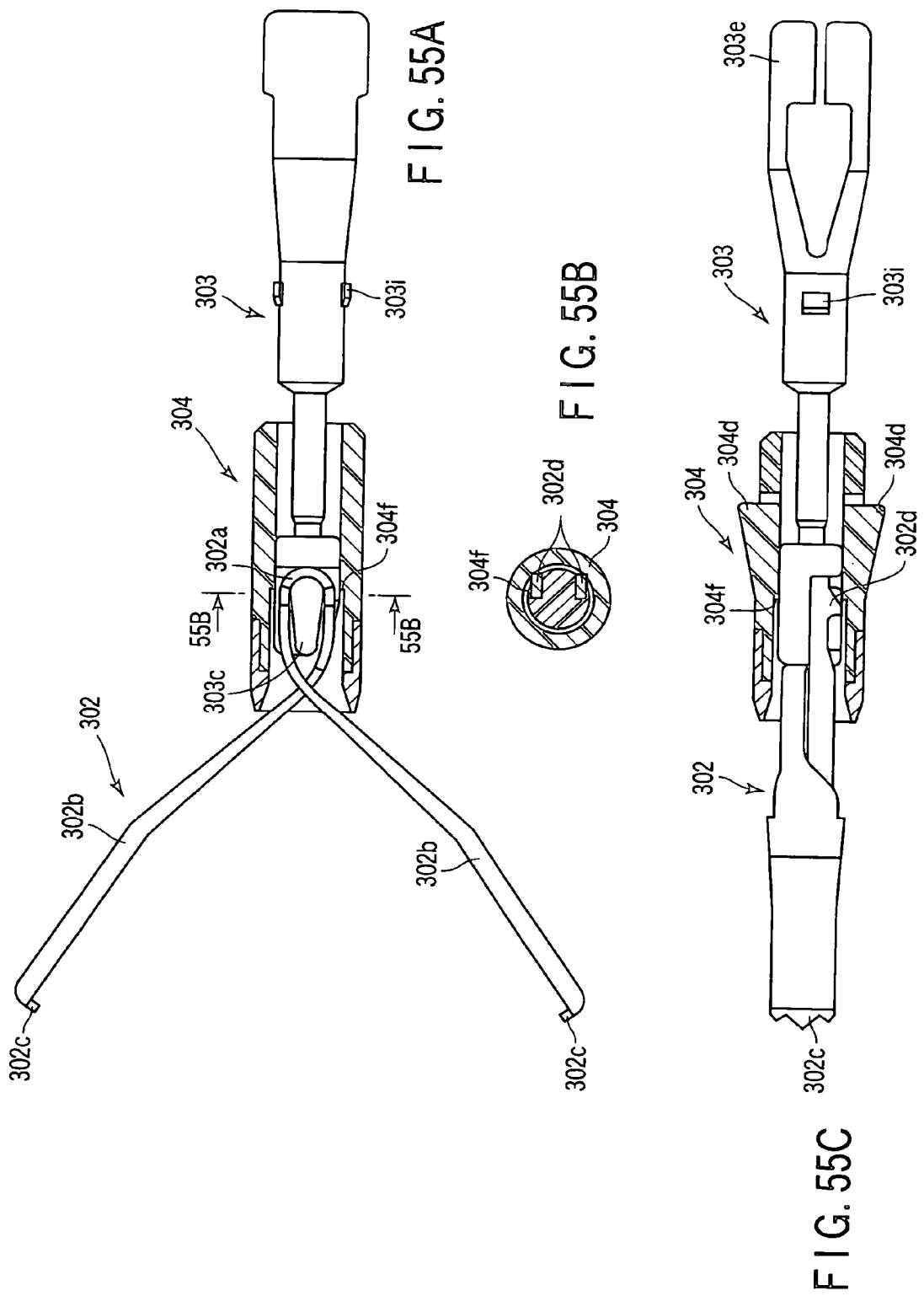
FIG. 55A is a partially cutaway side view showing the clip unit in a state wherein the clip according to the embodiment is open.
FIG. 55B is a sectional view taken along a line 55B-55B of FIG. 55A.
FIG. 55C is a partially cutaway front view showing the clip unit in a state wherein the clip according to the embodiment is open.
Figure 58A:
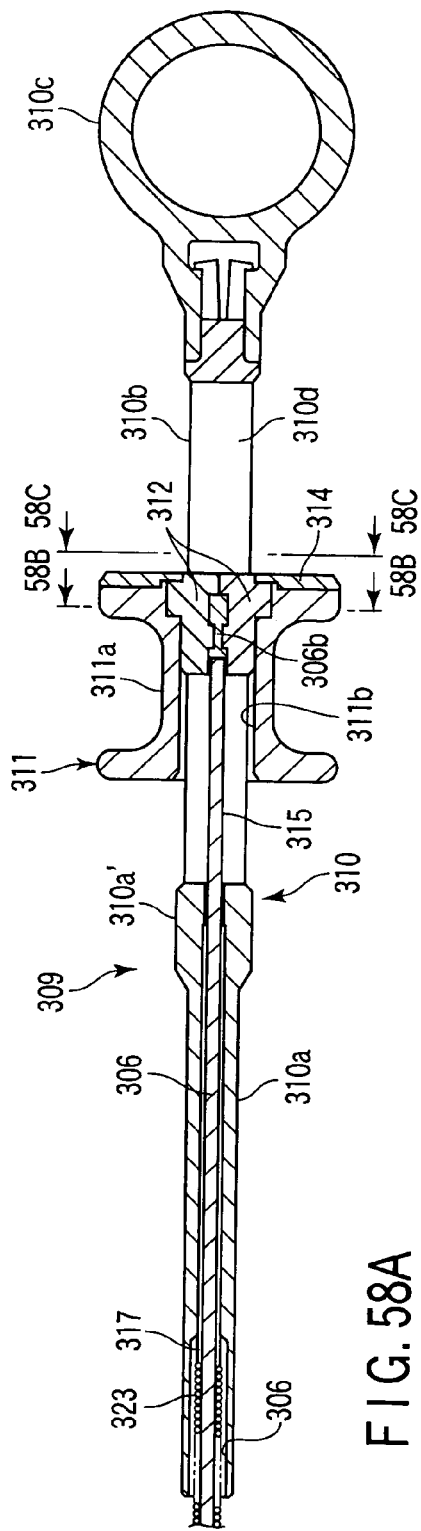
FIG. 58A is a longitudinal sectional side view of the operating portion of the ligation device according to the embodiment.
Figure 58B:
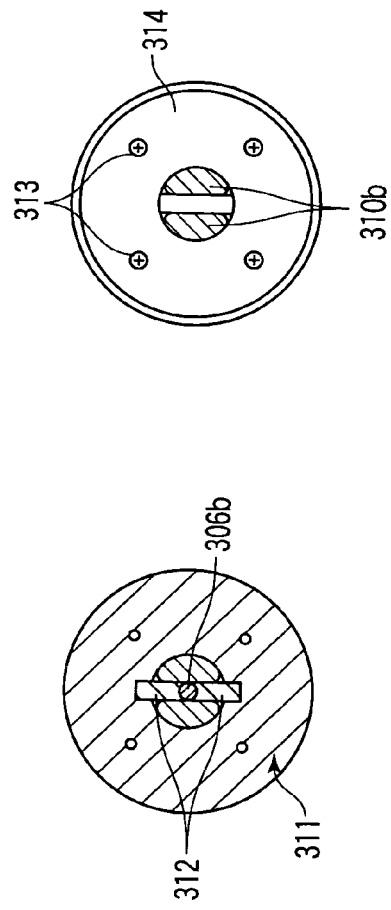
FIG. 58B is a sectional view taken along a line 58B-58B of FIG. 58A.
Figure 58C:
FIG. 58C is a sectional view taken along a line 58C-58C of FIG. 58A.
Figure 59A:
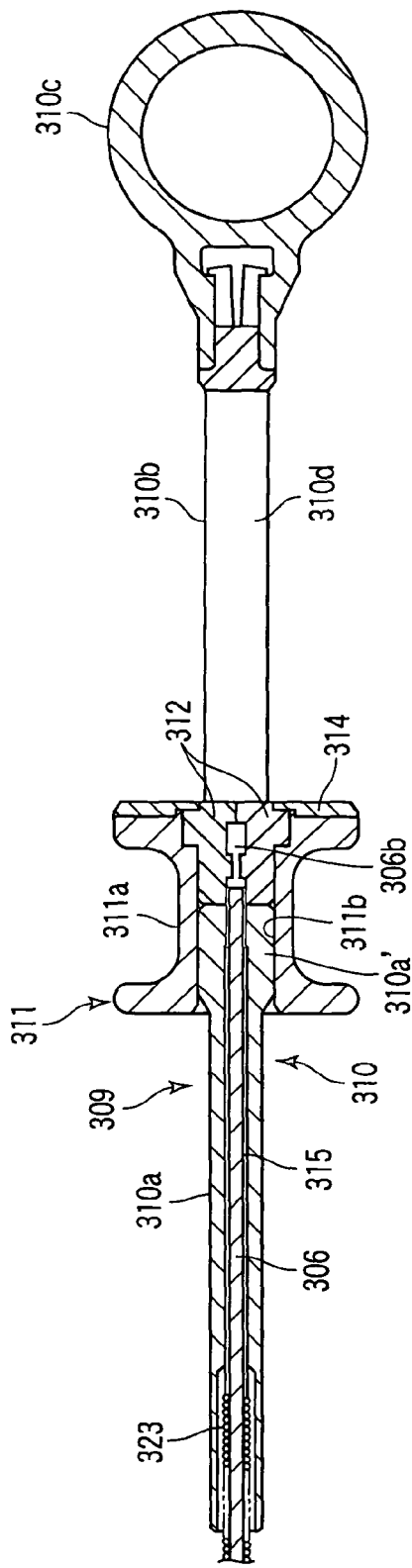
FIGS. 59A and 59B are sectional views respectively showing the operating portion of the ligation device according to the embodiment at different operating positions.
Figure 59B:
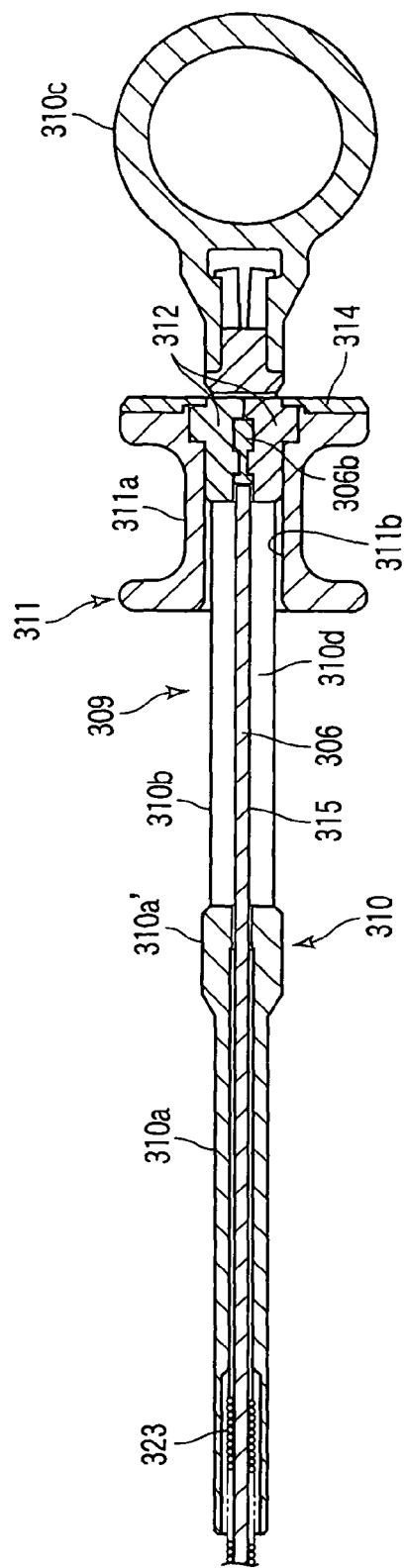
Figure 62A:
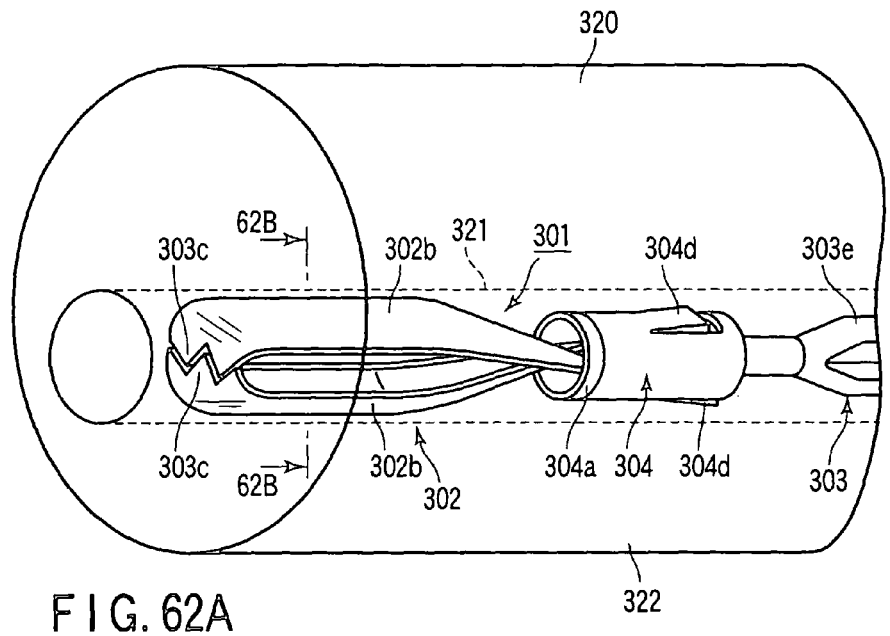
FIG. 62A is a perspective view of a clip unit inserted in the channel of the endoscope according to the embodiment.
Figure 62B:
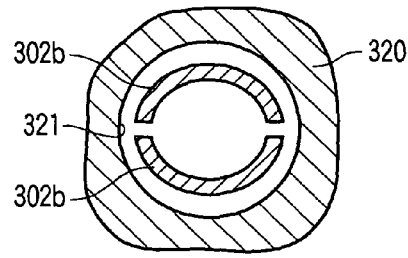
FIG. 62B is a sectional view taken along a line 62B-62B of FIG. 62A.

When the coupling member 303 is pulled to the operator side in this state, the loop portion 302a of the clip 302 is pulled into the press tube 304, and the loop portion 302a is flattened. As a consequence, the arms 302b spreads apart. At this time, as shown in FIGS. 55A to 55C, the clip 302 is held in the state wherein it opens to the limit, because the projections 302d of the clip 302 are locked to the inner-diameter stepped portion 304f of the press tube 304. When the coupling member 303 is pulled to the operator side in this state, the projections 302d of the clip 302 move over the inner-diameter stepped portion 304f of the press tube 304, and the clip 302 is pulled into the coupling member 403. As a consequence, as shown in FIGS. 56A and 56B, the arms 302b of the clip 302 close.

At this time, since the press tube 304 is formed from a resin having appropriate elasticity which is softer than the clip 302, the projections 302d of the clip 302 bite into the inner wall of the press tube 304. This restricts the clip 302 from moving in the press tube 304 in the axial direction, thus keeping it in the closed state.

Since the projections 302d of the clip 302 are formed into a sawtooth-like shape protruding in the widthwise direction of the loop portion 302a, the clip 302 can slightly move to the clamping side (the direction to close the arms 302b), but cannot move to the return side (the direction to open the arms 302b) because the projections 302d bite into the inner wall of the press tube 304.

The connecting structure between the coupling member 303 and an operating wire 306 shown in FIGS. 57A to 57C will be described next. The operating wire 306 is formed by using a stranded wire comprised of core and side strands of metal wires having appropriate elasticity, e.g., stainless steal or NiTi. The operating wire 306 has an outer diameter of 1.2 mm to 1.8 mm, and a clearance of 0.4 mm or less with the inner diameter of the channel of the endoscope. The outer surface of the operating wire 306 is covered with a Teflon (registered trademark) coat.

A cylindrical wire fixing portion 308a made of a metal material such as stainless steel is fitted on the distal end portion of the operating wire 306. An arrowhead hook 308 is provided on the wire fixing portion 308a through a shaft portion 308c. A fixing hole 308e is formed in the wire fixing portion 308a. The wire fixing portion 308a is fixed to the operating wire 306 by pouring a brazing material into the fixing hole 308e.

The arrowhead hook 308 has an arrowhead inclined portion 308b formed at the distal end portion of the shaft portion 308c and having a conical shape and an angle of 10° to 120°. An arrowhead large-diameter portion 308d has a diameter of about 0.8 mm to 1.2 mm.

FIGS. 58A to 60 show an operating portion 309. An operating portion body 310 is comprised of a cylindrical portion 310a on the distal end side, a shaft-like portion 310b extending to the proximal end side integrally with the cylindrical portion 310a, and a finger rest ring 310c rotatably provided on the proximal end portion of the shaft-like portion 310b. A slit 310d is provided for the shaft-like portion 310b of the operating portion body 310 in the axial direction. A slider 311 having a finger rest concave portion 311a on its outer circumferential surface is retractably provided in the slit 310d.

The proximal end portion of the operating wire 306 extending through the cylindrical portion 310a of the operating portion body 310 is introduced into a lumen 311b of the slider 311. A two-piece wire fixing member 312 is provided at a position offset to the proximal end side of the lumen 311b of the slider 311. A proximal end portion 306b of the operating wire 306 is clamped and fixed by the two-piece wire fixing member 312. The wire fixing member 312 is fixed to the slider 311 by a lid member 314 fixed with screws 313.

When, therefore, the slider 311 is moved back and forth with respect to the operation portion body 310, the operating wire 306 is moved back and forth in the channel of the endoscope. Since the distal end side of the lumen 311b of the slider 311 is open, when the slider 311 is moved forward to the limit, a proximal end large-diameter portion 310a' of the cylindrical portion 310a of the operation portion body 310 is fitted in the slider 311. This makes it possible to increase the stroke of the slider 311 while decreasing the length of the operating portion 309.

Although the wire fixing member 312 is provided at the position offset to the proximal end side of the lumen 311b of the slider 311, the same effect as described above can be obtained even by providing the wire fixing member 312 at a position offset to the distal end side of the lumen 311b of the slider 311.

A pipe 315 made of stainless steel is fitted on the operating wire 306 which extends through the cylindrical portion 310a of the operation portion body 310. An inner circumference large-diameter portion 316 is formed at the distal end portion of the cylindrical portion 310a, and a coil joint tube 317 fixed to the cylindrical portion 310a is fixed to the inner circumference large-diameter portion 316.

The proximal end portion of a coil sheath 23 fitted on the operating wire 306 is coupled to the coil joint tube 317. The coil sheath 323 has a length of 200 mm to 300 mm. A forceps opening fixing portion 324 is provided at the distal end portion of the coil sheath 323. The forceps opening fixing portion 324 is detachably fixed to a forceps opening 329 formed in an operating portion 325 of an endoscope 320. The lumen of the coil sheath 23 communicates with a channel 321 of the endoscope 320.

The proximal end portion of the operating wire 306 is connected to the slider 311 of the operating portion 309. The operating wire 306 is guided to the distal end portion of the channel 321 upon extending through the coil sheath 323, and channel 321. The distal end portion of the operating wire 306 is engaged with and connected to the coupling member 303 of the clip unit 301 through the arrowhead hook 308.

The reactive force applied to the operating portion body 310 when the slider 311 of the operating portion 309 is moved back and forth can be received by the operating portion 325 of the endoscope 320 through the coil sheath 23, thereby opening/closing the arms 302b of the clip 302 through the operating wire 306.

The function of the living tissue ligation device having the above arrangement will be described next.

As shown in FIGS. 61A to 62B, the clip unit 301 is introduced into the body cavity through the operating wire 306 in the channel 321 of the endoscope 320 which is inserted into the body cavity in advance. The operator then guides the clip unit 301 to a target region while observing the inside of the body cavity with the endoscope 320.

FIGS. 62A to 63C show a sequence of ligating the living tissue by using the clip 302. When the slider 311 is pushed out to the distal end side, the clip unit 301 moves forward in the channel 321 through the operating wire 306, as shown in FIG. 63A. When the operating wire 306 is further moved forward by using the slider 311, the clip unit 301 protrudes from the channel 321, as shown in FIG. 63B. At this time, since each retractable wing 304d of the press tube 304 has an inclined surface with a down grade toward the distal end side, the clip unit 301 is pushed out smoothly without any resistance. The retractable wings 304d of the press tube 304 are then released from the contact state with the inner surface of the channel 321, and protrude from the press tube 304 in the outer circumferential direction. As shown in FIG. 64A, since the pair of arms 302b of the clip 302 have the property of spreading apart, they spread apart as soon as they protrude from the channel 321.

Figure 63A:
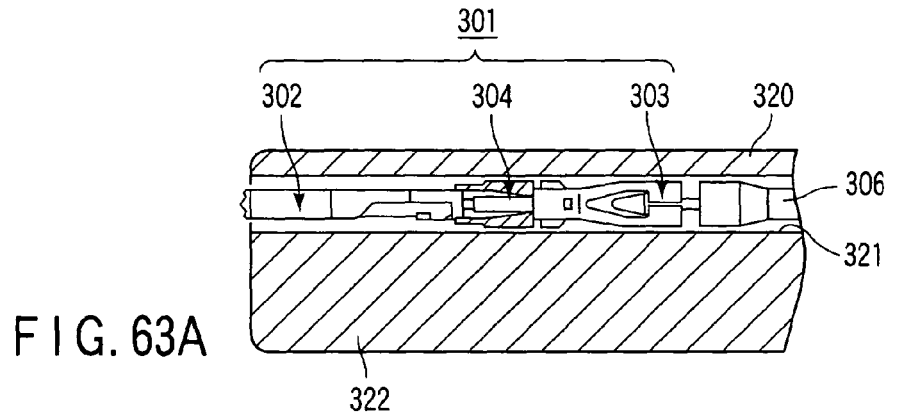
FIGS. 63A to 63C are views for explaining the operation of the device according to the embodiment.
Figure 63B:
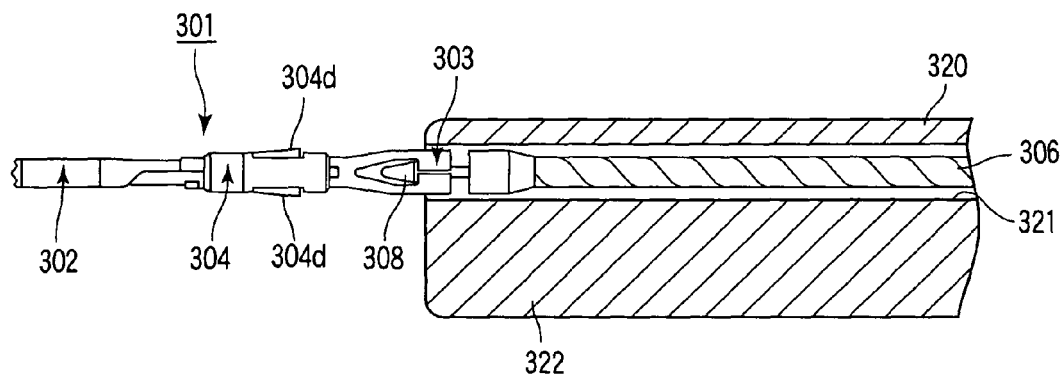
Figure 63C:
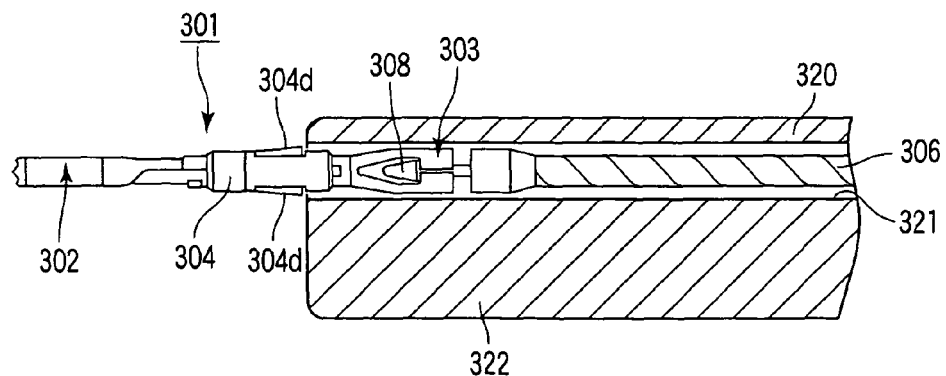

When the slider 311 is moved to the proximal end side, the operating wire 306 is pulled back to the proximal end side, and the proximal end faces of the retractable wings 304d of the press tube 304 engage with the distal end face of the insertion portion 322 of the endoscope 320, as shown in FIG. 63C.

When the slider 311 is further moved to the proximal end side to pull back the operating wire 306, the loop portion 302a of the clip 302 is pulled into the press tube 304 through the coupling member 303. The loop portion 302a of the clip 302 then comes into tight contact with the inner wall of the press tube 304, and the arms 302b spread apart to the limit, as shown in FIGS. 55A and 64B.

In this state, the operator approaches the clip 302 to a target region of the living tissue while observing it with the endoscope 320, and presses the tissue gripping portions 302c of the clip 302 against the target region. At this time, the operator inserts his/her thumb into the finger rest ring 310c of the operating portion 309 and grips the slider 311 with his/her index finger and middle finger to operate the operating portion 309. The finger rest ring 310c is rotatable with respect to the operation portion body 310. When the clip 302 is to be rotated to change its direction, the operation portion body 310 is rotated. At this time, the operation portion body 310 can be rotated while the thumb is kept inserted in the finger rest ring 310c.

When the slider 311 is further moved to the proximal end side, the operating wire 306 is moved backward, and the arms 302b of the clip 302 are pulled into the press tube 304 through the coupling member 303. As a consequence, as shown in FIGS. 56A and 64C, the arms 302b of the clip 302 are closed. As a result, the living tissue is reliably clamped between the arms 302b of the clip 302. At this time, since the press tube 304 is made of a resin having appropriate elasticity which is softer than the clip 302, the projections 302d of the clip 302 bite into the inner wall of the press tube 304 to restrict the clip 302 from moving in the press tube 304 in the axial direction, thereby maintaining the closed state.

When the slider 311 is further moved to the proximal end side to move the operating wire 306 backward, the small-diameter portion 303f serving as the fracture portion of the coupling member 303 of the clip 302 fractures, as shown in FIG. 64D. The clip 302 is then disengaged from the coupling member 303, and separates from the ligation device. As a consequence, the clip 302 is indwelled in the body cavity while gripping the living tissue.

For example, the living tissue of a bleeding region in the body cavity is clamped and pressed between the arms 302b of the clip 302, and the clip 302 is indwelled in the body cavity in this state. This makes it possible to stop bleeding by pressing the blood vessel in the bleeding region. The clip 302 is left alone for several days until the bleeding stops while gripping the living tissue. The projections 302d of the clip 302 bite into the inner wall of the press tube 304 to restrict the clip 302 from moving in the press tube 304 in the axial direction, thereby maintaining the closed state.

After the clip 302 is indwelled in the body cavity, the ligation device is removed from the channel 321 of the endoscope 320. When the coupling member 303 is to be removed from the arrowhead hook 308, the coupling member 303 is pivoted in the opening direction of the notched portion 303d of the coupling member 303 with respect to the axis of the operating wire 306. With this operation, the arrowhead hook 308 can be removed from the notched portion 303d of the coupling member 303.

In this manner, the clip unit 301 can be made to directly extend through the channel 321 of the endoscope 320, and each arm 302b of the clip 302 is formed to have an almost arcuated cross-section conforming to the curvature of the channel 321, the clip 302 can be smoothly moved back and forth in the channel 321 by operating the operating wire 306. Even if, the inner diameter of the channel 321 of the endoscope 320 is limited, the clip 302 can be increased in size. In addition, even the channel 321 has a small diameter, the living tissue can be reliably ligated with the clip 302 having a sufficient size of the ligation of the living tissue.

According to this embodiment, the operating wire 306 and clip 302 can be made to directly extend through the channel 321 of the endoscope 320. This makes it possible to thicken the operating wire 306 and transfer large operating force to the distal end portion. In addition, a sufficient amount of tissue gripped can be ensured by increasing the clip 302.

Figure 65:
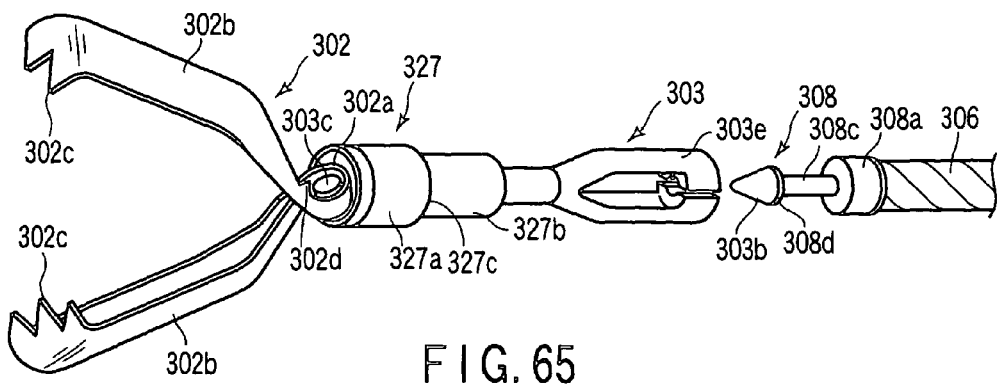
FIG. 65 is a perspective view of a clip unit according to the 15th embodiment of the present invention.
Figure 66A:
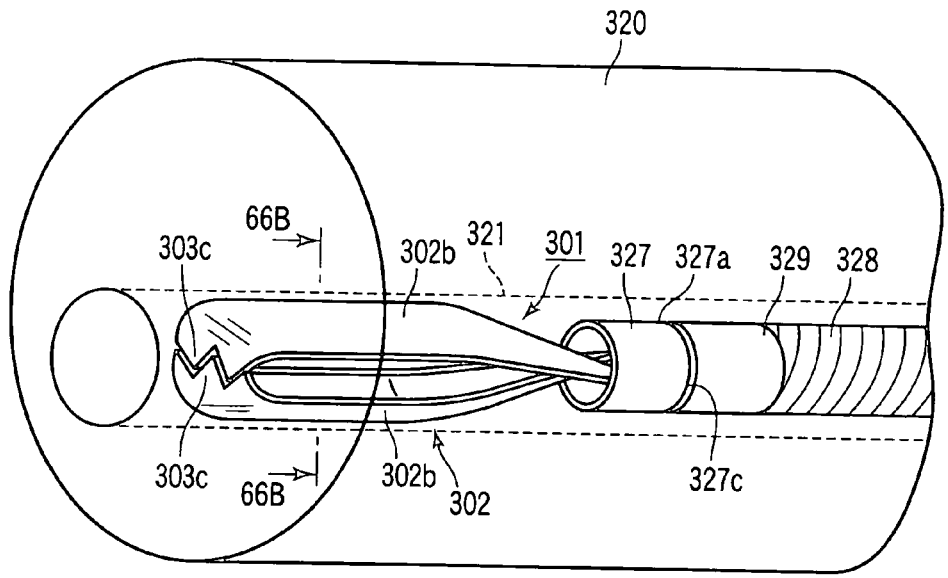
FIG. 66A is a perspective view of the clip unit inserted into the channel of an endoscope according to the embodiment.
Figure 66B:
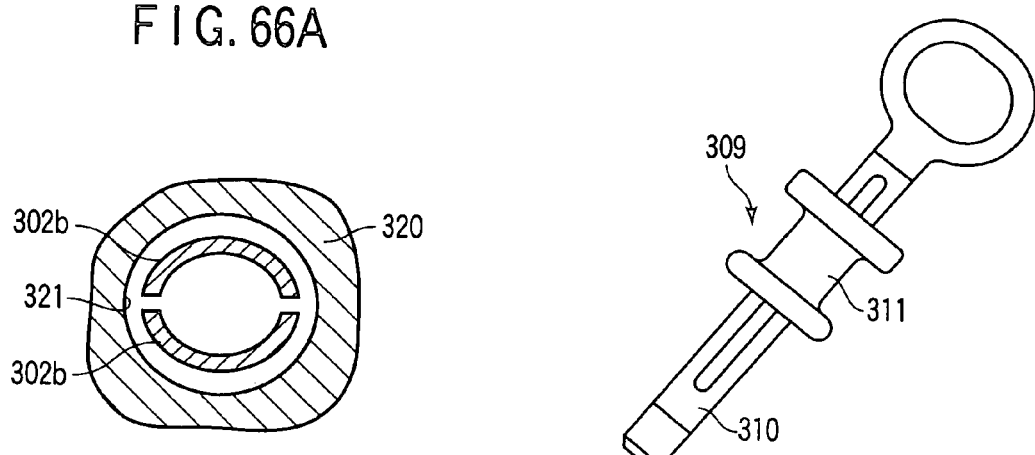
FIG. 66B is a sectional view taken along a line 66B-66B of FIG. 66A.
Figure 67:
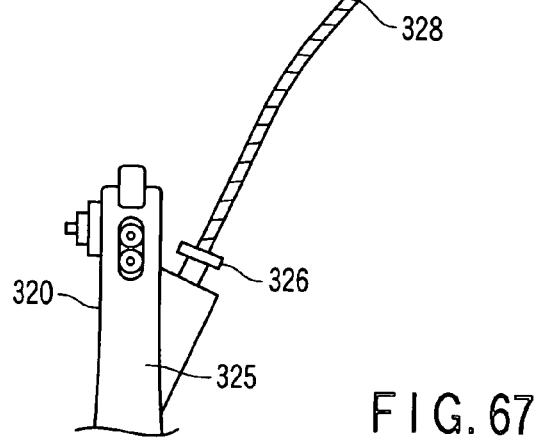
FIG. 67 is a view showing the operating portion of a ligation device according to the embodiment.

FIGS. 65 to 66B show the 15th embodiment. The same reference numerals as in the 14th embodiment denote the same constituent parts in the 15th embodiment, and a description thereof will be omitted. FIG. 65 is a perspective view of a clip unit 301. The outer circumference of a press tube 327 serving as a clamping member is formed such that a large-diameter portion 327a is formed on the distal end side, and a small-diameter portion 327b is formed on the proximal end side. Therefore, a stepped portion 327c is formed on the outer circumference of the press tube 327. This structure does not have the retractable wings 304d in the 14th embodiment. The press tube 327 is formed by using a resin having appropriate elasticity which is softer than a clip 302, and hence projections 302d of the clip 302 bite into the inner wall of the press tube 327. This restricts the clip 302 from moving in the press tube 327 in the axial direction and maintains the closed state.

An arrowhead hook 308 is provided at the distal end portion of an operating wire 306 as in the 14th embodiment, and is engaged with and connected to a grip portion 303e of a coupling member 303 forming the clip unit 301. The proximal end portion of the operating wire 306 is connected to a slider 311 of an operating portion 309.

As shown in FIGS. 66A and 66B, the operating wire 306 is inserted into a channel 321 of an endoscope 320 while extending through a coil sheath 328. A distal end member 329 which is in contact with the stepped portion 327c of the press tube 327 is provided at the distal end portion of the coil sheath 328. The proximal end portion of the coil sheath 328 is guided outside through the forceps opening 326 and is connected to an operating portion body 310 of the operating portion 309.

The function of this embodiment will be described next.

The clip unit 301 can be moved forward in the channel 321 of the endoscope 320 through the coil sheath 328 by the forward moving operation of the operating portion 309 guided outside through the forceps opening 326 of the endoscope 320. The clip unit 301 can be made to protrude from the channel 321.

Since a pair of arms 302b of the clip 302 have the property of spreading apart, they spread apart as soon as they protrude from the channel 321. Subsequently, when the slider 311 is moved to the proximal end side, the operating wire 306 is pulled back to the proximal end side, and the stepped portion 327c of the press tube 327 are engaged with the distal end member 329 of the coil sheath 328.

When the slider 311 is further moved to the proximal end side to pull back the operating wire 306, a loop portion 302a of the clip 302 is pulled into the press tube 327 through the coupling member 303. The loop portion 302a of the clip 302 then comes into tight contact with the inner wall of the press tube 327, and the arms 302b spread apart to the limit.

When the slider 311 is further moved to the proximal end side, the operating wire 306 moves backward, and the arms 302b of the clip 302 are pulled into the press tube 327 through the coupling member 303. As a consequence, the arms 302b of the clip 302 are closed, and the living tissue is reliably clamped between the arms 302b of the clip 302. At this time, since the press tube 327 is formed by using a resin having appropriate elasticity which is softer than the clip 302, the projections 302*d* of the clip 302 bite into the inner wall of the press tube 327, thereby restricting the clip 302 from moving in the axial direction inside the press tube 327 and maintaining the closed state.

When the operating wire 306 is further moved backward by moving the slider 311 to the proximal end side, the small-diameter portion 303*f* serving as the fracture portion of the coupling member 303 of the clip 302 fractures. The clip 302 is then disengaged from the coupling member 303, and separates from the ligation device. As a consequence, the clip 302 is indwelled in the body cavity while gripping the living tissue.

According to this embodiment, the press tube 327 need not be provided with retractable wings, and can be formed by using a cylindrical member having a stepped portion. This makes it possible to simplify the structure of the press tube, and allows it to smoothly move back and forth in the channel 321 of the endoscope 320.

The 16th embodiment of the present invention will be described below with reference to FIGS. 68 to 80D.

Figure 68:
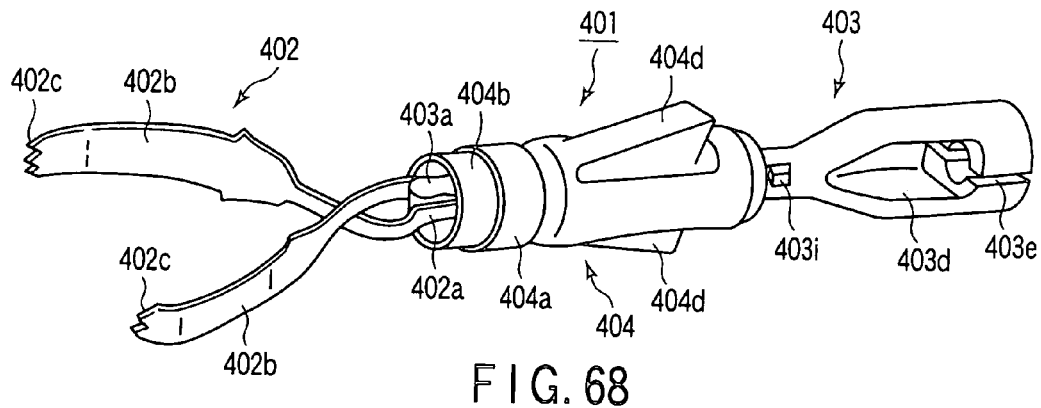
FIG. 68 is a perspective view of a clip unit according to the 16th embodiment of the present invention.

FIG. 68 is a perspective view of a clip unit 401 of a living tissue ligation device. The clip unit 401 is comprised of a clip 402, a coupling member 403, and a press tube 404 serving as a clamping member.

Figure 69A:
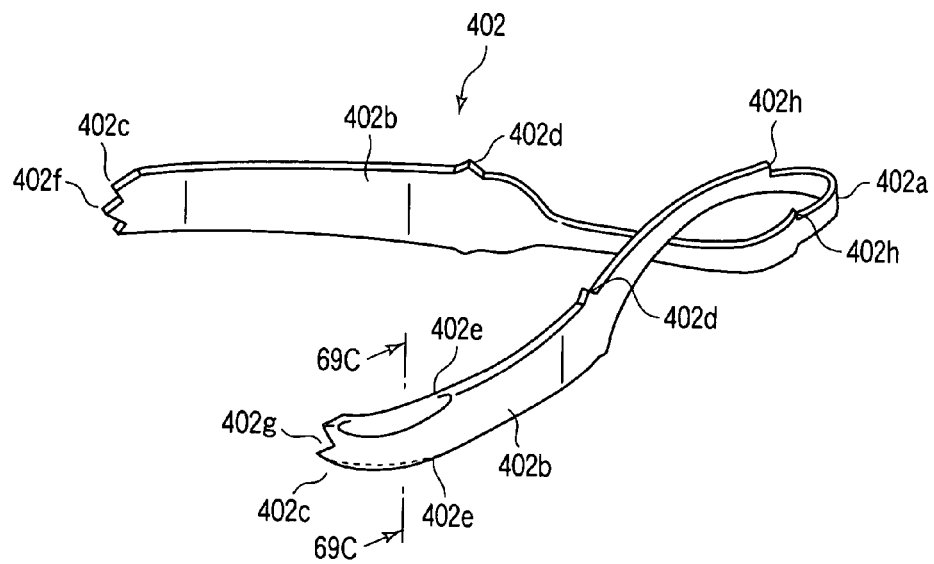
FIG. 69A is a perspective view of a clip according to the embodiment.
Figure 69B:
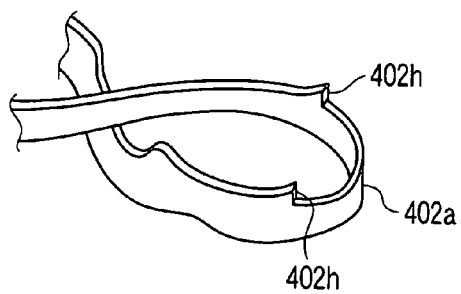
FIG. 69B is a perspective view of a loop portion.
Figure 69C:
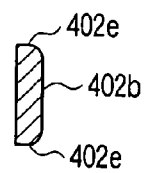
FIG. 69C is a sectional view taken along a line 69C-69C of FIG. 69A.

As shown in FIGS. 69A to 69C, the clip 402 has a loop portion 402*a* formed by, for example, bending a metal plate member such as a leaf spring member made of stainless steel or the like at its middle portion. In addition, a pair of arms 402*b* having the property of spreading apart are made to intersect at a position near the loop portion 402*a* and extend with their distal end portions spaced apart from each other. Tissue gripping portions 402*c* are formed on the distal end portions of the arms.

The intersecting portion of the arms 402*b* of the clip 402 is formed to have a width smaller than that of the distal end portions, and the tissue gripping portions 402*c* face each other. The proximal end portion of the loop portion 402*a* of the arms 402*b* is formed to have a width smaller than those of the remaining portions, loop stepped portions 402*h* serving as engaging members are formed on the two side portions of the loop portion 402*a* continuous from the proximal portion. Sawtooth-like projections 402*d* protruding in the plate width direction are provided at almost middle portions of the arms 402*b*. Each projection 402*d* is formed to have an inclined surface with an acute angle on the tissue grip portion side and an obtuse angle on the loop portion side such that the projection slidably moves on the inner surface of the press tube 404 in the direction in which the clip 402 is pulled into the press tube 404 and bites into the inner surface of the press tube 404 in the direction opposite to the pulling direction.

Both side edge portions 402*e* of that portion of the arm 402*b* which is near the distal end portion is chamfered or rounded by 0.05 mm or more to allow the arm 402*b* to easily slide on the inner portion of an introduction tube (to be described later). Each tissue gripping portion 402*c* is bent inward at an angle of about 90° to 150°. One tissue gripping portion 402*c* is formed into an almost triangular convex portion 402*f*, whereas the other tissue gripping portion 402*c* is formed into an almost triangular concave portion 402*g* so as to engage with the convex portion 2*f*.

The dimensions of the clip 402 will be described next. The size of the clip is set in consideration of gripping ability for the living tissue and insertion into an endoscope. For example, the clip has a thickness of 0.1 mm to 0.5 mm and a total length of 5 mm to 10 mm. The loop portion 402*a* has a circular or elliptic shape with a major axis length of 1 mm to 5 mm and a minor axis length of 1 mm to 5 mm. Each tissue gripping portion 402*c* has a length of about 0.5 mm to 1 mm, and a width of about 1 to 2 mm. The width of each loop stepped portion 402*h* is set to 0.1 mm or more. The width of each projection 402*d* is set to a width that allows the clip to be pulled into the press tube 404 and a distal end tube (to be described later), i.e., 1 mm or more.

As shown in FIGS. 70A and 70B, the coupling member 403 is manufacture by injection-molding a high-strength resin material such as a liquid crystal polymer or nylon, and has a cylindrical, rodlike shape. A projection portion 403*a* is provided on the distal end portion of the coupling member. The projection portion 403*a* laterally protrudes from a proximal portion 403*b*. A width 403*c* of the projection portion 403*a* is about 0.6 mm to 1.2 mm. The projection portion 403*a* is designed such that when the loop portion 402*a* of the clip 402 is hooked on the proximal end side surface portion of the projection portion 403*a* and the clip 402 is pulled into the press tube 404, the clip 402 slidably moves on the inner circumferential surface of the press tube 404 in a tight contact therewith, i.e., is slowly pulled into the press tube 404 with a large sliding resistance.

The other end portion of the coupling member 403 is bifurcated, and a gripping portion 403*e* which has a notched portion 403*d* and is used to grip an arrowhead hook (to be described later) is formed at the bifurcated portion. The intermediate portion of the coupling member 403 is formed into a small-diameter portion 403*f* serving as a fracture portion, an medium-diameter portion 403*g*, and a large-diameter portion 403*h* which extend from the distal end side to the proximal end side. The dimensions of small-diameter portion 403*f* are so set as to fracture when a fracturing force of 20 N to 60 N is applied thereto. That end face (proximal end face) of the coupling member 403 which is located on the opposite side to the large-diameter portion 403*h* is formed into a flat surface 403*j* perpendicular to the axial direction, and the large-diameter portion 403*h* is formed into a noncircular shape. Lock projections 403*i* are provided at portions of the outer circumferential surface of the large-diameter portion 403*h* at the terminal portion of the flat surface 403*j*. A slit 403*k* is formed in the middle portion of the flat surface 403*j* so as to extend to the notched portion 403*d* along the axial direction.

The dimensions of the coupling member 403 will be described. The total length of the coupling member 403 is about 10 mm. The inner diameter of the gripping portion 403*e* is about 0.6 mm. The outer diameter of the small-diameter portion 403*f* is 0.403 mm or more. The outer diameter of the large-diameter portion 403*h* is 1 mm to 1.403 mm. The height of each lock projection 403*i* is set to 0.1 mm or more.

The press tube 404 is manufactured by injection-molding a material softer than the clip 2, for example, a high-rigidity resin having appropriate elasticity such as PPA (polyphthalamide) or PA (polyamide). The press tube 404 closes the arms 402*b* of the clip 402 when the press tube 404 is fitted on the arms 402*b* of the clip 402. A distal end tube 404*a* made of a high-strength metal such as stainless steel is fitted on the distal end portion of the press tube 404.

The distal end tube 404*a* has an inner diameter that allows it to be fitted on the press tube 404, and an outer diameter that is almost equal to that of the press tube 404 and smaller than that of a distal end fitting portion 404*b* of the press tube 404. The distal end tube 404*a* is located behind the distal end of the distal end fitting portion 404*b* so as to form a pseudo-tapered portion. This allows the distal end tube 404*a* to smoothly move in the bent introduction tube without being caught on its inner wall.

The inner diameter of the proximal end portion of the press tube 404 has a rear end diameter reducing portion 404*c* to tightly fit the proximal end portion on the large-diameter portion 403h of the coupling member 403, thereby forming an inner diameter stepped portion 404h serving as a lock member having a level difference of 0.1 mm or more. When the clip 402 is pulled into the press tube 404, the loop stepped portions 402h of the clip 402 engages (comes into contact) with the inner diameter stepped portion 404h, thereby preventing the clip 402 from being pulled into the press tube 404 beyond the closing position.

A pair of retractable wings 404d which are elastically retractable in the radial direction are provided on the outer circumferential portion of the press tube 404. In addition, a rear end inclined surface 404e is provided on the rear end edge portion of the press tube 404.

The dimensions of the press tube 404 will be described. The total length and inner and outer diameters of the press tube 402 are set in accordance with the size of the clip 402. The inclined surface 404b' of the distal end fitting portion 404b has an angle of 15 to 90° and an entrance diameter of about 1.6 mm, which are suitable for allowing the clip 402 to grip the tissue. The retractable wings 404d are almost triangular and have a maximum protrusion width of 2 mm or more. The distance between the inclined surface 404e formed on the rear end edge and the large-diameter portion 403h of the coupling member 403 is 0.5 mm or less.

The assembly of the clip unit 401 will be described next. First of all, the coupling member 403 is inserted from the rear end side of the press tube 404, and the projection portion 403a of the coupling member 403 is made to completely protrude from the press tube 404. At this time, the lock projections 403i provided on the large-diameter portion 403h of the coupling member 403 have a size that does not allow the lock projections 403i to be inserted into the press tube 404. However, since the flat surface 403j is provided on the large-diameter portion 403h, the press tube 404 can deform into an elliptic shape. This allows the lock projections 403i to be inserted into the press tube 404 without being cut or deformed. In this state, the loop portion 402a of the clip 402 can be locked to the projection portion 403a of the coupling member 403.

Figures 72, 74A, 74B:
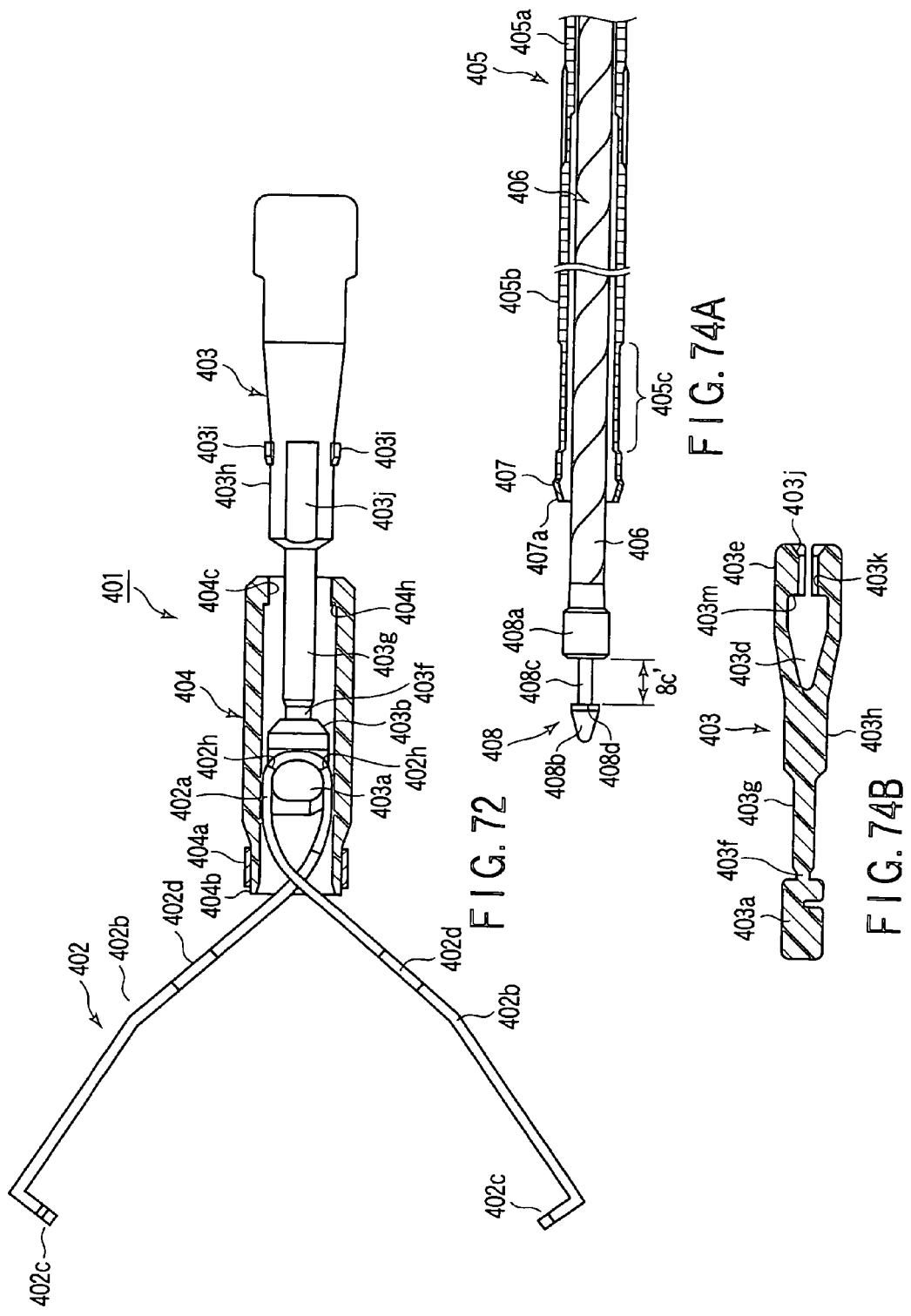
FIG. 72 is a partially cutaway side view showing the clip unit in a state wherein the clip according to the embodiment is open.
FIG. 74A is a partially cutaway side view of the distal end portion of a ligation device according to the embodiment.
FIG. 74B is a longitudinal sectional view of a coupling member.

In a state immediately before the clip 402 opens to the limit, as shown in FIGS. 71A and 71B, the loop portion 402a of the clip 402 is held in tight contact with the inner circumferential surface of the press tube 404. When the coupling member 403 is pulled to the operator side in this state, the loop portion 402a of the clip 402 is slowly pulled into the press tube 404 while slidably moving on the inner circumferential surface. As shown in FIG. 72, therefore, the arms 402b of the clip 402 controllably spread apart. When the coupling member 403 is further pulled to the operator side in this state, the arms 402b of the clip 402 close, as shown in FIGS. 73A to 73D.

At this time, since the press tube 404 is formed by using a resin having appropriate elasticity which is softer than the clip 402, the distal end fitting portion 404b of the press tube 404 is deformed into a noncircular state by the arms 402b and projections 402d of the clip 402, as shown in FIGS. 73A to 73C. This restricts the clip 402 from moving in the axial direction inside the press tube 404 and maintains the closed state.

When the clip 402 is further pulled into the press tube 404, the loop stepped portions 402h engage with the inner-diameter stepped portions 404h of the press tube 404 to prevent the clip 402 from being pulled into the press tube 404 beyond the closing position, as shown in FIGS. 73B and 73D.

An introduction tube 405 and operating wire 406 shown in FIGS. 74A and 74B will be described next. The introduction tube 405 is comprised of an operator-side coil 405a having flexibility which is formed by tightly winding a spring material such as stainless steel, and a distal end coil 405b having flexibility which is connected to the distal end portion of the operator-side coil 405a and formed by tightly winding a spring material such as stainless steel.

The operator-side coil 405a has an outer diameter that allows it to extend through the channel of an endoscope, for example, 2 mm to 6 mm, and an inner diameter that allows the operating wire 406 to extend through the operator-side coil 405a. The operator-side coil 405a has a thickness of about 0.25 to 0.7 mm. The distal end coil 405b has an outer diameter that allows it to extend through the channel of the endoscope, for example, 2 mm or more, and an inner diameter that allows the clip unit 401 and operating wire 406 to extend through the distal end coil 405b. The distal end coil 405b has a thickness of about 0.25 to 0.7 mm.

A thin portion 405c is formed near the distal end of the distal end coil 405b by a post-process such as grinding. The thin portion 405c has a length of about 1 mm to 10 mm and a thickness of about 0.2 mm to 0.65 mm.

Providing the thin portion 405c near the distal end of the distal end coil 405b increases the flexibility and improves the insertibility with respect to the channel of the endoscope. The distal end coil 405b has undergone a heat treatment. After the heat treatment, the distal end coil 405b is ground to form the thin portion 405c. Consequently, the thin portion 405c has a glossy metal surface distinctive from the remaining portions, and hence provides a marking effect. Therefore, when the distal end coil 405b protrudes from the distal end portion of the endoscope, the operator can check the protrusion amount with the endoscope.

A distal end chip 407 made of a metal such as stainless steel is provided at the distal end portion of the distal end coil 405b. The distal end chip 407 has an outer diameter that allows it to extend through the channel of the endoscope, for example, 2 mm to 6 mm, and an inner diameter that allows the clip unit 401 or operating wire 406 to extend through the distal end coil 405b, for example, about 2 mm. A chip inclined surface 407a having an angle of 5° to 90° is formed on the outer circumferential surface of the distal end chip 407 so as to gradually reduce the diameter.

The operating wire 406 is formed by using a stranded wire comprised of core and side strands of metal wires having appropriate elasticity, e.g., stainless steal or NiTi. The operating wire 406 has an outer diameter of 1.2 mm to 1.8 mm to have a clearance of 0.4 mm or less between itself and the inner diameter of the distal end coil 405b. In addition, a Teflon (registered trademark) coat is formed on the outer surface of the operating wire 406. Reducing the clearance between the inner diameter of the distal end coil 405b and the outer diameter of the operating wire 406 to 0.0403 mm or less by thickening the operating wire 406 makes it possible to prevent the operating wire 406 from deforming and buckling.

A cylindrical wire fixing portion 408a made of a metal material such as stainless steel is fitted on the distal end portion of the operating wire 406. An arrowhead hook 408 is integrally provided with the cylindrical wire fixing portion 408a through a shaft portion 408c.

The arrowhead hook 408 has an arrowhead inclined portion 408b which is formed at the distal end portion of the shaft portion 408c, and has a conical shape and an angle of 10° to 120°. An arrowhead large-diameter portion 408d has a diameter of about 0.8 mm to 1.2 mm.

FIGS. 75 to 77 show an operating portion 409. An operating portion body 410 is comprised of a cylindrical portion 410a on the distal end side, a shaft-like portion 410b extending to the proximal end side integrally with the cylindrical portion 410a, and a finger rest ring 410c rotatably provided on the proximal end portion of the shaft-like portion 410b. A slit 410d is provided for the shaft-like portion 410b of the operating portion body 410 in the axial direction. A slider 411 partly inserted in the slit 410d is retractably provided on the shaft-like portion 410b. The slider 411 has a finger rest concave portion 411a on its outer circumferential surface. The proximal end side of the operating wire 406 extends through an internal hole 411b of the slider 411, and a proximal end portion 406b of the operating wire 406 is connected to the slider 411. Therefore, as the slider 411 moves back and forth with respect to the operating portion body 410, the operating wire 406 moves back and forth in the introduction tube 405.

A pipe 415 made of stainless steel is fitted on the operating wire 406 which extends through the cylindrical portion 410a of the operation portion body 410. An inner circumference large-diameter portion 416 is formed at the distal end portion of the cylindrical portion 410a, and a coil joint tube 417 fixed to the cylindrical portion 410a is fixed to the inner circumference large-diameter portion 416.

A fracture prevention tube 418 fitted on the operating wire 406 is coupled to the coil joint tube 417. The fracture prevention tube 418 is formed by using a spring material such as stainless steel or a resin material having appropriate softness such as a silicone heat-shrinkable tube, and is fitted on the operator-side coil 405a of the introduction tube 405. Providing the coupling portion between the coil joint tube 417 and the fracture prevention tube 418 inside the operation portion body 410 allows the operation portion body 410 to protect the coupling portion having low strength.

The function of the living tissue ligation device having the above arrangement will be described next.

As shown in FIG. 78, the operator introduces the introduction tube 405 into the body cavity through a channel 421 of an endoscope 420 inserted in the body cavity in advance, and guides the distal end of the introduction tube 405 to a target region while observing the inside of the body cavity with the endoscope 420.

Figure 79A:
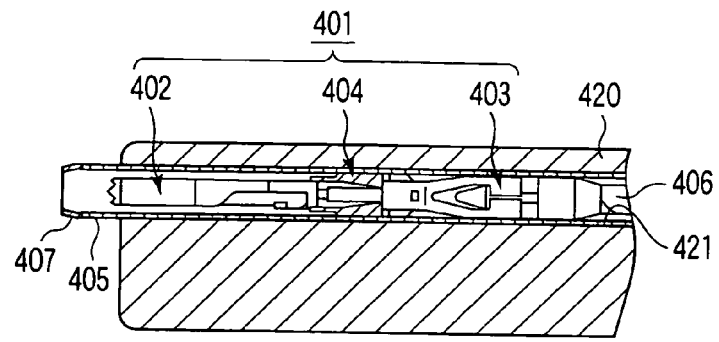
FIGS. 79A to 79C are views for explaining the operation of the device according to the embodiment.
Figure 79B:
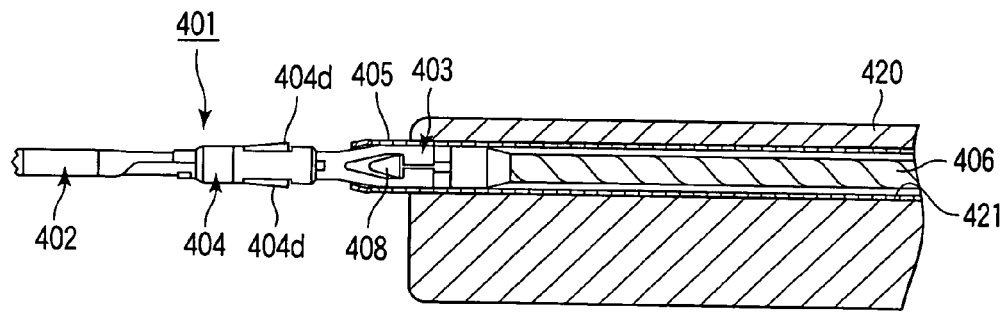

FIGS. 79 and 80 show a sequence of ligating the living tissue with the clip 402. As shown in FIG. 79A, when the operator pushes the slider 411 to the distal end side, the clip unit 401 moves forward in the introduction tube 405 through the operating wire 406. When the operating wire 406 is further moved forward by the slider 411, the clip unit 401 protrudes from the introduction tube 405, as shown in FIG. 79B. At this time, since each retractable wing 404d of the press tube 404 has a down grade toward the distal end side, the clip unit 401 is pushed out smoothly without any resistance. At this time, the retractable wings 404d of the press tube 404 are released from the contact state with the inner surface of the introduction tube 405, and protrude in the outer circumferential direction of the press tube 404. In addition, as shown in FIG. 80A, since the pair of arms 402b of the clip 402 have the property of spreading apart, they spread apart at the same time when they protrude from the introduction tube 405.

Figure 79C:
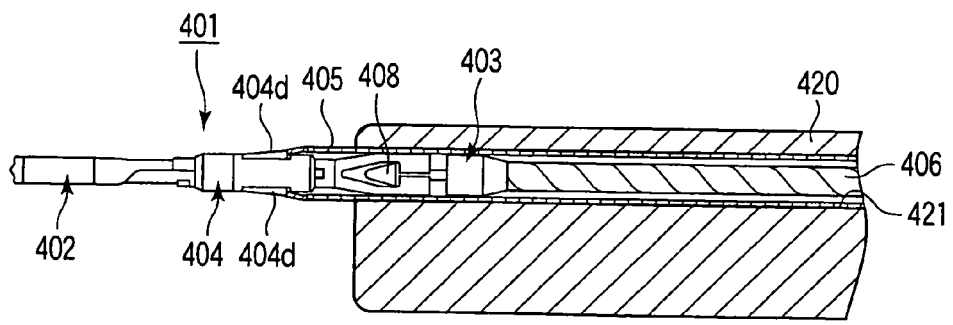

When the slider 411 is moved to the proximal end side afterward, the operating wire 406 is pulled back to the proximal end side, as shown in FIG. 79C, and the proximal end faces of the retractable wings 404d of the press tube 404 engage with the end face of the distal end chip 407.

Figure 80A:
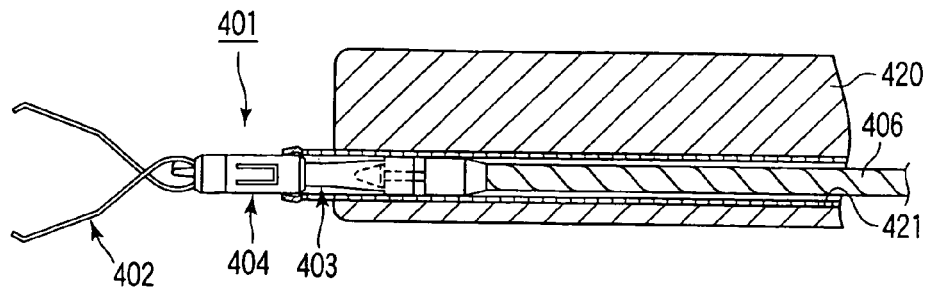
FIGS. 80A to 80D are views for explaining the operation of the device according to the embodiment.
Figure 80B:
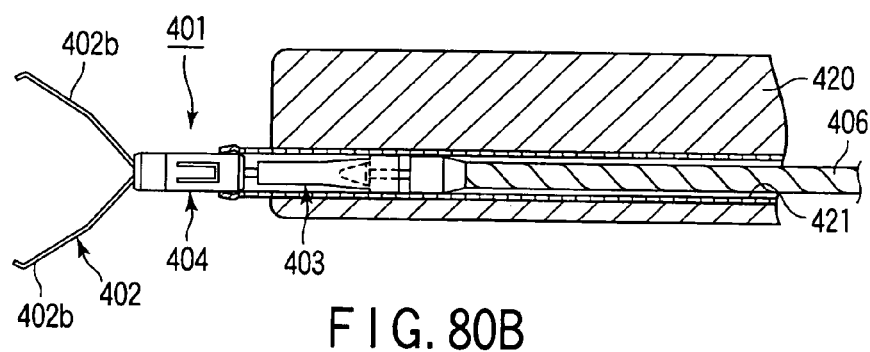

When the slider 411 is further moved to the proximal end side to pull back the operating wire 406, the loop portion 402a of the clip 402 is pulled into the press tube 404 through the coupling member 403. At this time, the loop portion 402a of the clip 402 comes into tight contact with the inner wall of the press tube 404, and the arms 402b spread apart to the limit, as shown in FIGS. 71A and 80B.

In this state, the operator approaches the clip 402 to a target region of the living tissue while observing it with the endoscope 420, and presses the tissue gripping portions 402c of the clip 402 against the target region. At this time, the operator inserts his/her thumb into the finger rest ring 410c of the operating portion 409 and grips the slider 411 with his/her index finger and middle finger to operate the operating portion 409. The finger rest ring 410c is rotatable with respect to the operation portion body 410. When the clip 402 is to be rotated to change its direction, the operation portion body 410 is rotated. At this time, the operation portion body 410 can be rotated while the thumb is kept inserted in the finger rest ring 410c.

Figure 80C:
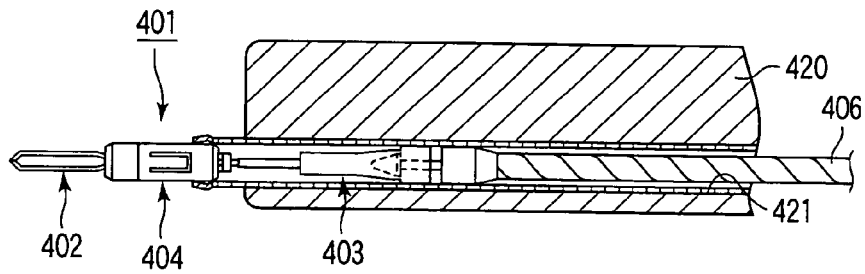

When the slider 411 is further moved to the proximal end side, the operating wire 406 is moved backward, and the arms 402b of the clip 402 are pulled into the press tube 404 through the coupling member 403. As a consequence, the arms 402b of the clip 402 are closed, as shown in FIGS. 73A and 80C. As a result, the living tissue is reliably clamped between the arms 402b of the clip 402. At this time, since the press tube 404 is made of a resin having appropriate elasticity which is softer than the clip 402, the projections 402d of the clip 402 bite into the inner wall of the press tube 404 to restrict the clip 402 from moving in the press tube 404 in the axial direction, thereby maintaining the closed state.

When the clip 402 is pulled into the press tube 404, the loop stepped portion 402h of the clip 402 engages (comes into contact) with the inner-diameter stepped portion 404h to prevent the clip 402 from being pulled into the press tube 404 beyond the closing position, as shown in FIG. 73B.

Figure 80D:
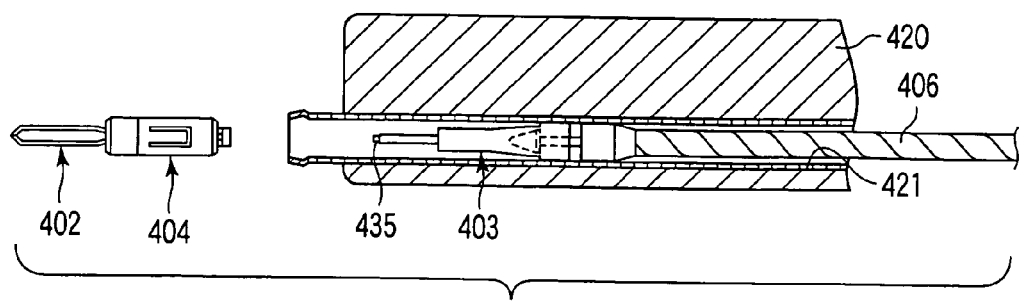

When the slider 411 is further moved to the proximal end side to move the operating wire 406 backward, the small-diameter portion 403f serving as the fracture portion of the coupling member 403 of the clip 402 fractures, as shown in FIG. 80D. The clip 402 is then disengaged from the coupling member 403, and separates from the ligation device, together with the press tube 404. As a consequence, the clip 402 is indwelled in the body cavity while gripping the living tissue.

For example, the living tissue of a bleeding region in the body cavity is clamped and pressed between the arms 402b of the clip 402, and the clip 402 is indwelled in the body cavity in this state. This makes it possible to stop bleeding by pressing the blood vessel in the bleeding region. The clip 402 is left alone for several days until the bleeding stops while gripping the living tissue. The projections 402d of the clip 402 bite into the inner wall of the press tube 404 to restrict the clip 402 from moving in the press tube 404 in the axial direction, thereby maintaining the closed state.

After the clip 402 is indwelled in the body cavity, the ligation device is removed from the channel 421 of the endoscope 420. When the coupling member 403 is to be removed from the arrowhead hook 408, the coupling member 403 is pivoted in the opening direction of the notched portion 403d of the coupling member 403 with respect to the axis of the operating wire 406. With this operation, the arrowhead hook 408 can be removed from the notched portion 403d of the coupling member 403.

What is claimed is:

1. A living tissue ligation device comprising:
   a clip having a plurality of arms which close to grip living tissue;
   a clamping member having a through hole defined by an inner peripheral surface into which the clip is inserted to close the arms of the clip by urging the arms with the inner peripheral surface;

a coupling member which is to be inserted into the clamping member and engages with the clip to allow the clip to be inserted into the clamping member; and a lock mechanism having a first lock portion disposed on the clip and a second lock portion disposed on the inner peripheral surface of the clamping member, the first and second lock portions being engaged with each other to prevent the clip from forwardly moving against the clamping member so that the clamping member holds the arms of the clip in a closed state when the clip engages with the clamping member;

wherein the first lock portion includes at least one projection and the second lock portion includes a surface which interferes with the at least one projection such that the at least one projection lodges into the surface to engage the clamping member when the clip is inserted into the clamping member and wherein the location of the surface into which the at least one projection lodges is distal to a proximal end of the clamping member.

2. A living tissue ligation device according to claim 1, wherein the surface is formed of a material softer than a material forming the at least one projection.

3. A living tissue ligation device according to claim 2, wherein said at least one projection has a tip end made of metal, and the second lock portion is made of a high-rigidity resin.

4. A living tissue ligation device according to claim 1, wherein at least a part of the clamping member is left in a body cavity together with the clip which has gripped the living tissue.

5. A living tissue ligation device according to claim 1, wherein at least a part of the clamping member is left in a body cavity together with said plurality of arms which have gripped the living tissue.

6. A living tissue ligation device according to claim 1, wherein the first and second lock portions engage in a direction different from a direction of opening and closing of the plurality of arms of the clip.

7. A living tissue ligation device according to claim 1, wherein said at least one projection has a sawtooth-like shape which has opposite first and second inclined surfaces, the first and second inclined surfaces intersecting at a sharp tip end of the projection, the first inclined surface being located on a forward side of the clip and being inclined more steeply than the second inclined surface located on a rearward side of the clip.

8. A living tissue ligation device comprising:

a clip having at least two arms having tip portions which grip living tissue, the arms gripping no living tissue except the tip portions;

a clamping mechanism having a through hole defined by an inner peripheral surface, the clamping mechanism being fitted and mounted on the clip to close the arms of the clip in a closed state, and to hold the closed state by urging the arms with the inner peripheral surface;

a coupling member which engages with the clip;

an operating member which is coupled to the coupling member and is made to retractably extend through a channel of an endoscope, and a lock mechanism to prevent the clip from forwardly moving against the clamping mechanism so that the clamping mechanism holds the arms of the clip in a closed state when the clip engages with the clamping mechanism;

wherein each of the at least two arms of the clip is formed to have a substantially C-shaped cross-section in a plane perpendicular to a longitudinal axis of the channel and the clip is allowed to directly extend through the channel and the clip is configured from an elongated sheet which is curved in a lateral direction into the C-shaped cross-section, the elongated sheet having the tip portions at distal ends thereof for gripping the tissue, the lock mechanism includes at least one projection and a surface which interferes with the at least one projection such that the at least one projection lodges into the surface to engage the clamping mechanism when the clip is inserted into the clamping mechanism and the location of the surface into which the at least one projection lodges is distal to a proximal end of the clamping mechanism.

9. A living tissue ligation device according to claim 8, wherein when the clip closes, the at least two arms form a substantially cylindrical shape.

10. A living tissue ligation device according to claim 8, wherein the tip portions of the arms have forward end surfaces of a complemental shape which are able to be meshed with each other.

11. A living tissue ligation device according to claim 10, wherein the tip portions of the arms are inwardly bent so that the forward end surfaces face with each other.

12. A living tissue ligation device according to claim 8, wherein the at least two arms include elongated pieces, each of the tip portions being extended from one end of each of the elongated pieces, the other ends of the elongated pieces being connected with each other, the elongated pieces having inner surfaces facing each other, each of the inner surfaces having an elongated concave extending in a longitudinal direction of the elongated piece.

13. A living tissue ligation device according to claim 12, wherein each of the elongated pieces is curved in a lateral direction normal to the longitudinal direction to form the concave.

14. A living tissue ligation device according to claim 8, wherein at least a part of the clamping member is left in a body cavity together with the clip which has gripped the living tissue.

15. A living tissue ligation device comprising:

a pair of arms which are introduced into a body cavity through a channel of an endoscope and grip living tissue;

a clamping member having a through hole defined by an inner peripheral surface, the clamping member moves the arms in a direction to close in a closed state and holds the arms in the closed state by urging the arms with the inner peripheral surface; and a lock mechanism to prevent the clip from forwardly moving against the clamping member so that the clamping member holds the arms of the clip in a closed state when the clip engages with the clamping member;

wherein each of the pair of arms is formed to have substantially C-shaped cross-section in a plane perpendicular to a longitudinal axis of the channel and the arms are indwelled in the living tissue while gripping the living tissue and the clip is configured from an elongated sheet which is curved in a lateral direction into a C-shaped cross-section, the elongated sheet having tip portions at distal ends thereof for gripping the tissue, the lock mechanism includes at least one projection and a surface which interferes with the at least one projection such that the at least one projection lodges into the surface to engage the clamping member when the clip is inserted into the clamping member and the location of the surface into which the at least one projection lodges is distal to a proximal end of the clamping member.

16. A living tissue ligation device comprising:

a pair of arms which are introduced into a body cavity through a channel of an endoscope and grip living tissue; and a clamping member having a through hole defined by an inner peripheral surface, the clamping member moves the arms to a direction to close in a closed state and holds the arms in the closed state by urging the arms with the inner peripheral surface, and a lock mechanism to prevent the clip from forwardly moving against the clamping member so that the clamping member holds the arms of the clip in a closed state when the clip engages with the clamping member;

wherein each of the pair of arms is formed to have a substantially C-shaped cross-section in a plane perpendicular to a longitudinal axis of the channel, are made to directly extend through the channel, the arms are indwelled in a living body while gripping the living tissue and the clip is configured from an elongated sheet which is curved in a lateral direction into the C-shaped cross-section, the elongated sheet having tip portions at distal ends thereof for gripping the tissue, the lock mechanism includes at least one projection and a surface which interferes with the at least one projection such that the at least one projection lodges into the surface to engage the clamping member when the clip is inserted into the clamping member and the location of the surface into which the at least one projection lodges is distal to a proximal end of the clamping member.

17. A living tissue ligation device comprising:

a clip having arms which grip living tissue;

a clamping member having a through hole defined by an inner peripheral surface, the clamping member, the clamping member being fitted and mounted on the clip to close the arms of the clip in a closed state and holds the arms in the closed state by urging the arms with the inner peripheral surface; and an engaging member which engages with the clip and the clamping member to prevent the clip from being pulled into the clamping member beyond a closing position;

wherein the engaging member is provided only for both the clip and the clamping member; and wherein the engaging member includes at least one projection and the clamping member includes a surface which interferes with the at least one projection such that the at least one projection lodges into the surface to engage the clamping member when the clip is inserted into the clamping member, and the location of the surface into which the at least one projection lodges is distal to a proximal end of the clamping member.

18. A living tissue ligation device according to claim 17, wherein the engaging member for the clip and the clamping member comprises a stepped portion with which the clip comes into contact when the clip is pulled into the clamping member and opens.

19. A living tissue ligation device according to claim 17, wherein the surface is formed of a material softer than a material forming the at least one projection.

20. A living tissue ligation device according to claim 19, wherein said at least one projection has a tip end made of metal, and the surface is made of a high-rigidity resin.

21. A living tissue ligation device according to claim 17, wherein said at least one projection has a sawtooth-like shape which has opposite first and second inclined surfaces, the first and second inclined surfaces intersecting at a sharp tip end of the projection, the first inclined surface being located on a forward side of the clip and being inclined more steeply than the second inclined surface located on a rearward side of the clip.

* * * * *